(12) United States Patent
Schreck et al.

(10) Patent No.: US 11,497,597 B2
(45) Date of Patent: Nov. 15, 2022

(54) MODULAR STENT GRAFT SYSTEMS AND METHODS WITH INFLATABLE FILL STRUCTURES

(71) Applicant: Endologix LLC, Irvine, CA (US)

(72) Inventors: Stefan Schreck, San Clemente, CA (US); Craig Welk, Laguna Niguel, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 16/679,959

(22) Filed: Nov. 11, 2019

(65) Prior Publication Data

US 2020/0069412 A1     Mar. 5, 2020

Related U.S. Application Data

(63) Continuation of application No. 15/310,198, filed as application No. PCT/US2015/029292 on May 5, 2015, now Pat. No. 10,470,870.

(Continued)

(51) Int. Cl.
*A61F 2/07*        (2013.01)
*A61F 2/954*      (2013.01)
(Continued)

(52) U.S. Cl.
CPC .......... *A61F 2/07* (2013.01); *A61B 17/12118* (2013.01); *A61B 17/12136* (2013.01);
(Continued)

(58) Field of Classification Search
CPC ........ A61B 17/12109; A61B 17/12113; A61B 17/12118; A61B 17/12136;
(Continued)

(56) References Cited

U.S. PATENT DOCUMENTS 5,330,528 A    7/1994   Lazim
5,665,117 A *   9/1997   Rhodes ..................... A61F 2/07
                                           606/192

(Continued)

FOREIGN PATENT DOCUMENTS

CN       102076282 A    5/2011
CN       101754727 B    4/2014
(Continued)

OTHER PUBLICATIONS

Chinese Office Action dated Aug. 12, 2020, from application No. 201810370663.0.

(Continued)

*Primary Examiner* — Ryan J. Severson
(74) *Attorney, Agent, or Firm* — Foley & Lardner LLP

(57) ABSTRACT

An apparatus includes a first stent graft that is at least partially insertable into a first blood vessel. The first stent graft has a first end, a second end, an inside surface, and an outside surface. The apparatus also includes an inflatable fill structure fixed to a portion of the outside surface of the first stent graft. The inflatable fill structure includes an outer membrane that is configured to extend beyond the first end of the first stent graft when the inflatable fill structure is in a filled state.

19 Claims, 81 Drawing Sheets

Related U.S. Application Data

(60) Provisional application No. 62/004,925, filed on May 30, 2014.

(51) Int. Cl.
 *A61B 17/12* (2006.01)
 *A61F 2/06* (2013.01)
 *A61F 2/945* (2013.01)
 *A61F 2/89* (2013.01)
 *A61F 2/82* (2013.01)

(52) U.S. Cl.
 CPC .............. *A61F 2/954* (2013.01); *A61F 2/89* (2013.01); *A61F 2/945* (2013.01); *A61F 2002/067* (2013.01); *A61F 2002/077* (2013.01); *A61F 2002/826* (2013.01); *A61F 2210/0076* (2013.01); *A61F 2210/0085* (2013.01); *A61F 2250/0003* (2013.01); *A61F 2250/0063* (2013.01); *A61F 2250/0098* (2013.01)

(58) Field of Classification Search
 CPC .............. A61B 17/12181; A61F 2/07; A61F 2002/077; A61F 2002/823; A61F 2250/0003
 See application file for complete search history.

(56) References Cited

U.S. PATENT DOCUMENTS

| | | | | |
|---|---|---|---|---|
| 5,693,088 | A * | 12/1997 | Lazarus | A61F 2/07 606/195 |
| 7,105,017 | B2 * | 9/2006 | Kerr | A61F 2/07 623/1.13 |
| 8,048,145 | B2 | 11/2011 | Evans et al. | |
| 8,231,665 | B2 * | 7/2012 | Kim | A61B 17/12022 623/1.11 |
| 8,231,666 | B2 * | 7/2012 | Kim | A61F 2/958 623/1.11 |
| 8,252,040 | B2 * | 8/2012 | Cox | A61F 2/88 623/1.15 |
| 8,535,367 | B2 * | 9/2013 | Kim | A61B 17/12022 623/1.11 |
| 8,562,662 | B2 * | 10/2013 | Kim | A61B 17/12036 623/1.11 |
| 8,647,377 | B2 * | 2/2014 | Kim | A61B 17/12022 623/1.11 |
| 8,870,909 | B2 * | 10/2014 | Cox | A61B 17/12022 606/200 |
| 8,870,941 | B2 | 10/2014 | Evans et al. | |
| 8,936,633 | B2 * | 1/2015 | Kim | A61B 17/12118 623/1.11 |
| 8,945,199 | B2 | 2/2015 | Ganpath et al. | |
| 9,295,569 | B2 * | 3/2016 | Kim | A61B 17/1219 |
| 9,561,096 | B2 * | 2/2017 | Kim | A61B 17/12022 |
| 9,561,097 | B1 * | 2/2017 | Kim | A61B 17/1219 |
| 9,622,753 | B2 * | 4/2017 | Cox | A61L 31/16 |
| 10,349,946 | B2 * | 7/2019 | Herbowy | A61M 25/09 |
| 10,390,836 | B2 * | 8/2019 | Schreck | A61M 25/104 |
| 10,470,868 | B2 * | 11/2019 | Kim | A61B 17/12118 |
| 10,470,869 | B2 * | 11/2019 | Kim | A61F 2/958 |
| 10,470,870 | B2 * | 11/2019 | Schreck | A61B 17/12118 |
| 10,682,144 | B2 * | 6/2020 | Evans | A61B 17/12118 |
| 10,743,979 | B2 * | 8/2020 | Robin | A61F 2/07 |
| 2001/0027338 | A1 | 10/2001 | Greenberg | |
| 2002/0151957 | A1 | 10/2002 | Kerr | |
| 2004/0215321 | A1 | 10/2004 | Holman et al. | |
| 2006/0212112 | A1 | 9/2006 | Evans et al. | |
| 2006/0292206 | A1 | 12/2006 | Kim et al. | |
| 2007/0150041 | A1 * | 6/2007 | Evans | A61F 2/954 623/1.11 |
| 2007/0162106 | A1 | 7/2007 | Evans et al. | |
| 2008/0275536 | A1 * | 11/2008 | Zarins | A61F 2/07 623/1.11 |
| 2009/0318949 | A1 | 12/2009 | Ganpath et al. | |
| 2009/0319029 | A1 | 12/2009 | Evans et al. | |
| 2011/0022153 | A1 | 1/2011 | Schreck et al. | |
| 2011/0160846 | A1 | 6/2011 | Bishop et al. | |
| 2012/0184982 | A1 * | 7/2012 | Herbowy | A61B 17/12136 606/194 |
| 2013/0204351 | A1 | 8/2013 | Cox et al. | |
| 2013/0261734 | A1 | 10/2013 | Young et al. | |
| 2014/0142685 | A1 | 5/2014 | Kim et al. | |
| 2017/0239035 | A1 * | 8/2017 | Schreck | A61B 17/12136 |
| 2020/0069412 | A1 * | 3/2020 | Schreck | A61F 2/954 |

FOREIGN PATENT DOCUMENTS

| | | |
|---|---|---|
| FR | 2834199 A1 | 7/2003 |
| JP | 2011-522614 A | 8/2011 |
| JP | 2011-522615 A | 8/2011 |
| JP | 2011-530373 A | 12/2011 |
| JP | 2011-530677 | 12/2011 |
| WO | WO-2008/023160 A1 | 2/2008 |
| WO | WO-2011/017123 A2 | 2/2011 |
| WO | WO-2013/136636 A1 | 9/2013 |

OTHER PUBLICATIONS

Chinese Office Action dated Aug. 5, 2019, from application No. 201810370663.0.
Chinese Office Action dated Jun. 25, 2019, from application No. 201580039348.4.
Chinese Office Action dated Oct. 30, 2017, from application No. 201580039348.4.
Chinese Office Action dated Sep. 25, 2018, from application No. 201580039348.4.
Extended European Search Report dated Feb. 7, 2019, from application No. 15800658.5.
Final Office Action dated Feb. 25, 2019, from U.S. Appl. No. 15/310,198.
International Preliminary Report on Patentability dated Dec. 15, 2016, from application No. PCT/US2015/029292.
International Search Report and Written Opinion dated Oct. 15, 2016, from related application No. PCT/US2014/029292.
Japanese Office Action dated Feb. 6, 2018, from application No. 2016-569901.
Japanese Office Action dated Oct. 30, 2018, from application No. 2016-569901.
Non-final Office Action dated Oct. 30, 2018, from U.S. Appl. No. 15/310,198.
Notice of Allowance dated Jul. 3, 2019, from U.S. Appl. No. 15/310,198.
Chinese Office Action dated Apr. 28, 2020, from application No. 201810370663.0.
Extended European Search Report dated May 19, 2021, from application No. 20208042.0.

* cited by examiner

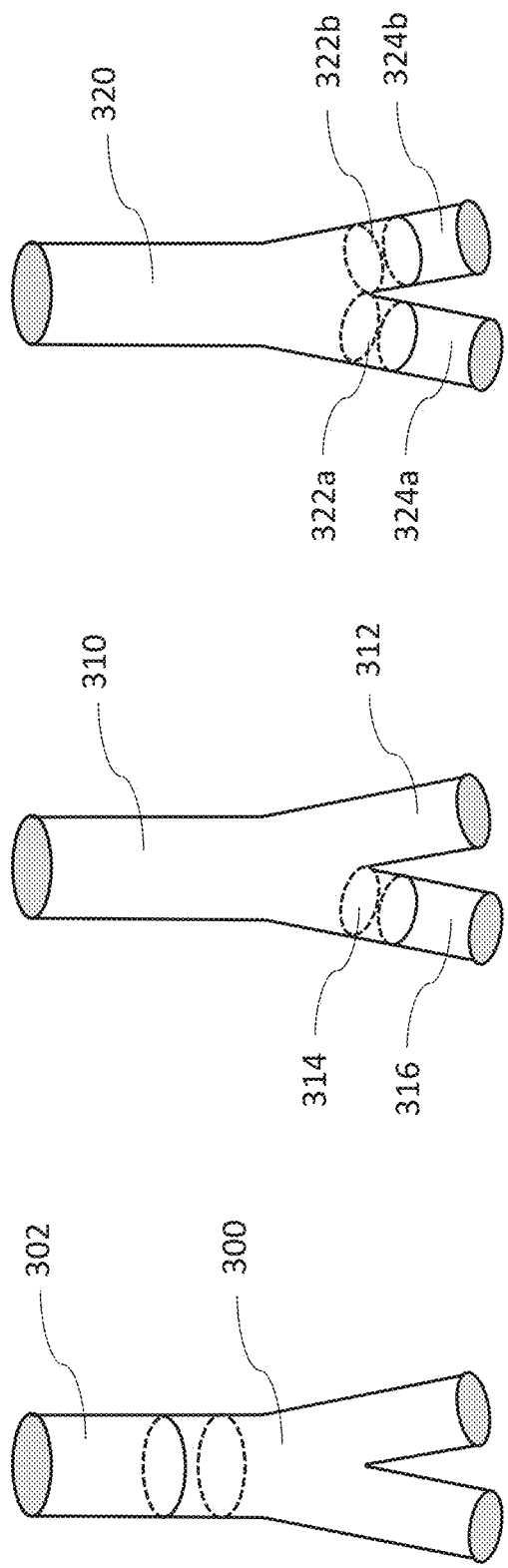

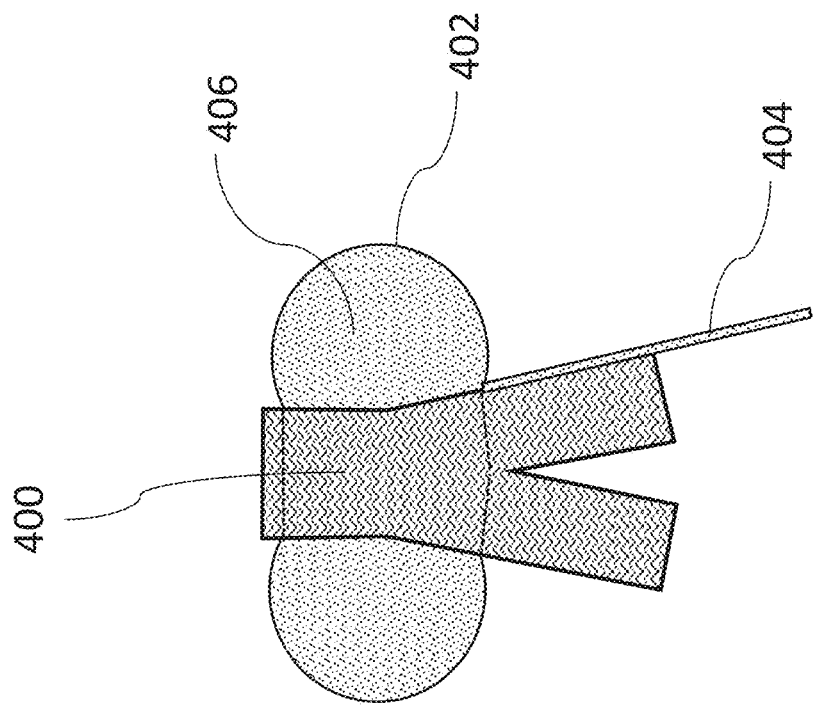
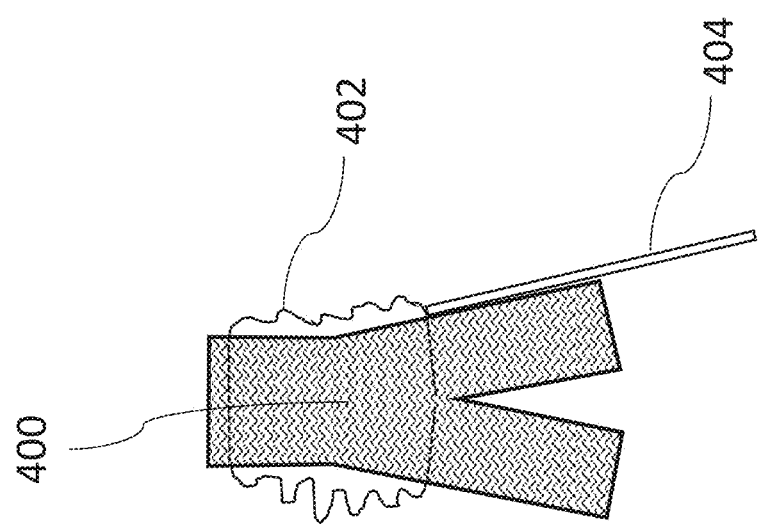
Fig. 4A
Fig. 4B

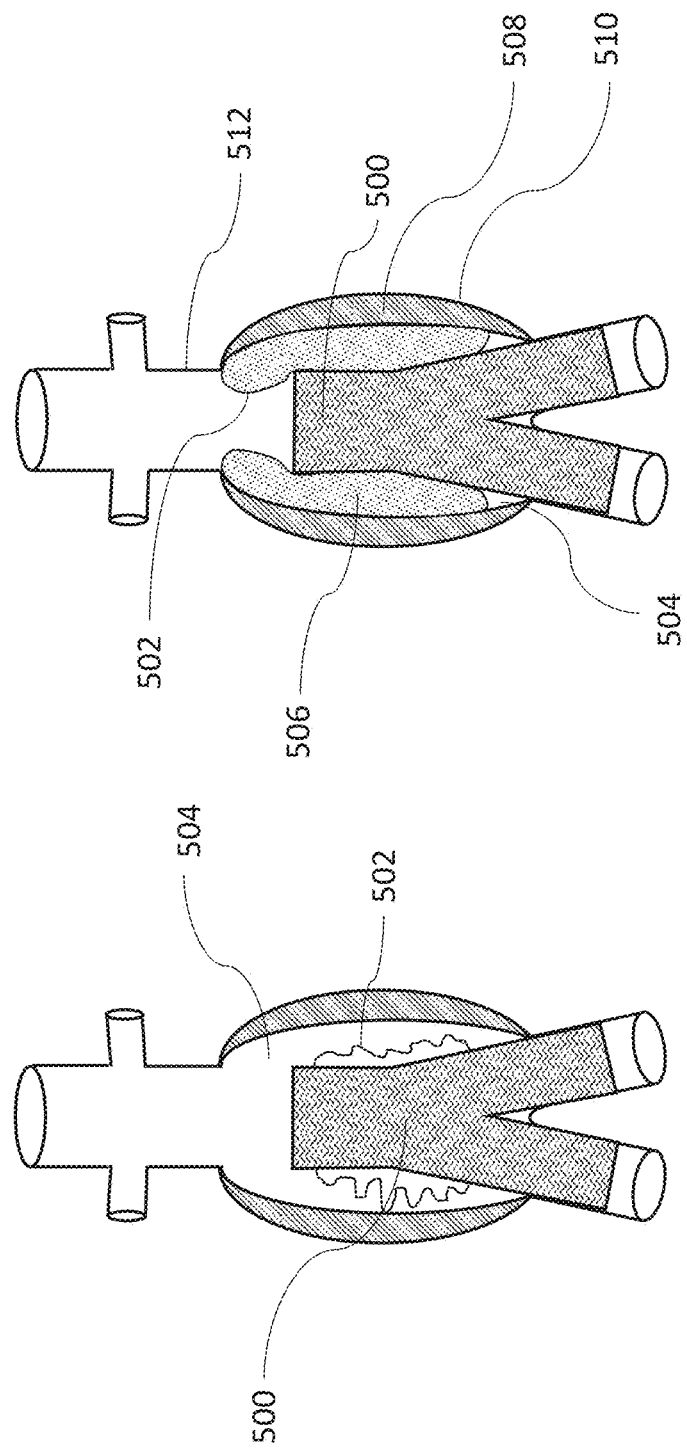

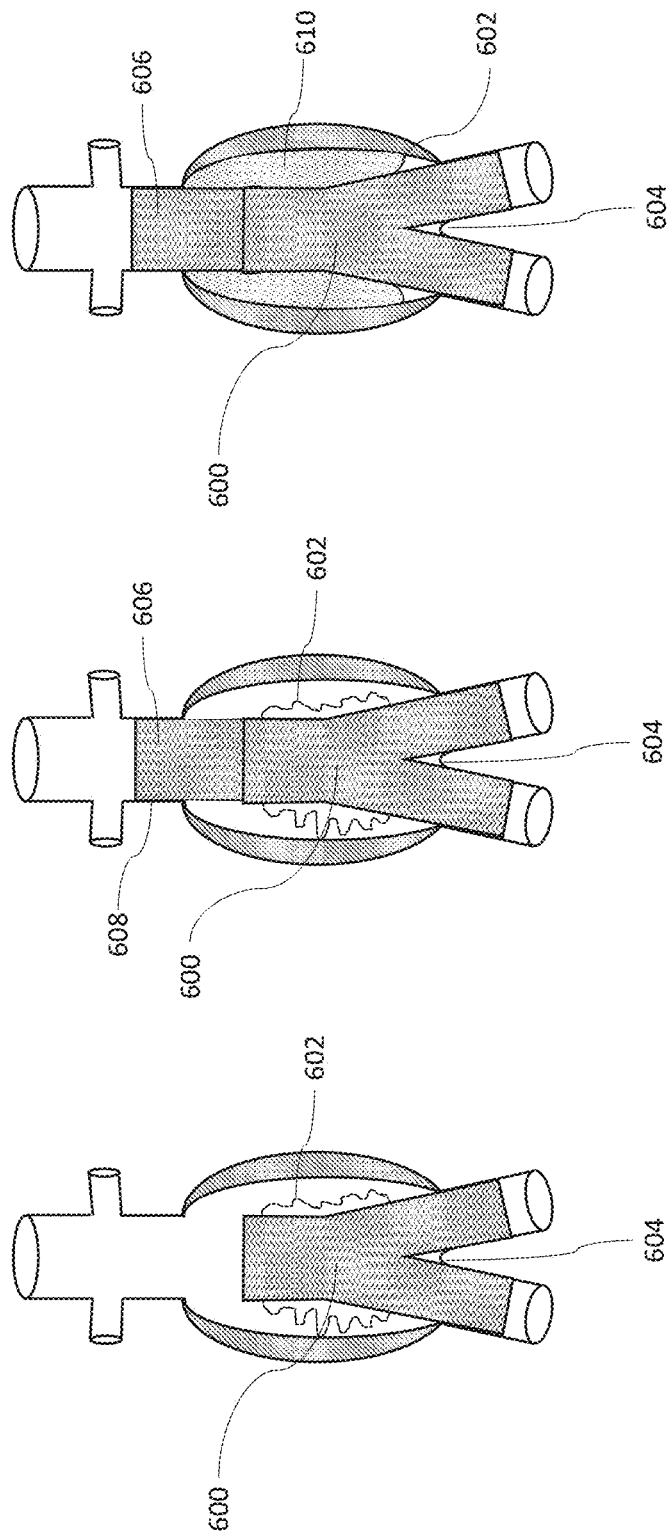

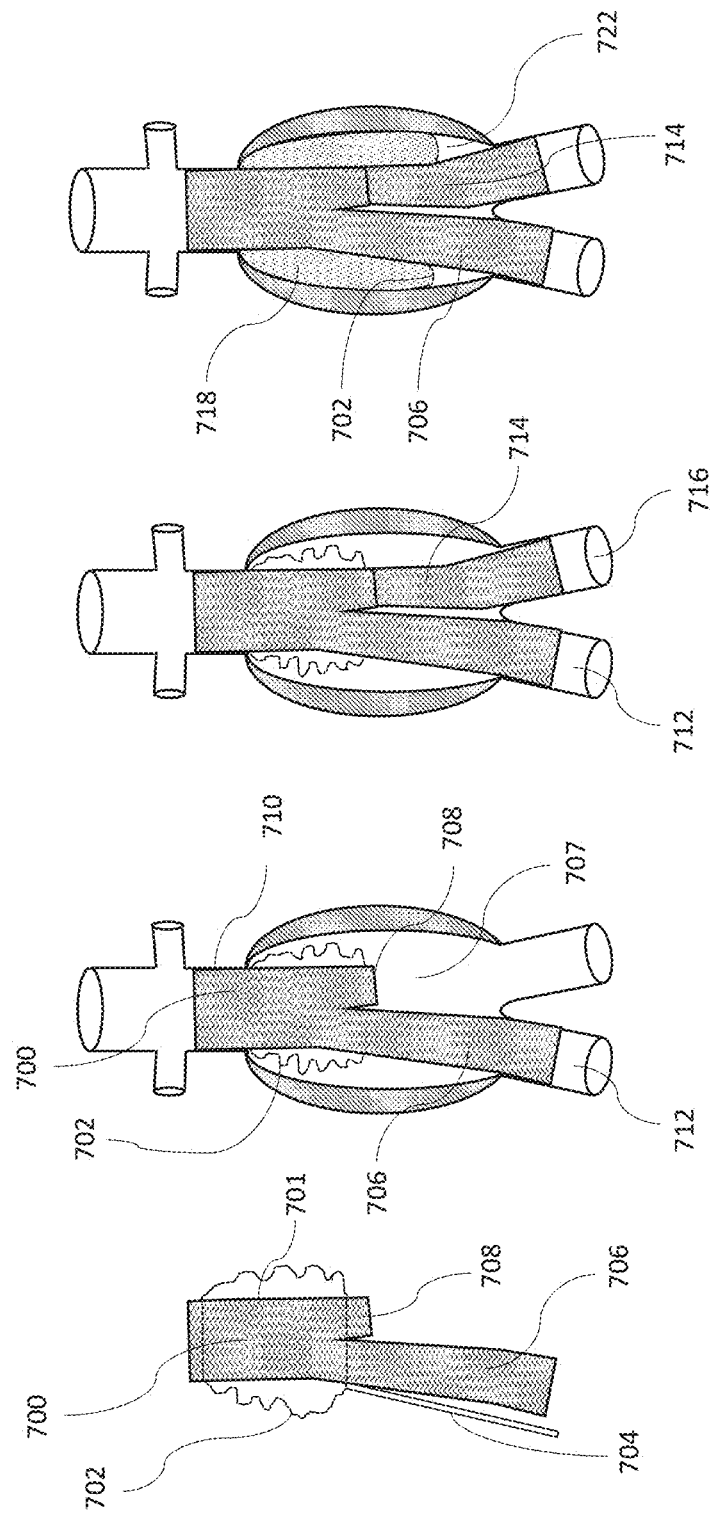

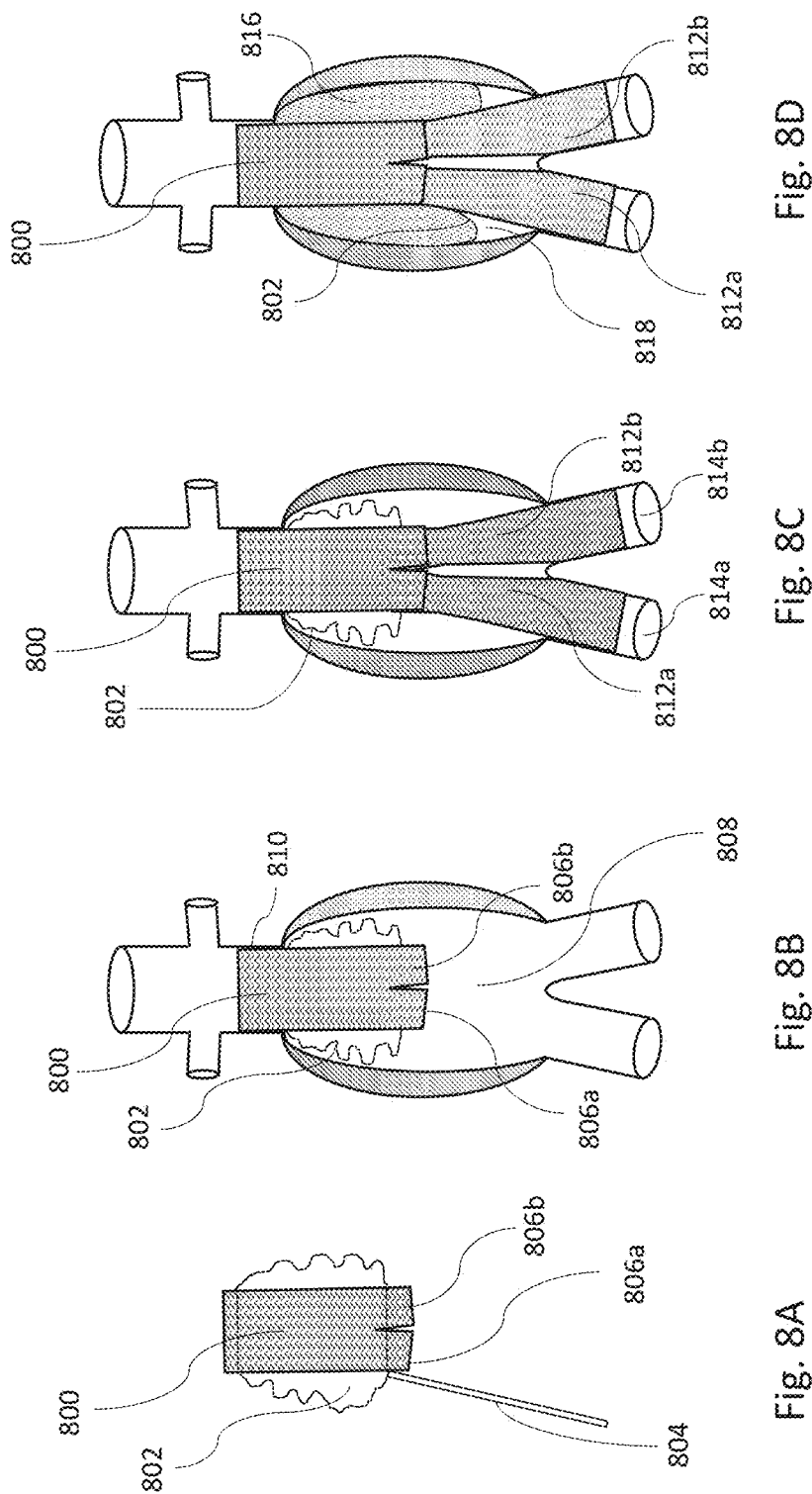

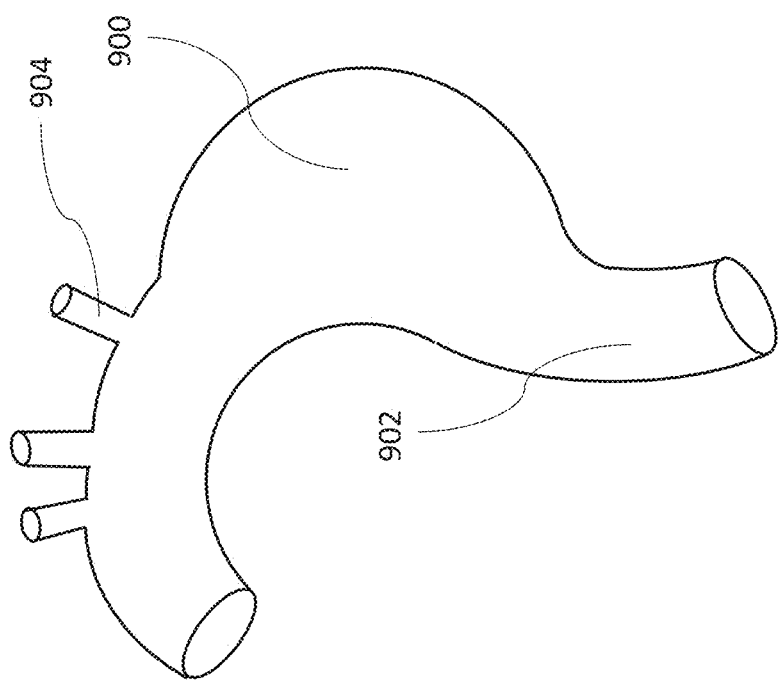

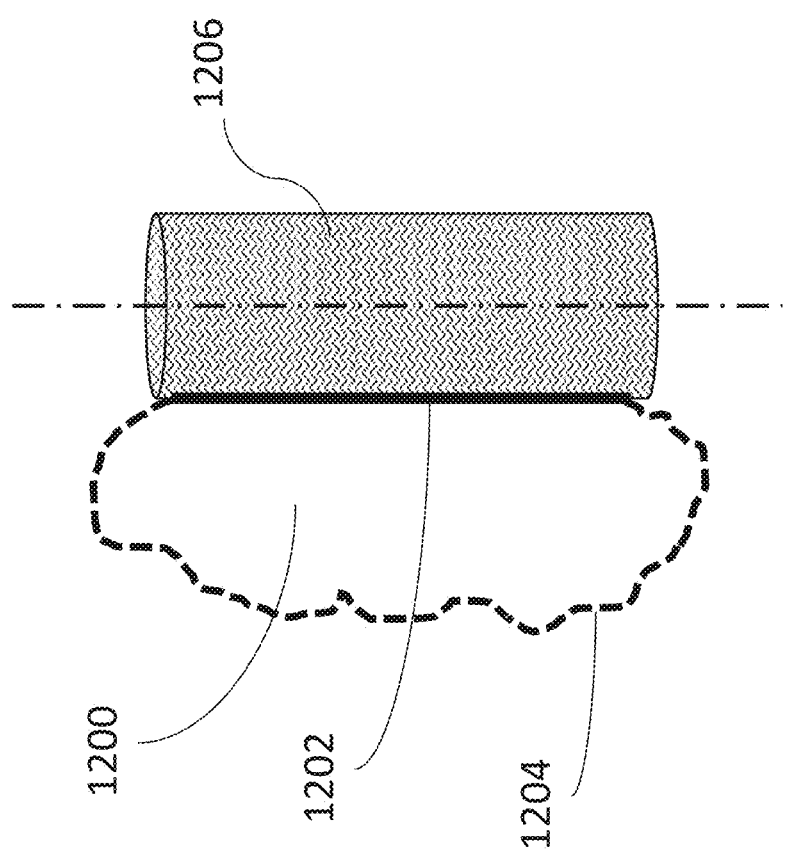

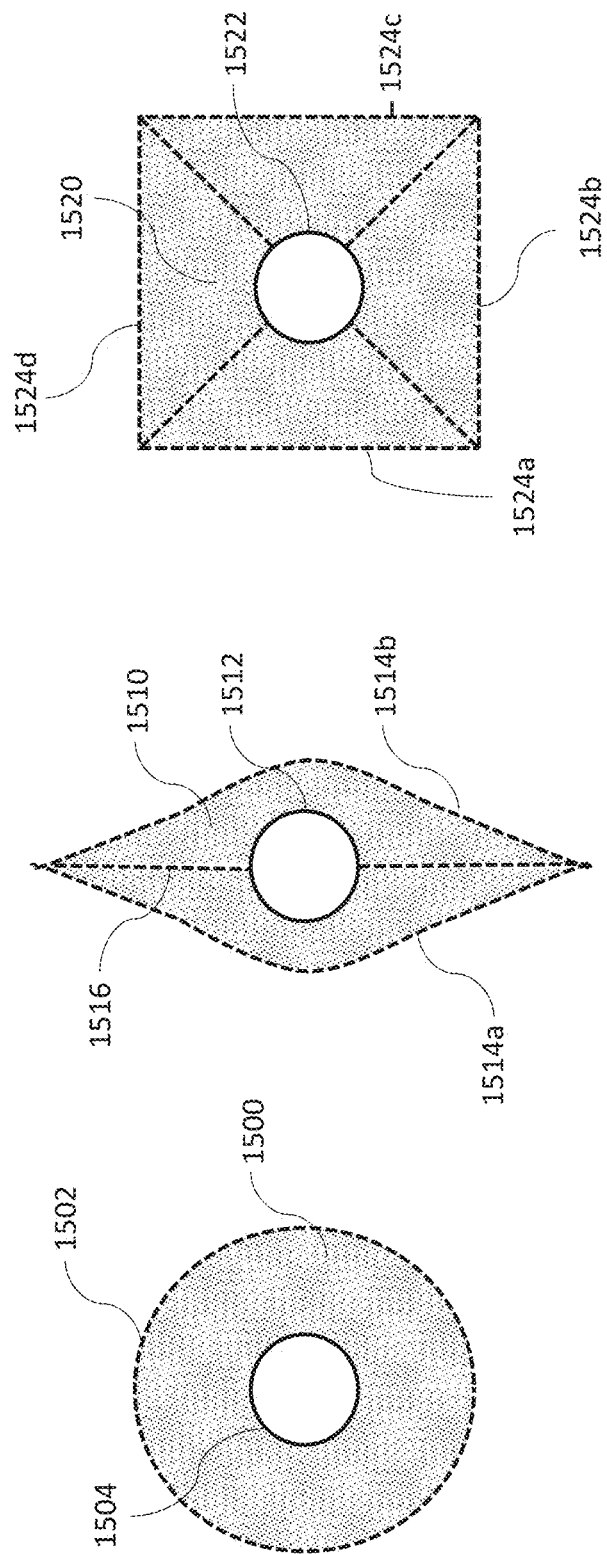

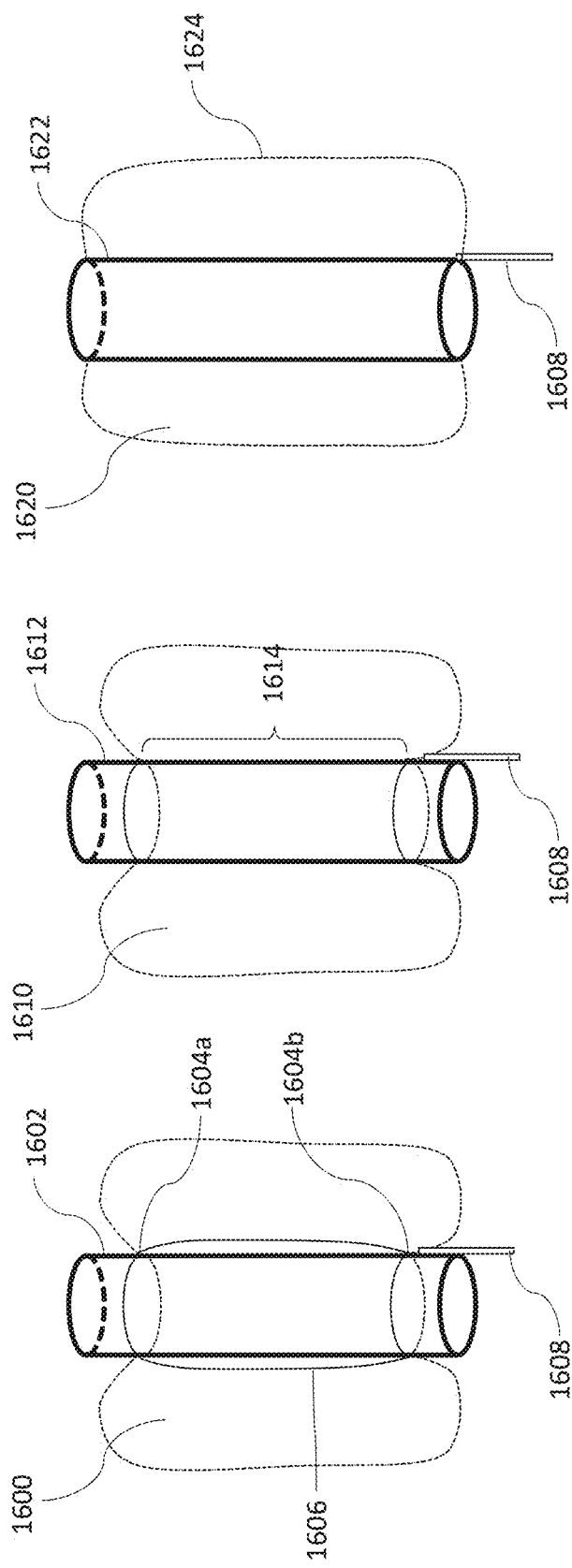

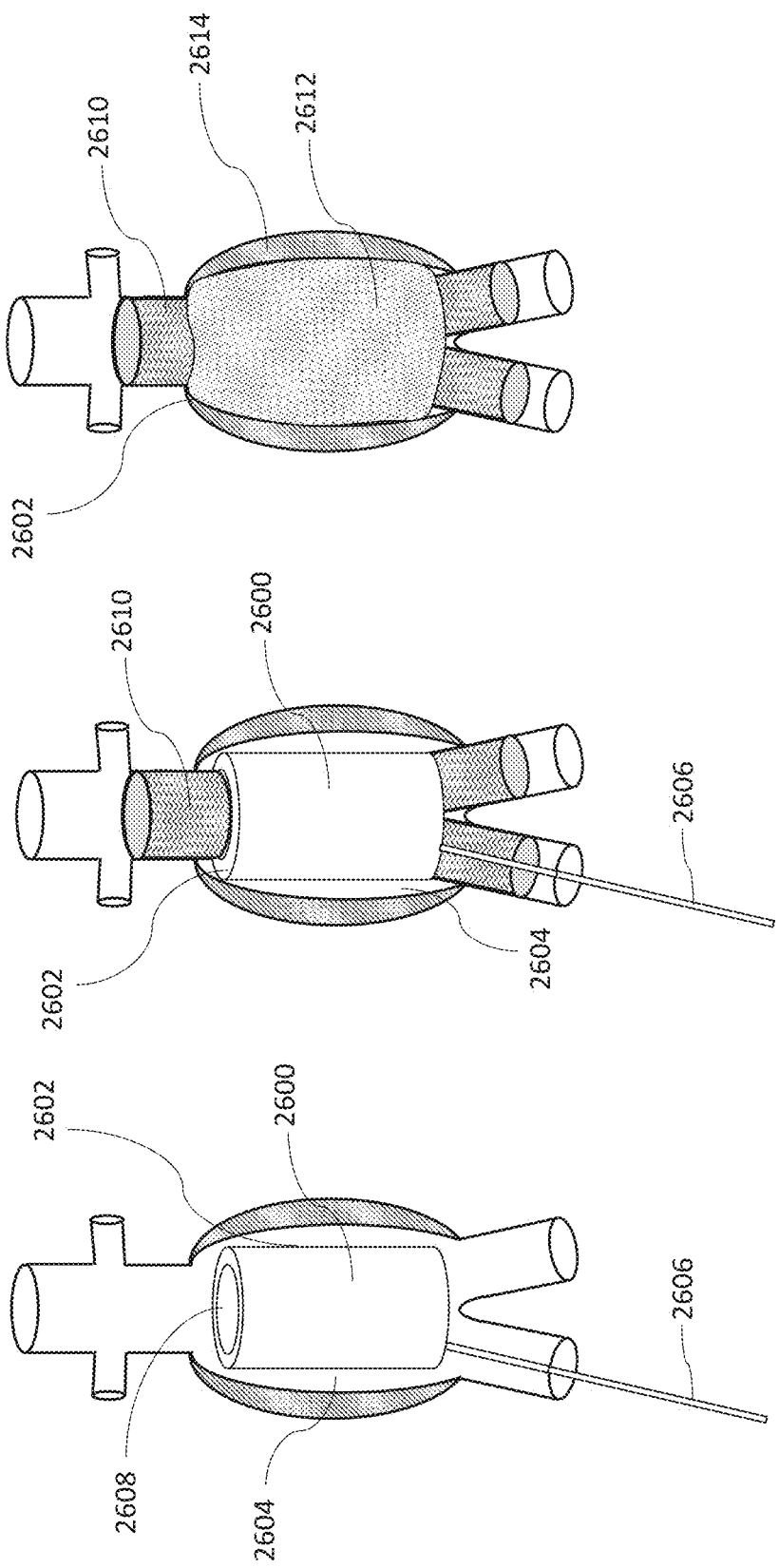

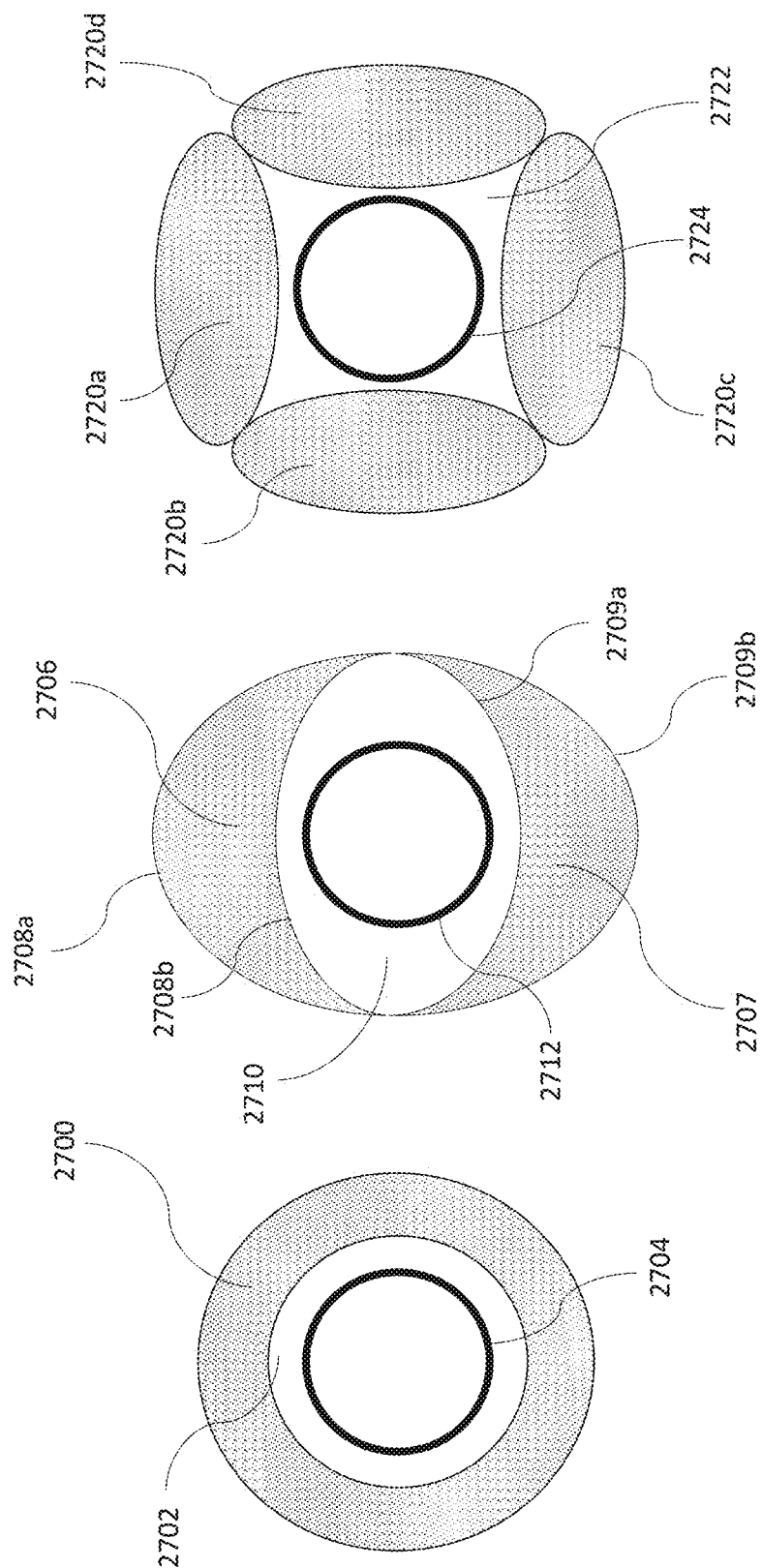

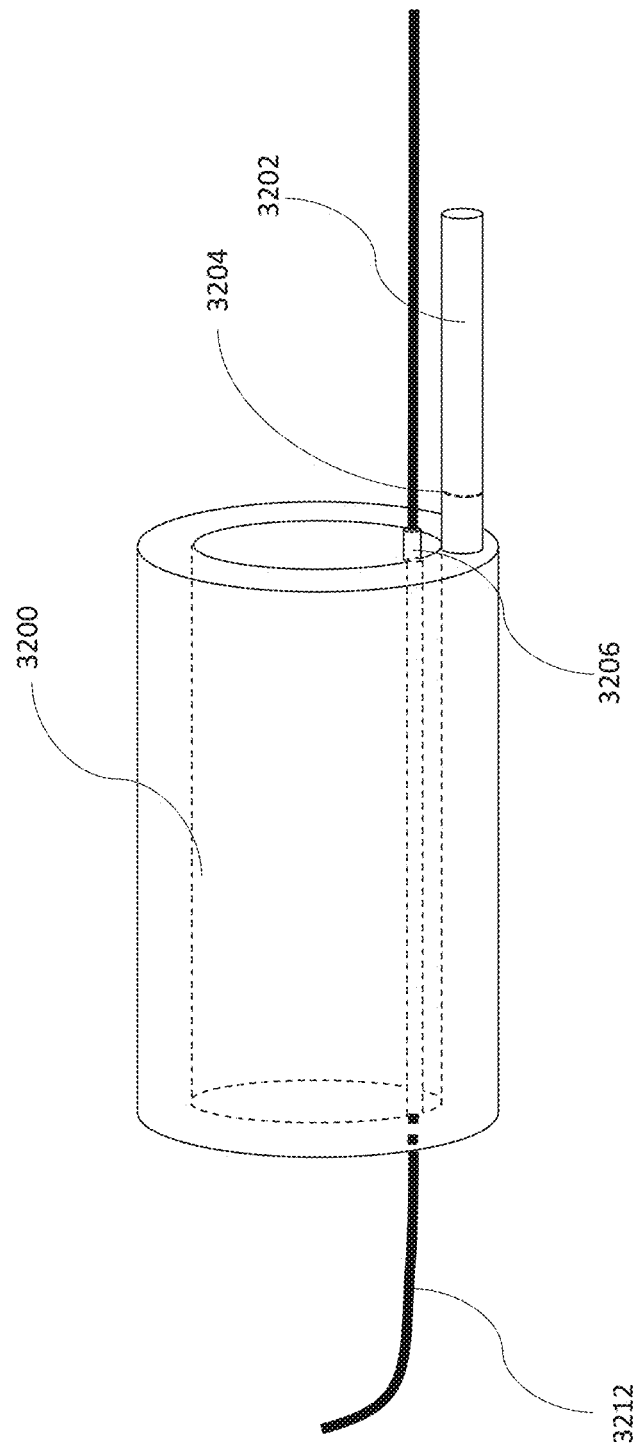

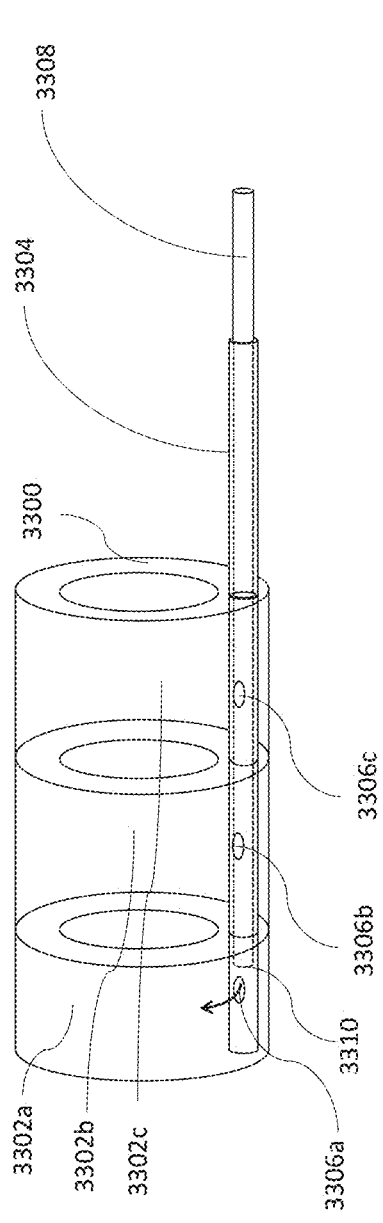
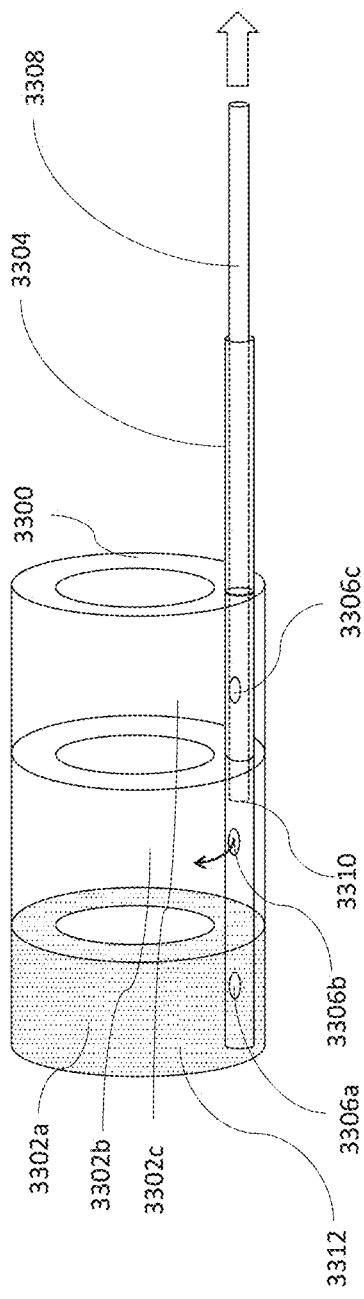

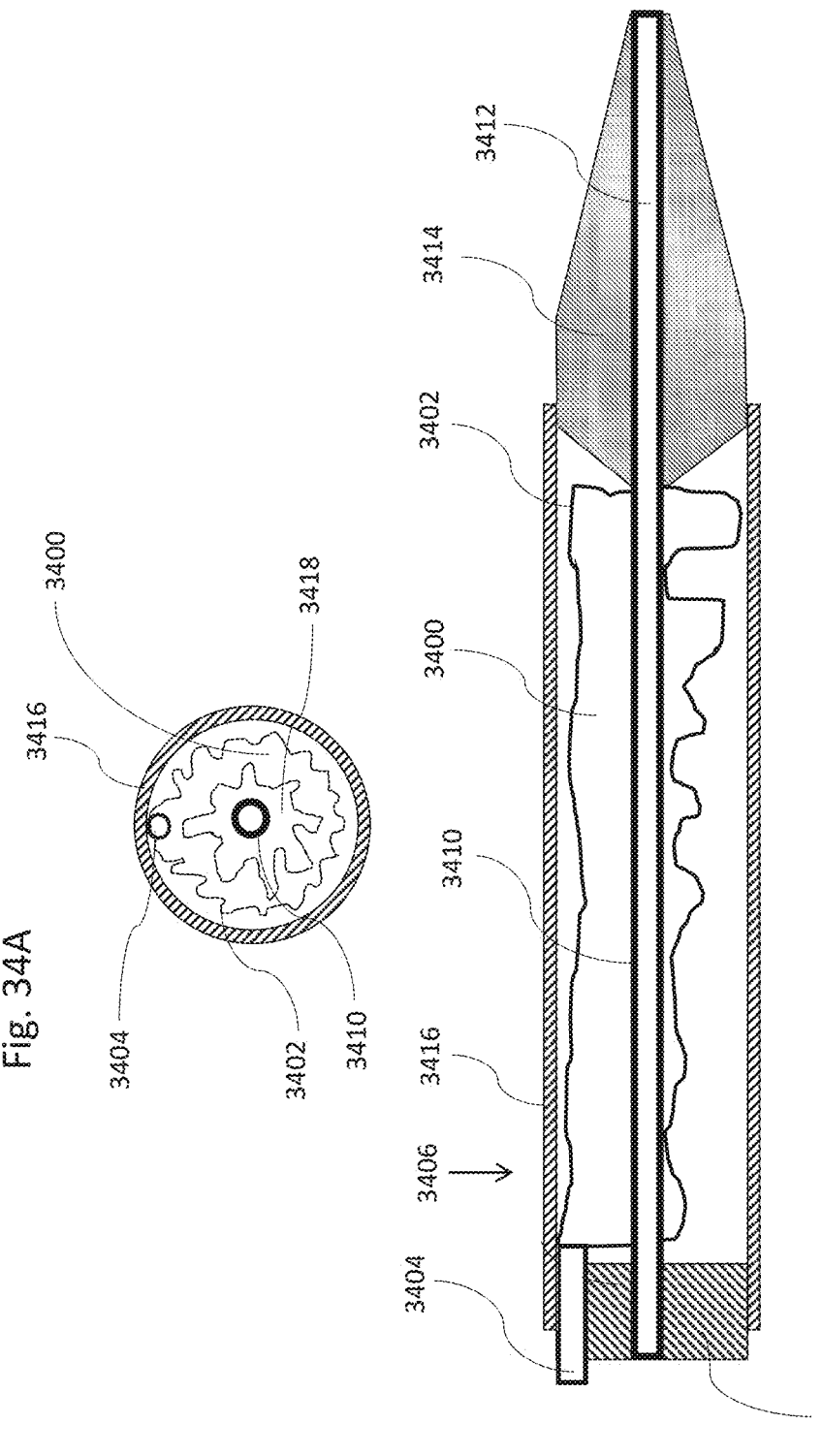

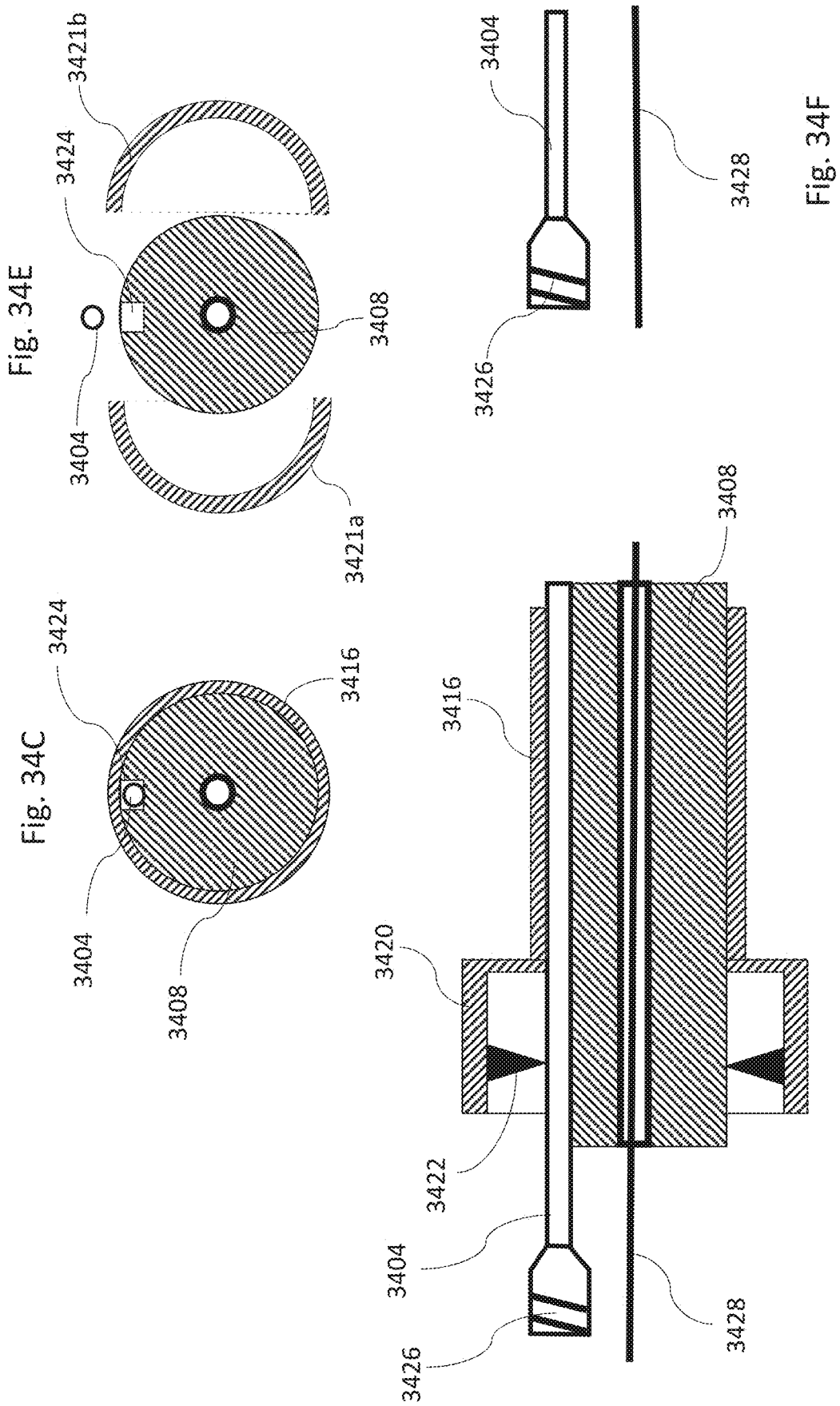

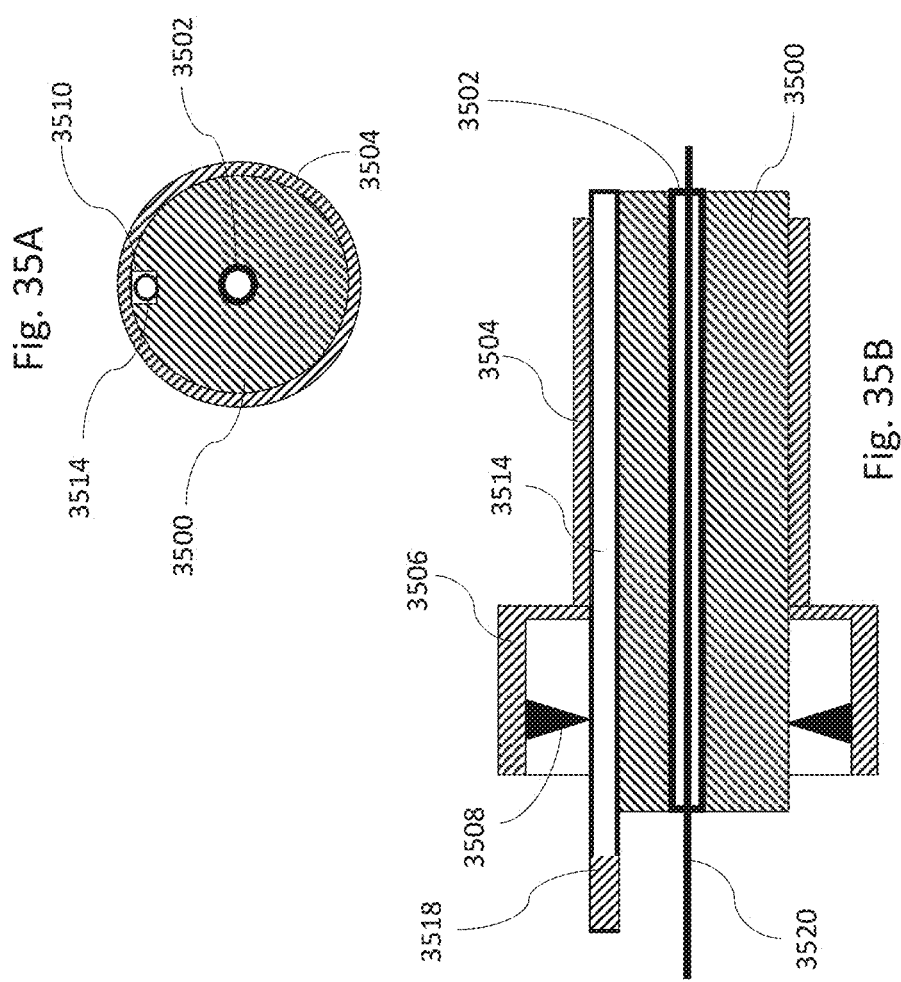

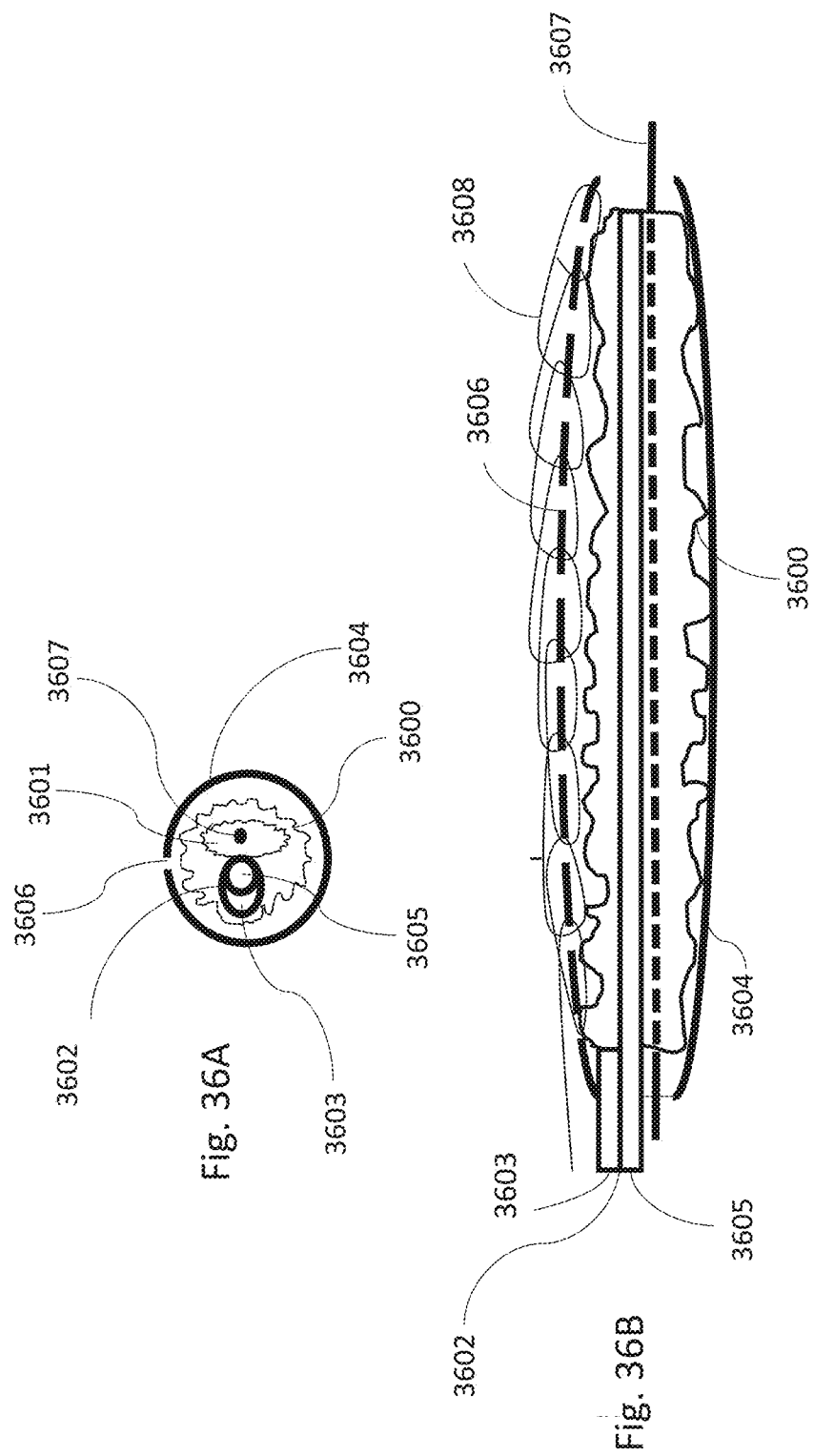

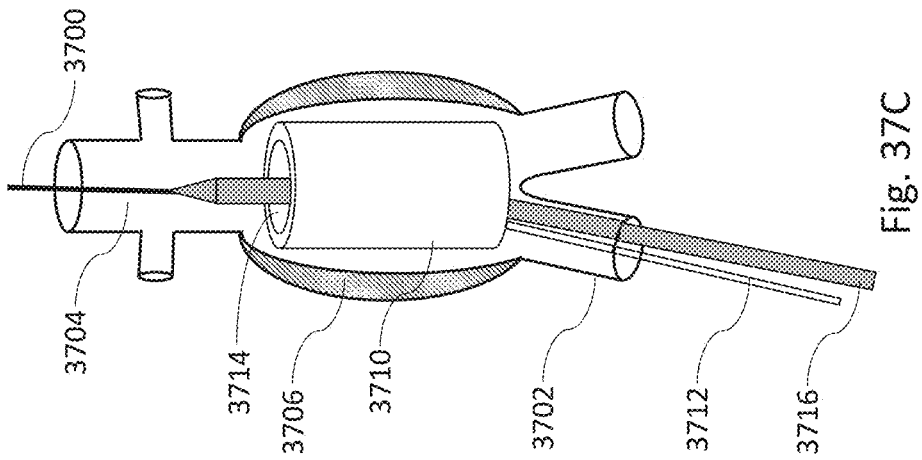
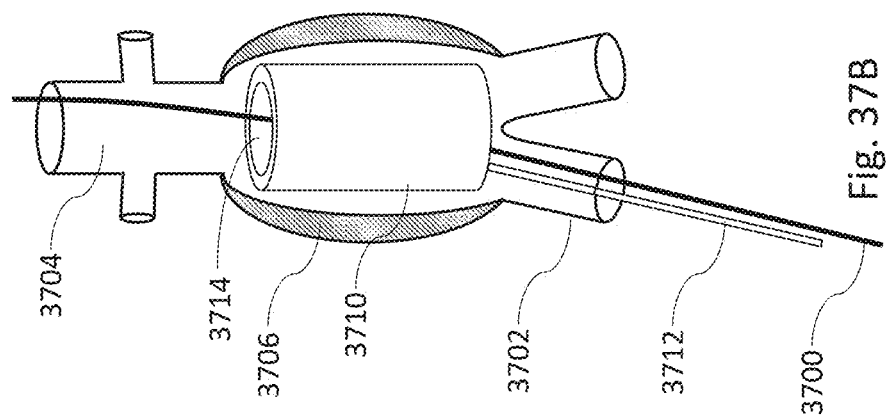
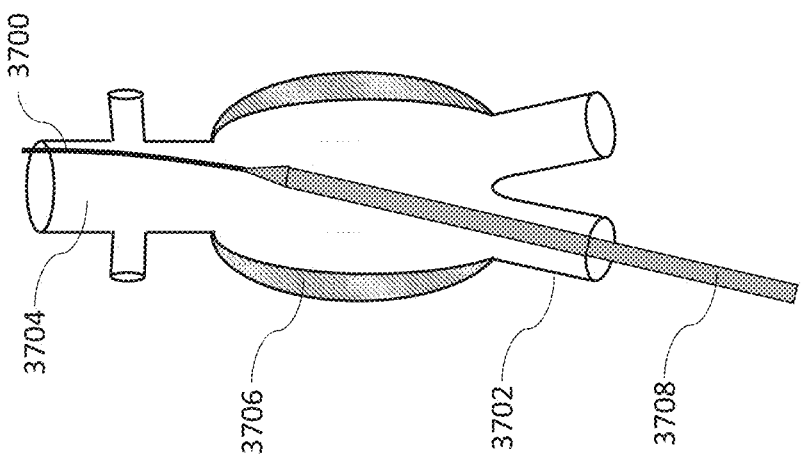

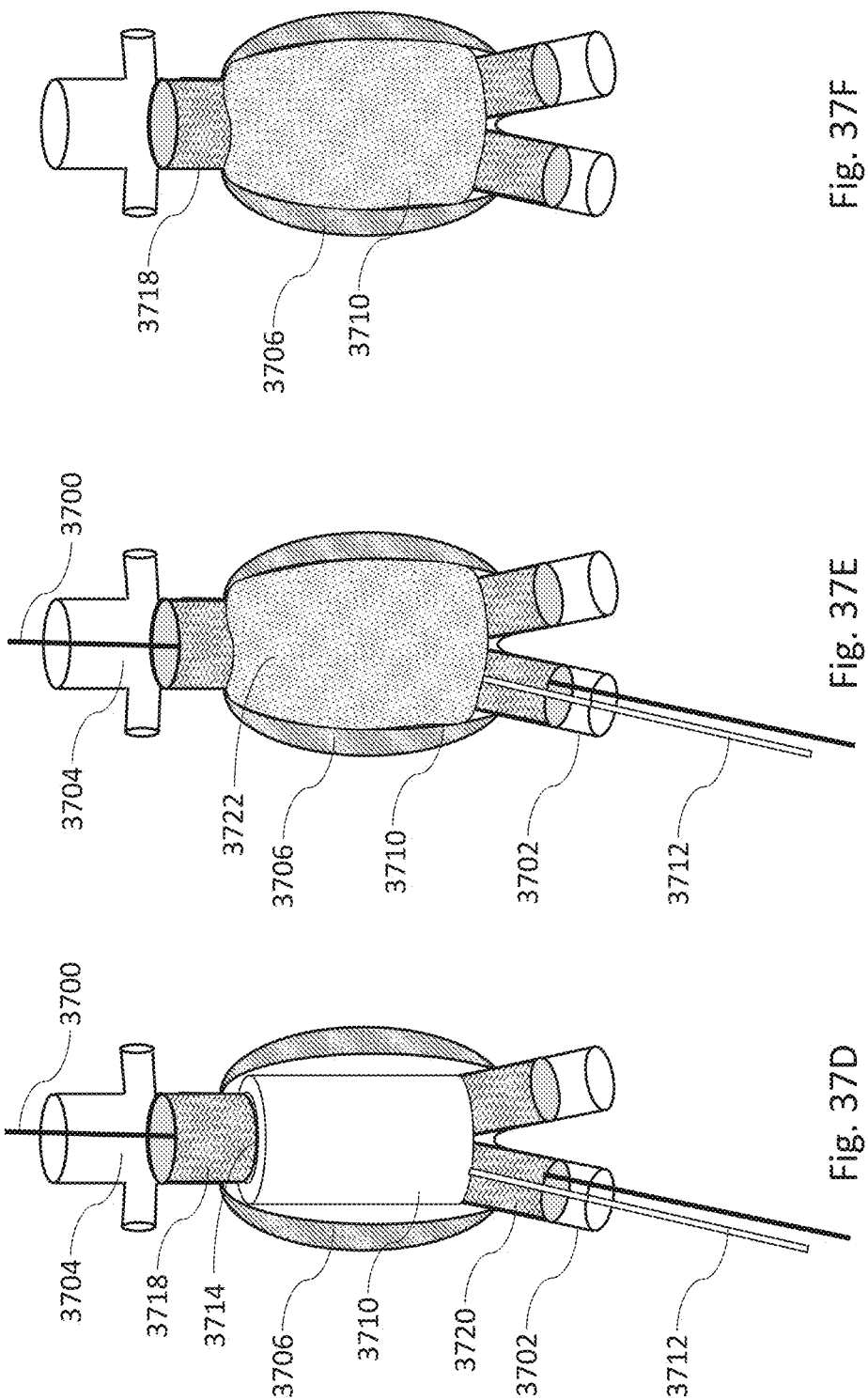

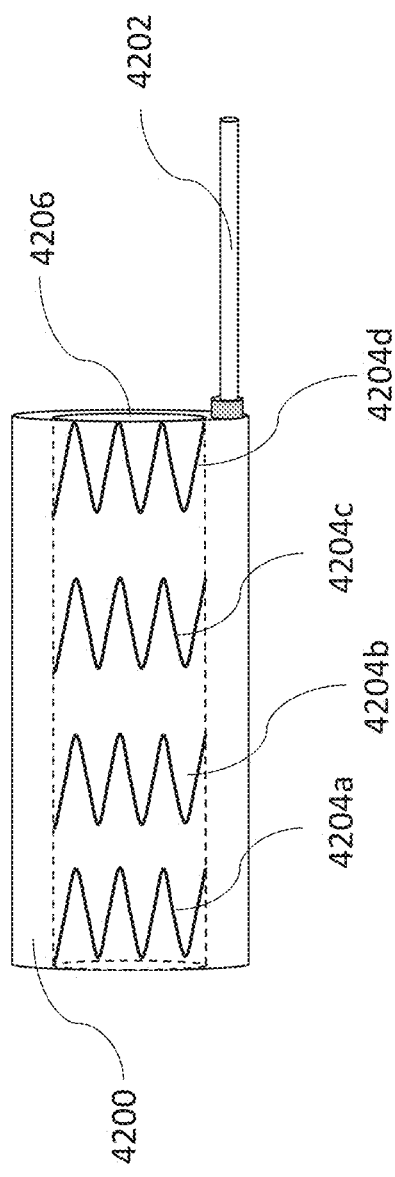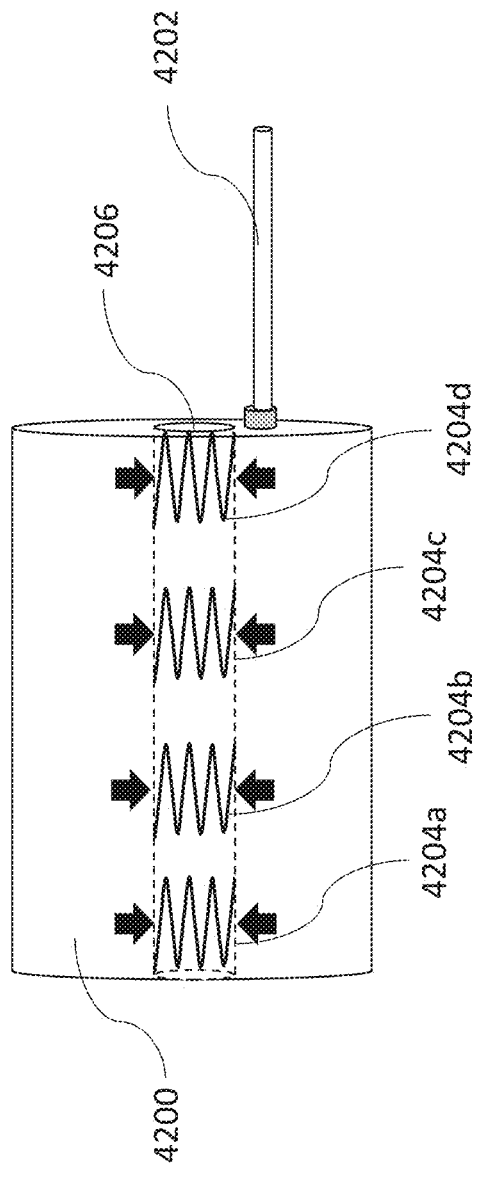
Fig. 42A
Fig. 42B

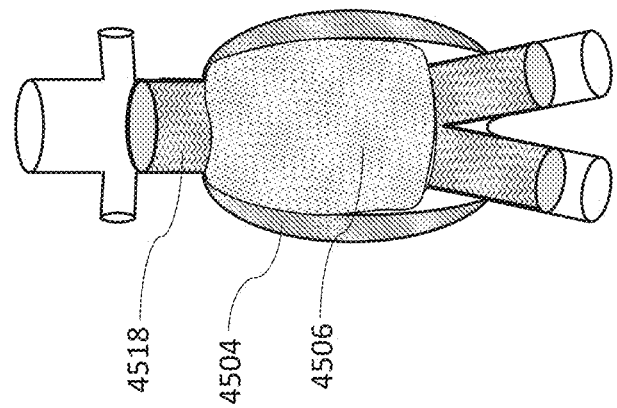
Fig. 45F
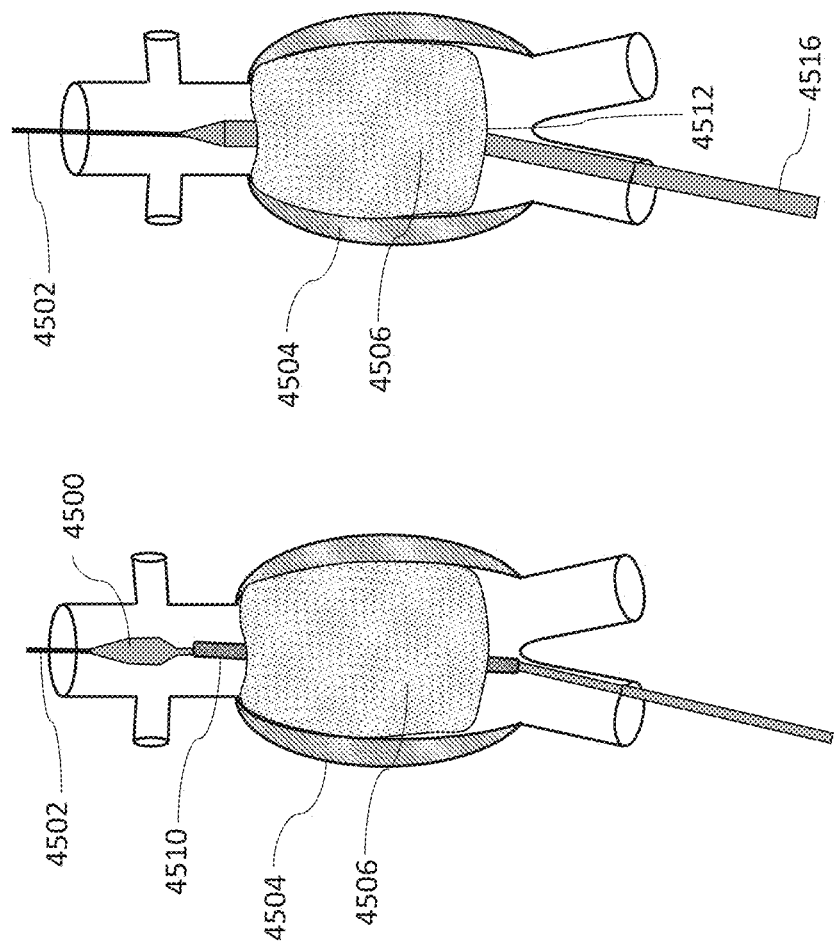
Fig. 45E
Fig. 45D

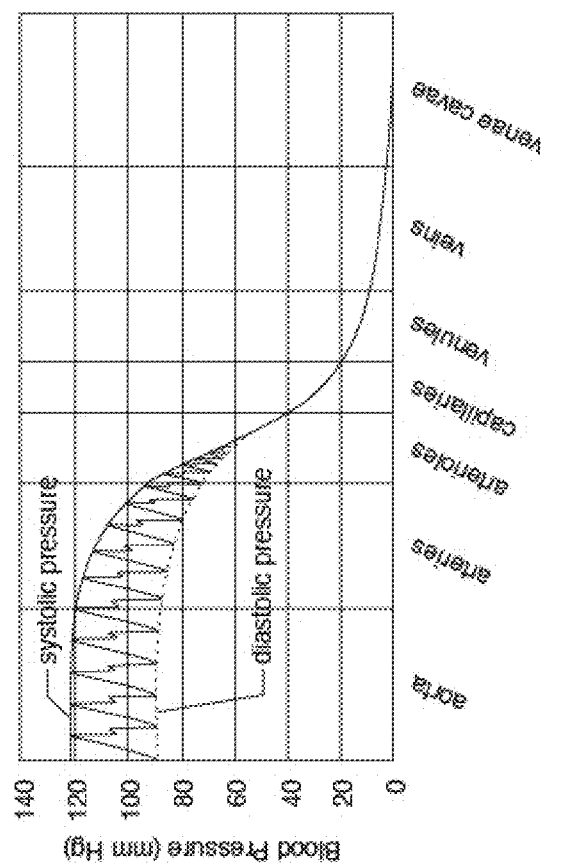

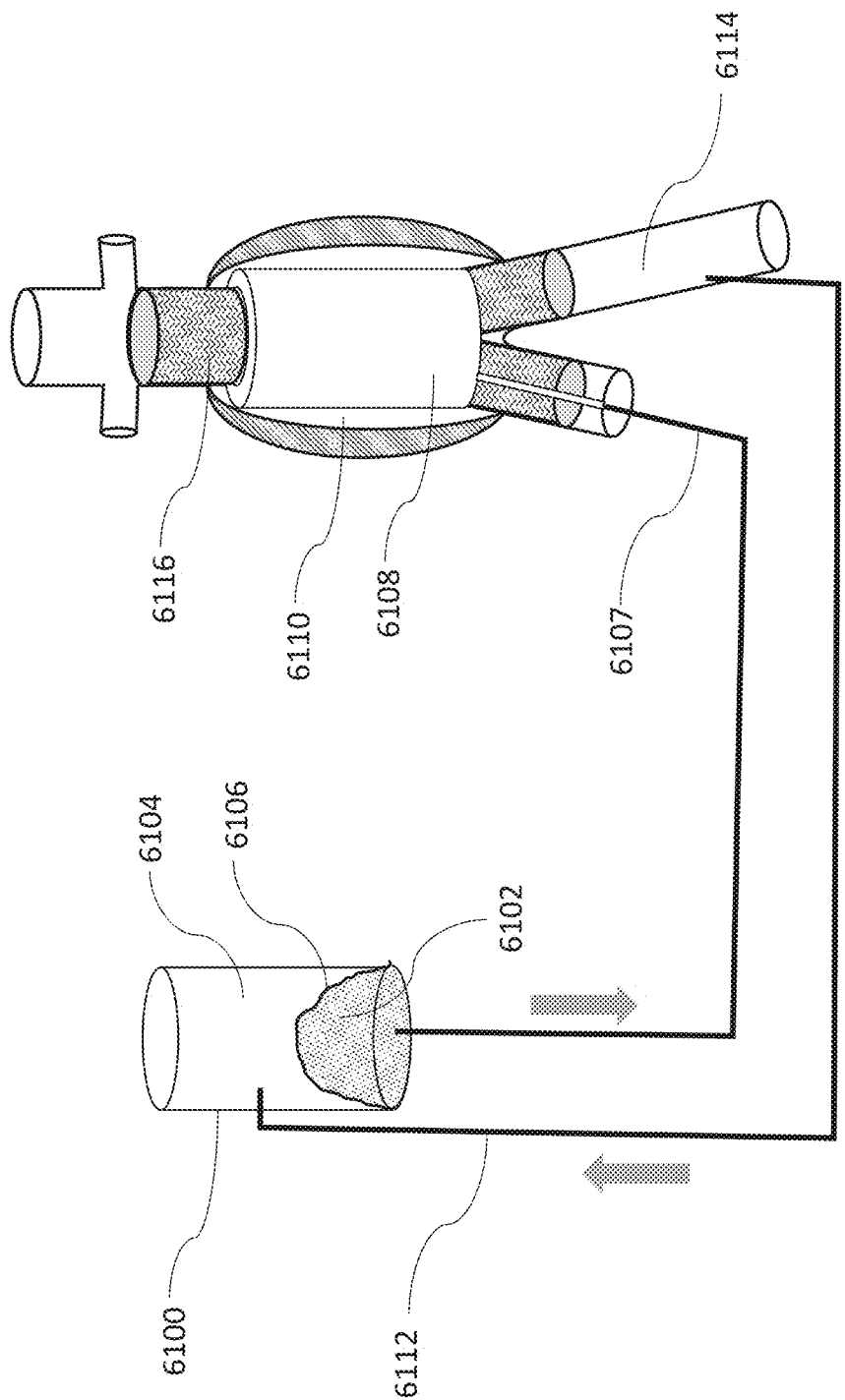

MODULAR STENT GRAFT SYSTEMS AND METHODS WITH INFLATABLE FILL STRUCTURES

CROSS-REFERENCE TO RELATED PATENT APPLICATIONS

This application is a continuation of U.S. application Ser. No. 15/310,198, filed Nov. 10, 2016, which is a national stage application under 35 U.S.C. § 371 of International Application No. PCT/US2015/029292, filed May 5, 2015, which claims priority from U.S. Provisional Patent App. Ser. No. 62/004,925, filed May 30, 2014, the entire contents of which are incorporated by reference herein.

FIELD

Embodiments described herein generally relate to systems including or used with stent grafts, and methods of using such systems, and in some embodiments to expandable stent graft systems and methods of using expandable stent graft systems for treating aneurysms.

BACKGROUND

Aneurysms are enlargements or bulges in blood vessels that are often prone to rupture and, therefore, may present a serious risk to a patient. Aneurysms may occur in any blood vessel and are of particular concern when they occur in the cerebral vasculature or the aorta.

There is some concern about aneurysms occurring in the aorta, particularly those referred to as aortic aneurysms. Abdominal aortic aneurysms (AAAs) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries, while thoracic aortic aneurysms (TAAs) occur in the ascending, transverse, or descending part of the upper aorta.

Infrarenal aneurysms are the most common, representing about 70% of all aortic aneurysms. Suprarenal aneurysms are less common, representing about 20% of the aortic aneurysms. Thoracic aortic aneurysms are the least common and often the most difficult to treat.

Among the macroscopic shape and size classifications is the most common form of aneurysm known as "fusiform," where the aortic wall enlargement compared to its normal diameter extends about the entire aortic circumference. Less common aneurysms may be characterized by a bulge on one side of the blood vessel attached at a narrow neck. Thoracic aortic aneurysms are often aortic wall dissecting aneurysms caused by hemorrhagic separation in the aortic wall, usually within its medial layer.

SUMMARY OF THE DISCLOSURE

An apparatus in accordance with various embodiments includes a first stent graft that is at least partially insertable into a first blood vessel. The first stent graft has a first end, a second end, an inside surface, and an outside surface. In some embodiments, the apparatus includes an inflatable fill structure fixed to a portion of the outside surface of the first stent graft. The inflatable fill structure includes an outer membrane that is configured to extend beyond the first end of the first stent graft when the inflatable fill structure is in a filled state.

Another apparatus in accordance with various embodiments includes a first stent graft that is at least partially insertable into a first blood vessel. The first stent graft has a first end, a second end, an inside surface, and an outside surface. The second end comprises a first leg and a second leg. The apparatus also includes an inflatable fill structure fixed to a portion of the outside surface of the first stent graft. The inflatable fill structure comprises an outer membrane that is configured to extend beyond an end of the first leg of the first stent graft when the inflatable fill structure is in a filled state.

Another apparatus in accordance with various embodiments includes a stent graft that is at least partially insertable into a blood vessel. The stent graft has a first end, a second end, an inside surface, and an outside surface. The apparatus further includes a first inflatable fill structure fixed to a first portion of the outside surface of the stent graft. The first inflatable fill structure comprises a first outer membrane. The apparatus also includes a second inflatable fill structure fixed to a second portion of the outside surface of the stent graft. The second inflatable fill structure comprises a second outer membrane.

Another apparatus in accordance with various embodiments includes a stent graft that is at least partially insertable into a blood vessel. The stent graft has a first end, a second end, an inside surface, and an outside surface. The stent graft is moveable between an unexpanded position and an expanded position. In some embodiments, the apparatus further includes an outer inflatable fill structure fixed to a first portion of the outside surface of the stent graft. The outer inflatable fill structure comprises a first outer membrane. The apparatus also includes a support inflatable fill structure. The stent graft is in the unexpanded position when the support inflatable fill structure is uninflated and the stent graft is in the expanded position when the support inflatable fill structure is filled.

Another apparatus in accordance with various embodiments includes a first stent graft that is at least partially insertable into a first blood vessel. The first stent graft has a first end, a second end, an inside surface, and an outside surface, and the first end comprises a first expandable structure configured to expand the first stent graft in a radial direction. The second end is configured to receive a first end of a second stent graft. In various embodiments, the apparatus further includes the second stent graft that is at least partially insertable into the first blood vessel. A first end of the second stent graft is at least partially insertable into the second end of the first stent graft. In some embodiments, the apparatus also includes an outer inflatable fill structure fixed to a portion of the outside surface of the first stent graft. The outer inflatable fill structure comprises an outer membrane that is configured to extend beyond the second end of the first stent graft and is configured to extend over the first end of the second stent graft when the first end of the second stent graft is inserted into the second end of the first stent graft and when the outer inflatable fill structure is in a filled state.

Another apparatus in accordance with various embodiments includes an inside membrane that defines a lumen along an axis, an outside membrane that surrounds the inside membrane, and a first end membrane fixed to a first end of the inside membrane along a circumference of the inside membrane and fixed to a first end of the outside membrane along a circumference of the outside membrane. The apparatus further includes a second end membrane fixed to a second end of the inside membrane along the circumference of the inside membrane and fixed to a second end of the outside membrane along the circumference of the outside membrane. The apparatus also includes a valve fixed to the second end membrane configured to allow a fill medium to flow into an inside space defined by the inside membrane, the outside membrane, the first end membrane, and the second end membrane. In some embodiments, the valve is configured to prevent the fill medium from flowing out of the inside space.

Another apparatus in accordance with various embodiments includes an inside membrane wrapped about an axis with a first end, a second end, a first side, and a second side opposite the first side and an outside membrane wrapped about the axis with a first end, a second end, a first side, and a second side opposite the first side. The first side of the inside membrane is fixed to the first side of the outside membrane and the second side of the inside membrane is fixed to the second side of the outside membrane. The apparatus further includes a valve configured to allow a fill medium to flow into an inside space defined by the inside membrane and the outside membrane and to not allow the fill medium to flow out of the inside space.

Another apparatus in accordance with various embodiments includes an inner core with a first end and a second end. The inner core comprises a guidewire lumen that is configured to extend between the first end of the inner core and the second end of the inner core and is configured to receive a guidewire. The inner core has an outer surface. The apparatus further includes a dilator tip fixed to the outer surface of the first end of the inner core. The dilator tip has a first end and a second end. The apparatus can also include a stent graft surrounding a portion of the outer surface of the inner core with a first end and a second end and an inflatable fill structure fixed to a portion of an outer surface of the stent graft. The inflatable fill structure is inflatable from an uninflated state to a filled state. When the inflatable fill structure is configured such that when it is in the filled state it extends beyond at least one of the first end of the stent graft or the second end of the stent graft.

Another apparatus in accordance with various embodiments includes an inner core with a first end and a second end. The inner core comprises a guidewire lumen that is configured to extend between the first end of the inner core and the second end of the inner core and is configured to receive a guidewire, and the inner core has an outer surface. The apparatus further includes a dilator tip fixed to the outer surface of the first end of the inner core. The dilator tip has a first end and a second end. The apparatus also includes an inflatable fill structure surrounding a portion of the inner core. The inflatable fill structure includes an inner membrane and an outer membrane. The inflatable fill structure also includes a fill tube fixed to an end of the inflatable fill structure. The inflatable fill structure is configured to be deployed within a blood vessel.

A method in accordance with various embodiments includes inserting a first delivery catheter into an aneurysm. The first delivery catheter comprises an inflatable fill structure. The method further includes deploying the inflatable fill structure in the aneurysm and inserting a second delivery catheter into the aneurysm. The second delivery catheter comprises a stent graft. The method also includes deploying the stent graft in the aneurysm and inflating the inflatable fill structure with a first fill medium.

Another method in accordance with various embodiments includes inserting a first delivery catheter into an aneurysm. The first delivery catheter comprises an inflatable fill structure and an inflatable balloon. The method includes filling the inflatable balloon with a first fill medium, filling the inflatable fill structure with a second fill medium to a first pressure within the inflatable fill structure, and removing at least a portion of the first fill medium from the inflatable balloon. The method also includes removing the inflatable balloon from the aneurysm, and inserting a second delivery catheter into the aneurysm, where the second delivery catheter includes a stent graft, and deploying the stent graft in the aneurysm.

Another method in accordance with various embodiments includes inserting a first delivery catheter into an aneurysm. The delivery catheter comprises a first stent graft and an inflatable fill structure fixed to a portion of an outside surface of the first stent graft. The first stent graft has a first end and a second end. The method includes deploying the first stent graft in the aneurysm and filling the inflatable fill structure with a fill medium. A portion of the inflatable fill structure is configured to extend beyond at least one of the first end of the first stent graft or the second end of the first stent graft when the inflatable fill structure is in a filled state.

Another method in accordance with various embodiments includes inserting a delivery catheter into an aneurysm. The delivery catheter includes an inflatable filing structure. The inflatable fill structure has an inside surface. The method includes deploying the inflatable fill structure into the aneurysm, filling the inflatable fill structure with a fill medium to a first pressure, and monitoring movement of the inside surface of the inflatable fill structure.

Another method in accordance with various embodiments includes inserting a delivery catheter into an aneurysm. The delivery catheter includes a stent graft with a first end, a second end, a center section, an outer inflatable fill structure fixed to an outside surface of the center section of the stent graft, a sealing inflatable fill structure fixed to the first end of the stent graft, and a support inflatable fill structure fixed to a center section of the stent graft. The outer inflatable fill structure is configured to occupy a space of an aneurysm in a filled state. The sealing inflatable fill structure is configured to provide a seal between the first end of the stent graft and a wall of a first blood vessel when in a filled state. The support inflatable fill structure is configured to expand in a radial direction upon being filled with a first fill material. The method includes filling the support inflatable fill structure with the first fill material to a first pressure, filling the sealing inflatable fill structure with a second fill material to a second pressure, and filling the outer inflatable fill structure with a third fill material to a third pressure.

BRIEF DESCRIPTION OF THE DRAWINGS

FIGS. 3A, 3B, and 3C are illustrations of modular bifurcated stent grafts.

FIGS. 4A and 4B are illustrations of a bifurcated stent graft with a deflated and a filled inflatable fill structure, respectively.

FIGS. 5A and 5B are illustrations of a bifurcated stent graft with an inflatable fill structure placed in an infrarenal aortic aneurysm, showing uninflated and filled states of the inflatable fill structure, respectively, in accordance with an illustrative embodiment.

FIGS. 6A, 6B, and 6C are illustrations showing some steps during deployment of a stent graft system, in accordance with an illustrative embodiment.

FIGS. 7A, 7B, 7C, and 7D are illustrations showing some steps of deployment of a stent graft system, in accordance with an illustrative embodiment.

FIGS. 8A, 8B, 8C, and 8D are illustrations showing some steps of deployment of a stent graft system, in accordance with an illustrative embodiment.

FIG. 9 is an illustration of a thoracic aortic aneurysm.

FIG. 12 is an illustration of an inner wall and an outer wall of an inflatable fill structure in close proximity to a tubular graft, in accordance with an illustrative embodiment.

FIGS. 15A, 15B, and 15C are cross sectional illustrations of exemplary inflatable fill structures, in accordance with some illustrative embodiments.

FIGS. 16A, 16B, and 16C are illustrations of connections between a graft and an inner wall of an inflatable fill structure, in accordance with some illustrative embodiments.

FIGS. 26A, 26B, and 26C are illustrations showing some steps during placement and inflation of an aneurysm fill system in an infrarenal aneurysm, in accordance with an illustrative embodiment.

FIGS. 27A, 27B, 27C, 27D, and 27E are cross-sectional illustrations of example inflation compartments of an aneurysm fill systems, in accordance with some illustrative embodiments.

FIG. 32 is an illustration of an aneurysm fill system with a separate guidewire lumen and fill tube, in accordance with an illustrative embodiment.

FIGS. 33A and 33B are illustrations of a multi-compartment aneurysm fill system, in accordance with an illustrative embodiment.

FIGS. 34A, 34B, 34C, 34D, 34E, and 34F are illustrations of the distal end of a delivery catheter in accordance with an illustrative embodiment.

FIGS. 35A, 35B, and 35C are illustrations of the distal end of a delivery catheter in accordance with an illustrative embodiment.

FIGS. 36A and 36B are illustrations of a delivery catheter housing of an aneurysm fill system, in accordance with an illustrative embodiment.

FIGS. 37A, 37B, 37C, 37D, 37E, and 37F are illustrations showing some steps during implantation of an aneurysm fill system, in accordance with an illustrative embodiment.

FIGS. 42A and 42B are illustrations of an aneurysm fill system with a self-expanding stent, in accordance with an illustrative embodiment.

FIGS. 45A, 45B, 45C, 45D, 45E, and 45F are illustrations showing some steps during implantation of an aneurysm fill system with an inflatable balloon, in accordance with an illustrative embodiment.

FIG. 60 is a plot of relative nominal blood pressure in substructures of a circulatory system.

FIG. 61 is a diagram showing a reservoir system in communication with a contained space of a fill system in an aneurysm, in accordance with an illustrative embodiment.

DETAILED DESCRIPTION

Figure 2:
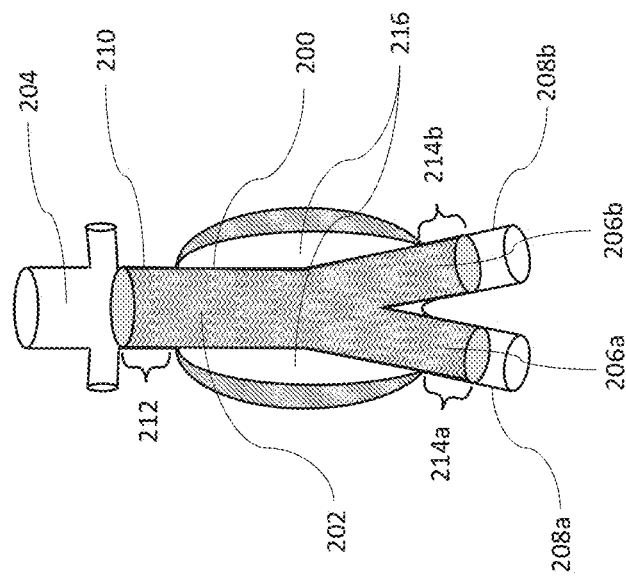
FIG. 2 is an illustration of a bifurcated stent graft placed across an infrarenal aortic aneurysm.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 1:
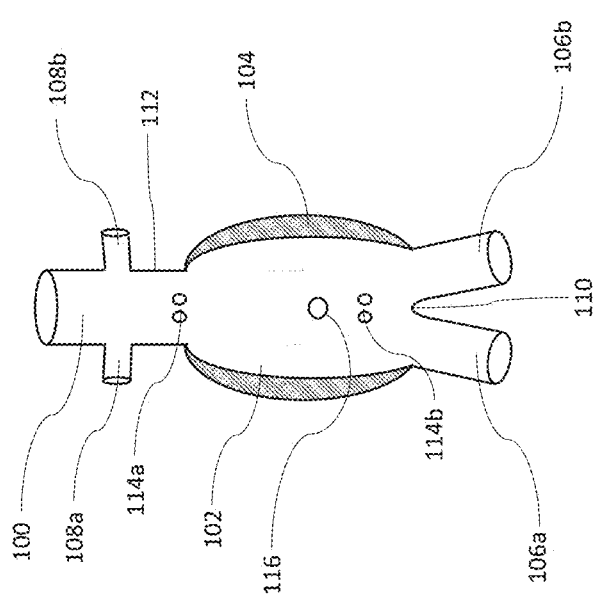
FIG. 1 is an illustration of a cross section of the anatomy of an infrarenal aortic aneurysm, in accordance with an illustrative embodiment.

FIG. 1 is an illustration of a cross section of the anatomy of an infrarenal aortic aneurysm. The aorta 100 branches at the aortic bifurcation 110 into two iliac arteries 106a and 106b. The aneurysm sac 102 denotes a bulged section of the aorta. As the name implies, the infrarenal aortic aneurysm is located below the renal arteries 108a and 108b. A segment of the aorta between the renal arteries 108a and 108b and the aneurysm sac 102 is referred to as the proximal neck 112. Often mural thrombus 104 forms on an inside wall of the aneurysm. A diameter of a flow lumen in the aneurysm is, thus, reduced by the mural thrombus 104 to a diameter less than a diameter of the aneurysm sac 102. Within the infrarenal aneurysm are arterial branch vessels that perfuse the spine and organs adjacent to the aorta 100. Typically, several pairs of lumbar arteries 114a and 114b and the inferior mesenteric artery 116 are located within the infrarenal aortic aneurysm.

The dimensions of aortic aneurysm can vary greatly from patient to patient. The diameter of the proximal neck 112 may vary, for example, from 18 millimeters (mm) to 34 mm. The distance from the aortic bifurcation 110 to the renal arteries 108a and 108b may vary, for example, from 80 mm to 160 mm. The diameters of the right and left iliac arteries 106a and 106b might not be the same. The diameters of the iliac arteries 106a and 106b may vary, for example, from 8 mm to 20 mm. One iliac artery or both iliac arteries may be aneurysmal with greatly enlarged diameters, for example, of more than 30 mm.

FIG. 2 is an illustration of a bifurcated stent graft 200 placed across an infrarenal aortic aneurysm 216, to exclude the aneurysm 216 from aortic blood pressure. The bifurcated stent graft 200 includes a main body 202 which can be placed in an aorta 204 and two legs 206a and 206b extending from the main body 202 into iliac arteries 208a and 208b. The proximal end of the main body 202 can expand against a wall of the aorta 204 at a proximal neck 210 and can create a proximal seal 212. The distal ends of the two legs 206a and 206b can expand against walls of the iliac arteries 208a and 208b, respectively, to form distal seals 214a and 214b, respectively, in the distal seal zone adjacent thereto. After exclusion of the aneurysm 216 by the stent graft 200 from the aortic blood flow, a residual aneurysm sac volume remains external to the stent graft 200. The blood in the aneurysm sac can thrombose over time. The thrombus can be reabsorbed by the body resulting in aneurysm sac shrinkage. In some cases, the lumbar arteries and the inferior mesenteric artery can continue to perfuse and pressurize the aneurysm sac. The flows from these branch vessels into the aneurysm sac are referred to as Type II endoleaks. Type II endoleaks may cause continuous sac enlargement over time and potentially rupture of the aneurysm 216. Infrarenal aortic aneurysm repair is discussed in greater detail below with respect to some embodiments, but the systems, devices, methods, and techniques discussed herein with regard to infrarenal aortic aneurysms are not meant to be limited to just that type of aneurysm. Various embodiments of systems, devices, methods, and techniques discussed herein can be adapted to repair any type of aneurysm.

Given the large variability in the dimensions of aortic aneurysms, a large number of traditional bifurcated stent grafts can be required to treat a wide range of patients and still maximize the seal length in the proximal neck and the iliac arteries. Therefore, it can be advantageous to use a "modular" stent graft system that can have several components that can be assembled in the body. The diameter and length of the individual components can be tailored, for example, to the dimensions of the aneurysm, the aorta, and/or the iliac arteries. The physical overlap between components can be adjusted in situ to adjust a total length of the modular stent graft system, for example, to the length of the aneurysm.

Various embodiments of modular stent graft systems including an inflatable fill structure are described herein. An endovascular stent graft system in accordance with various embodiments includes two or more stent grafts that form a flow lumen across an aneurysm. An inflatable fill structure attached to a first stent graft can fill the aneurysm but still be external to a first and a second stent graft. Stent grafts can include, for example, any implants having a tubular graft with at least one proximal and at least one distal opening, and a fluid passage from the proximal opening to the distal opening. In some embodiments, a stent graft includes a radially expandable scaffold to support the graft, which may be rigid or inflatable. In some embodiments, a stent graft may be a component separate from an inflatable fill structure or may be part of an inflatable fill structure. In some embodiments, the scaffold is a balloon-expandable stent, a self-expandable stent, or a scaffold formed by a hardenable fluid fill medium that is injected into inflatable fill elements. Various inflatable fill structures described herein can have an outer wall and an inner wall. In various embodiments, the inner wall of an inflatable fill structure substantially conforms to an outer wall of a stent graft to which the inflatable fill structure is attached. In some embodiments, the outer wall of an inflatable fill structure is unconstrained by a stent graft to which the inflatable fill structure is attached. In various embodiments, the outer wall of an inflatable fill structure is conformable to structures external to a first stent graft (e.g., another stent graft or blood vessel walls). In some embodiments, the outer wall of an inflatable fill structure is conformable to an inner wall of an aneurysm and to a second stent graft that overlaps with the first stent graft. In various embodiments, an inflatable fill structure extends axially beyond a first stent graft and conforms to an inner wall of an aneurysm.

FIGS. 3A, 3B, and 3C are illustrations of modular bifurcated stent grafts. FIG. 3A shows a stent graft system including a bifurcated main stent graft 300 that can be placed onto an aortic bifurcation, and a proximal extension stent graft 302 that can obtain a seal in a proximal neck. FIG. 3B shows a modular stent graft system with a bifurcated main stent graft 310 having a long contralateral leg 312, and a short ipsilateral leg 314. Various other embodiments have a short contralateral leg 312 and a long ipsilateral leg 314. A distal extension stent graft 316 can be placed into the ipsilateral leg 314. In some embodiments, an extension graft (e.g., distal extension stent graft 316) is placed inside of a main stent graft (e.g., main stent graft 310). In other embodiments, the extension graft (e.g., distal extension stent graft 316) is placed around a main stent graft (e.g., main stent graft 310). FIG. 3C shows a modular stent graft system with a bifurcated main stent graft 320 with two short legs 322a and 322b and two distal extension stent grafts 324a and 324b placed inside the legs 322a and 322b, respectively, of the bifurcated main stent graft 320, for extending into iliac arteries. The modular stent grafts shown in FIGS. 3A, 3B, and 3C merely provide examples of modular stent graft systems. In some embodiments, modular stent graft systems may have more than three components. Further, in some embodiments, additional extension stent grafts may be placed proximally or distally to extend an aneurysm repair. For example, a main stent graft can be extended via an extension graft on a proximal end of the main stent graft and an extension graft on a distal end of the main stent graft. In various embodiments, a modular stent graft system includes two or more stent graft components to complete an aneurysm repair.

FIGS. 4A and 4B are illustrations of an apparatus including a bifurcated stent graft 400 and an inflatable fill structure 402. FIG. 4A shows the apparatus when the inflatable fill structure 402 is in a deflated state. FIG. 4B shows the apparatus when the inflatable fill structure is in a filled state. With reference to FIGS. 4A and 4B, the inflatable fill structure 402 is external to a main body of the stent graft 400. A fill tube 404 is provided to allow for delivering fill medium 406 into the inflatable fill structure 402 to change the inflatable fill structure 402 from the deflated state to the filled state. In FIG. 4A, the inflatable fill structure 402 is uninflated and in the deflated state. In FIG. 4B, the inflatable fill structure 402 has been filled with fill medium 406 to cause the inflatable fill structure 402 to be in the filled state.

In some embodiments, the inflatable fill structure 402 is expandable to a toroid shaped three-dimensional structure.

FIGS. 5A and 5B are illustrations of an apparatus in accordance with an embodiment including a bifurcated stent graft 500 and an inflatable fill structure 502 placed at least partially in an infrarenal aortic aneurysm 504, showing deflated and inflated configurations of the inflatable fill structure 502, respectively. In various embodiments, the bifurcated stent graft 500 is at least partially insertable into a blood vessel and has a proximal end, a distal end, an inside surface, and an outside surface. In various embodiments, the inflatable fill structure 502 is fixed to a portion of the outside surface of the bifurcated stent graft 500. In FIG. 5A, the inflatable fill structure 502 is in an uninflated state. In FIG. 5B, the inflatable fill structure 502 is shown as having been filled with fill medium 506 such that the inflatable fill structure 502 is in an inflated or filled state. A mural thrombus 508 and aneurysm wall 510 can limit a radial expansion of the inflatable fill structure 502. As shown in FIG. 5B, the fill medium 506 pushes a wall of the inflatable fill structure 502 proximally into at least a portion of an aneurysm space between the bifurcated stent graft 500 and a proximal neck 512. In this way, the inflatable fill structure 502 can be used to fill the entire (or most of the) aneurysm sac with a single inflatable fill structure mounted onto one of the stent grafts of a modular stent graft system. As shown in the embodiment in FIG. 5B, the inflatable fill structure 502 includes an outer membrane that is configured to extend beyond the proximal end of the bifurcated stent graft 500 into at least a portion of the aneurysm space between the bifurcated stent graft 500 and the proximal neck 512.

FIGS. 6A, 6B, and 6C are cross sectional illustrations showing some steps during deployment of a stent graft system, in accordance with an illustrative embodiment. The stent graft system includes a bifurcated stent graft 600, an inflatable fill structure 602, and a proximal extension stent graft 606. The bifurcated stent graft 600 has a proximal end, a distal end, and an outside surface, and can be placed onto an aortic bifurcation 604. In various embodiments, the inflatable fill structure 602 is fixed to a portion of the outside surface of the bifurcated stent graft 600 and includes an outer membrane that is configured to extend beyond the proximal end of the bifurcated stent graft 600 when the inflatable fill structure 602 is in a filled state.

Figure 6D:
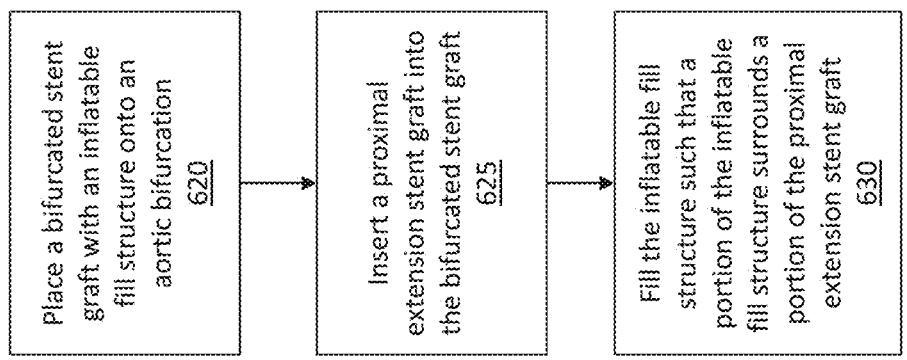
FIG. 6D is a flow diagram illustrating a method of deploying a modular stent graft system, in accordance with an illustrative embodiment.

FIG. 6D is a flow diagram illustrating a method of deploying the modular stent graft system of FIGS. 6A, 6B, and 6C, in accordance with an illustrative embodiment. With reference to FIGS. 6A and 6D, in step 620, the bifurcated stent graft 600 with the inflatable fill structure 602 is placed onto an aortic bifurcation 604. The inflatable fill structure 602 is initially in an uninflated state as shown in FIGS. 6A and 6B. With reference to FIGS. 6B and 6D, in step 625, the proximal extension stent graft 606 is placed at least partially into a main body of the bifurcated stent graft 600. In this way, the proximal extension stent graft 606 extends the aneurysm repair into a proximal neck 608. In various embodiments, the bifurcated stent graft 600 need not be bifurcated and can be readily adapted or used in any aneurysm repair using a stent and an inflatable fill structure. In various embodiments, other extension stent grafts can be placed into any luminous opening of the bifurcated stent graft 600.

With reference to FIGS. 6C and 6D, in step 630, the inflatable fill structure 602 is filled with fill medium 610 to be in an inflated or filled state. The fill medium 610 pushes a wall of the inflatable fill structure 602 against the aneurysm and a portion of the inflatable fill structure 602 extends proximally into an aneurysm space adjacent to the proximal extension stent graft 606. That is, as shown in FIG. 6B, when in an uninflated state, the inflatable fill structure 602 can be confined to being around the bifurcated stent graft 600, but when inflated or filled to be in the filled state as shown in FIG. 6C, the inflatable fill structure 602 expands radially and proximally to fill the entire (or most of the) aneurysm including at least a portion of a space around the proximal extension stent graft 606. When the inflatable fill structure 602 is filled, the wall of the inflatable fill structure 602 can conform to an inner wall of the aneurysm and to at least a portion of an outer surface of the proximal extension stent graft 606 and to at least a portion of the outer surface of the bifurcated stent graft 600. The inflatable fill structure 602 is configured such that when it is in the filled state the inflatable fill structure 602 extends beyond the proximal end of the bifurcated stent graft 600 into which the proximal extension stent graft 606 has been inserted and, thus, surrounds at least a portion of the proximal extension stent graft 606.

FIGS. 7A, 7B, 7C, and 7D are illustrations showing some steps of deployment of a modular stent graft system, in accordance with an illustrative embodiment. The modular stent graft system includes a bifurcated stent graft 700, an inflatable fill structure 702, a fill tube 704, and a distal extension stent graft 714. The bifurcated stent graft 700 includes a main body 701, an ipsilateral leg 706, and a contralateral leg 708. In the bifurcated stent graft 700, the ipsilateral leg 706 is longer than the contralateral leg 708. In alternative embodiments, the bifurcated stent graft 700 can have a short ipsilateral leg and a long contralateral leg. The inflatable fill structure 702 is mounted onto the main body 701 of the bifurcated stent graft 700. In alternative embodiments, the inflatable fill structure 702 can be mounted onto a different portion of the bifurcated stent graft 700, e.g., one or more of the legs 706 and 708, or the main body 701 along with one or more of the legs 706 and 708. The inflatable fill structure 702 is shown in an uninflated state in FIGS. 7A, 7B, and 7C, and is shown in a filled state in FIG. 7D. In various embodiments, the stent graft system includes the fill tube 704 that is configured to allow for filling the inflatable fill structure 702 with a fill medium 718.

Figure 7E:
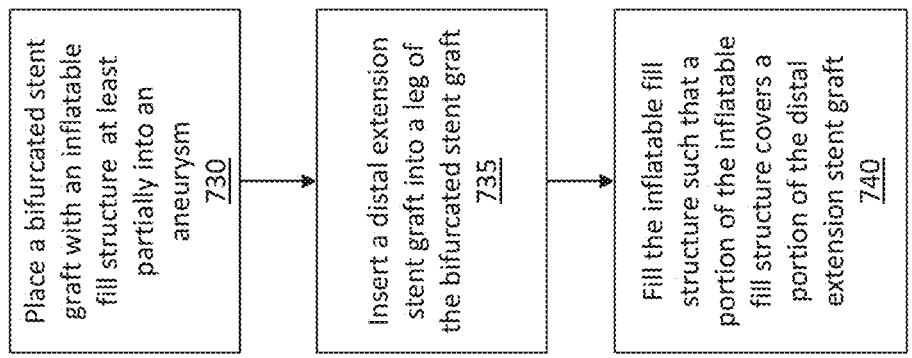
FIG. 7E is a flow diagram illustrating a method of deploying a modular stent graft system, in accordance with an illustrative embodiment.

FIG. 7E is a flow diagram illustrating a method of deploying the modular stent graft system of FIGS. 7A, 7B, 7C, and 7D, in accordance with an illustrative embodiment. With reference to FIGS. 7B and 7E, in step 730, the bifurcated stent graft 700 is placed at least partially in an infrarenal aneurysm 707. In various embodiments, a proximal end of the bifurcated stent graft 700 creates a seal around a proximal neck 710. In various other embodiments, a proximal graft extension is added or inserted into the proximal end of the bifurcated stent graft 700 to create a seal around the proximal neck 710, similar to the embodiment discussed above with reference to FIGS. 6A-6D. With reference to FIGS. 7B and 7C, in various embodiments the ipsilateral leg 706 creates a seal around an ipsilateral iliac artery 712.

With reference to FIGS. 7B, 7C, and 7E, in step 735, the distal extension stent graft 714 is inserted into the contralateral leg 708 of the bifurcated stent graft 700, which is shown in FIG. 7C. In this manner, the bifurcated stent graft 700 can be extended with the distal extension stent graft 714 into a contralateral iliac artery 716, thereby completing the exclusion of the infrarenal aneurysm 707. In various embodiments, the distal extension stent graft 714 creates a seal around the contralateral iliac artery 716. With reference to FIGS. 7D and 7E, in step 740, the inflatable fill structure 702 is filled with fill medium 718 such that the inflatable fill structure 702 is in a filled state, which is illustrated in FIG. 7D. The fluid fill medium 718 pushes a wall of the inflatable fill structure 702 against an inner wall of the aneurysm and distally into an aneurysm space 722, which is adjacent to the ipsilateral leg 706 and the distal extension stent graft 714. That is, in an uninflated state, the inflatable fill structure 702 can be confined to a portion of the bifurcated stent graft 700, such as is shown in the embodiment illustrated in FIGS. 7A, 7B, and 7C where the inflatable fill structure 702 is confined to the main body 701 of the bifurcated stent graft 700 when uninflated. With reference to FIG. 7D, when filled with the fill medium 718, the inflatable fill structure 702 expands radially and in a distal direction to extend over at least a portion of the ipsilateral leg 706 and at least a portion of the distal extension stent graft 714, thereby filling the entire (or most of the) aneurysm space 722. With reference to FIGS. 7A and 7D, in various embodiments, the wall of the inflatable fill structure 702 when in the filled state, as in FIG. 7D, conforms to an inner wall of the aneurysm and to at least a portion of an outer surface of the distal extension stent graft 714 and to at least a portion of the outer surface of the bifurcated stent graft 700. As shown in 7D, a portion of the inflatable fill structure 702 covers a portion of the distal extension stent graft 714 when the inflatable fill structure 702 is in the filled state.

FIGS. 8A, 8B, 8C, and 8D are illustrations showing some steps of deployment of a modular stent graft system, in accordance with an illustrative embodiment. The modular stent graft system includes a bifurcated stent graft 800, an inflatable fill structure 802, a fill tube 804, an extension stent graft 812a, and an extension stent graft 812b. In various embodiments, the inflatable fill structure 802 is mounted onto at least a portion of a main body of the bifurcated stent graft 800. In various embodiments, the bifurcated stent graft 800 includes two short legs 806a and 806b that extend from the main body of the bifurcated stent graft 800. The fill tube 804 is configured to allow for filling the inflatable fill structure 802 with a fill medium 816. The inflatable fill structure 802 is shown in an uninflated state in FIGS. 8A, 8B, and 8C, and is shown in a filled state in FIG. 8D.

Figure 8E:
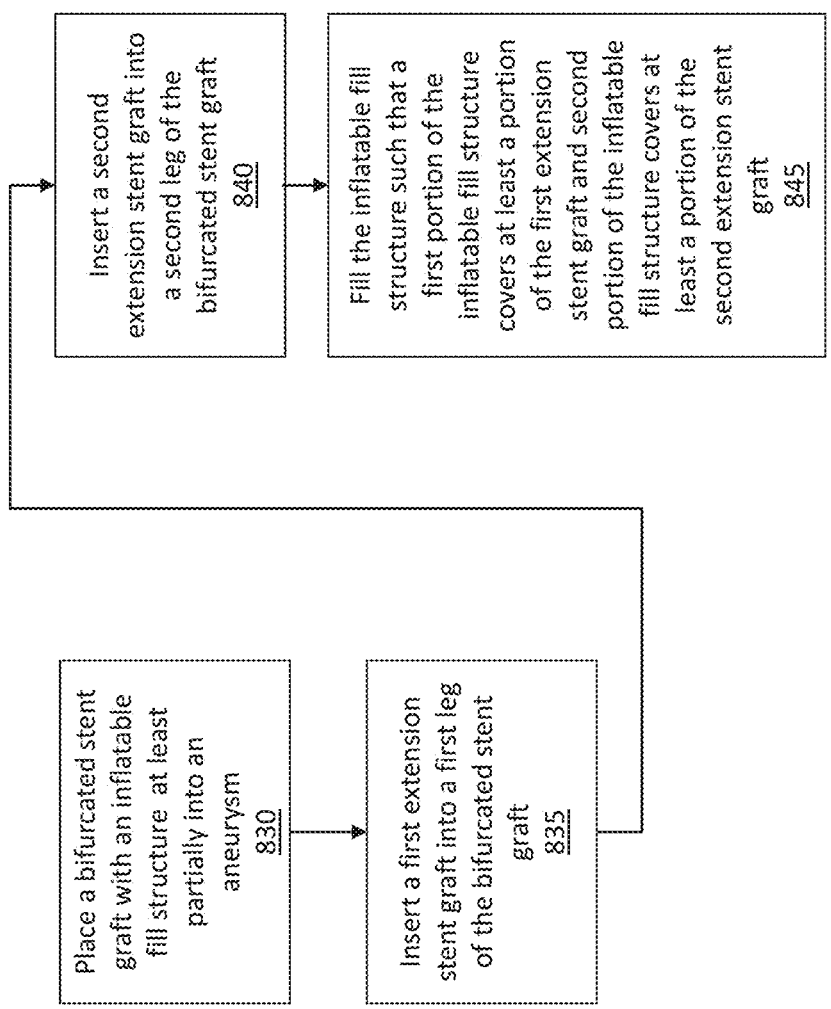
FIG. 8E is a flow diagram illustrating a method of deploying a modular stent graft system, in accordance with an illustrative embodiment.

FIG. 8E is a flow diagram illustrating a method of deploying the modular stent graft system of FIGS. 8A, 8B, 8C, and 8D, in accordance with an illustrative embodiment. With reference to FIGS. 8B and 8E, in step 830, the bifurcated stent graft 800 with the attached inflatable fill structure 802 is placed in an aneurysm, e.g., infrarenal aneurysm 808. In various embodiments, a proximal end of the bifurcated stent graft 800 creates a seal about a proximal neck 810. In alternative embodiments, a proximal extension stent graft can be inserted into the proximal end of the bifurcated stent graft 800 to create a seal about the proximal neck 810.

With reference to FIGS. 8A, 8C, and 8E, in step 835, a first extension stent graft (e.g., the extension stent graft 812a) is inserted into a first leg (e.g., the leg 806a) of the bifurcated stent graft 800, which is shown in FIG. 8C. Similarly, in step 840, a second extension stent graft (e.g., the extension stent graft 812b) is inserted into a second leg (e.g., the leg 806b) of the bifurcated stent graft 800, which is shown in FIG. 8C. In various embodiments, the extension stent graft 812a and the extension stent graft 812b create seals about respective iliac arteries 814a and 814b. Thus, the bifurcated stent graft 800 can be extended with two distal extension stent grafts 812a and 812b into the iliac arteries 814a and 814b, thereby completing the exclusion of the aneurysm.

With reference to FIGS. 8D and 8E, in step 845, the inflatable fill structure 802 is filled with fill medium 816 to be in a filled state. In various embodiments, the fill medium 816 pushes a wall of the inflatable fill structure 802 against the aneurysm and distally into an aneurysm space 818 adjacent to the distal extension stent grafts 812a and 812b. That is, with reference to FIG. 8C, the inflatable fill structure 802 can be confined to an area about the bifurcated stent graft 800 in an uninflated state, but when inflated or filled with fill medium 816 as in FIG. 8D, the inflatable fill structure 802 expands radially and distally to cover at least a portion of the extension stent graft 812a and at least a portion of the extension stent graft 812b. Thus, when in the inflated or filled state, the inflatable fill structure 802 can extend over (and about) the extension stent grafts 812a and 812b. In various embodiments, the inflatable fill structure 802 is configured such that a wall of the inflatable fill structure 802 conforms to an inner wall of the aneurysm and to at least a portion of outer surfaces of the distal extension stent grafts 812a and 812b and to at least a portion of an outer surface of the bifurcated stent graft 800 when the inflatable fill structure 802 is in the filled state.

As discussed above, FIGS. 6C, 7D, and 8D provide some examples of modular stent graft systems with an inflatable fill structure mounted on the main body of a bifurcated stent graft. In alternative embodiments, the inflatable fill structure may be mounted onto a proximal or distal extension stent graft, such that when inflated or filled the inflatable fill structure extends into an aneurysm space adjacent to the main body of a bifurcated stent graft. In some embodiments, the stent graft to which the inflatable fill structure is affixed is placed into an aneurysm first, and additional stent graft components are inserted partially into the stent graft having the inflatable fill structure.

Figure 10B:
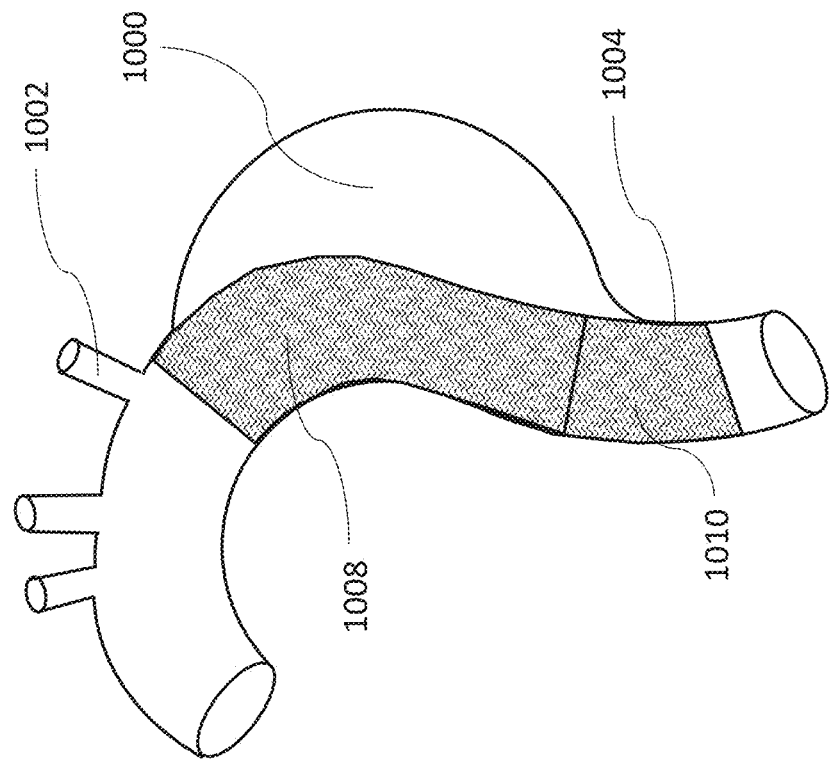
FIGS. 10A and 10B are illustrations of a one-piece stent graft and two sections of a modular stent graft, respectively, placed across a thoracic aortic aneurysm.
Figure 10A:
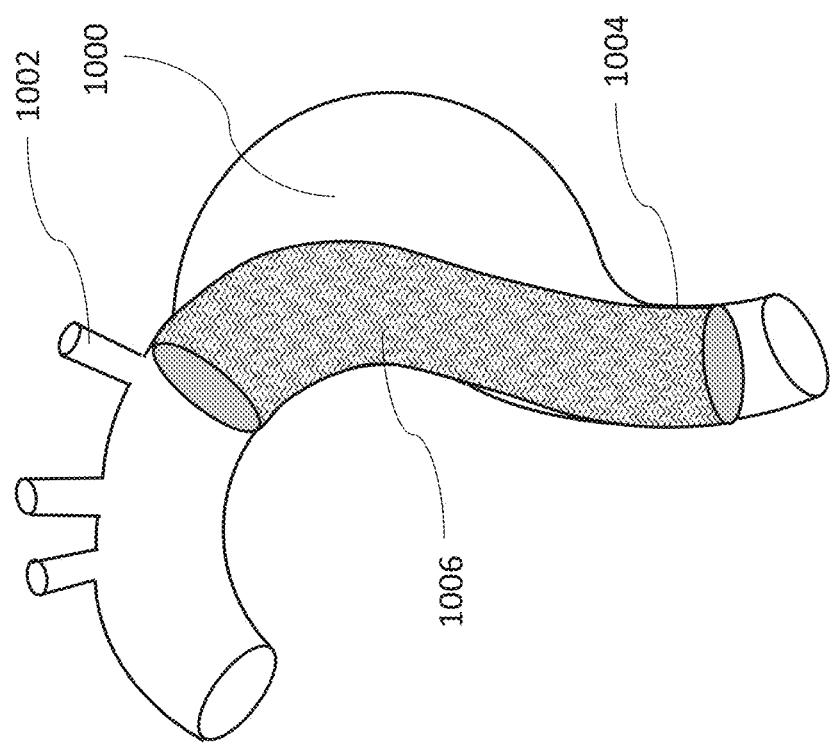

In some embodiments, a modular stent graft system includes an inflatable fill structure that is used for endovascular repair of a thoracic aneurysm. FIG. 9 is an illustration of a thoracic aortic aneurysm 900. The aneurysm 900 in a descending thoracic aorta 902 is distal to a subclavian artery 904. FIGS. 10A and 10B are illustrations of a one-piece stent graft and two sections of a modular stent graft, respectively, placed across a thoracic aortic aneurysm 1000. FIG. 10A illustrates a single tubular stent graft 1006 used to repair the aneurysm 1000. In FIG. 10B, two overlapping stent grafts 1008 and 1010 are used, thereby accomplishing a similar end result of the singular stent graft of FIG. 10A to repair the aneurysm 1000.

In some instances, more than one stent graft may be used to repair thoracic aneurysms because a diameter of the aorta changes rapidly along a length of the blood vessel and it can be difficult to design a single graft (that can have a single diameter along a length of the graft) that is adequately suited for repair of the thoracic aneurysm. In some instances, the aneurysm can be too long to be adequately bridged by a single stent graft. In other instances, a single stent graft that has the exact length needed to maximize proximal and distal seal might not be available to a surgeon. With multiple, overlapping stent grafts, the length of the stent graft system can be adjusted in situ to maximize a seal length proximally, below the subclavian artery 1002, and distally 1004. The use of two or more stent grafts for the treatment of thoracic aneurysms is considered a modular stent graft system repair.

FIGS. 11A, 11B, 11C, and 11D are illustrations showing some steps of deployment of a modular stent graft system across a thoracic aortic aneurysm, in accordance with an illustrative embodiment. The modular stent graft system includes a thoracic stent graft 1100, an inflatable fill structure 1102, a fill tube 1104, and a second stent graft 1110. In various embodiments, the inflatable fill structure 1102 is mounted along at least a portion of a length of the thoracic stent graft 1100. In various embodiments, the fill tube 1104 is in fluid communication with the inflatable fill structure 1102 to and is configured to allow for providing fill medium 1114, such as a fill liquid, a hardenable substance, or the like, to an inside area of the inflatable fill structure 1102. The inflatable fill structure 1102 is shown in an uninflated state in FIGS. 11A, 11B, and 11C, and is shown in a filled state in FIG. 11D.

Figure 11B:
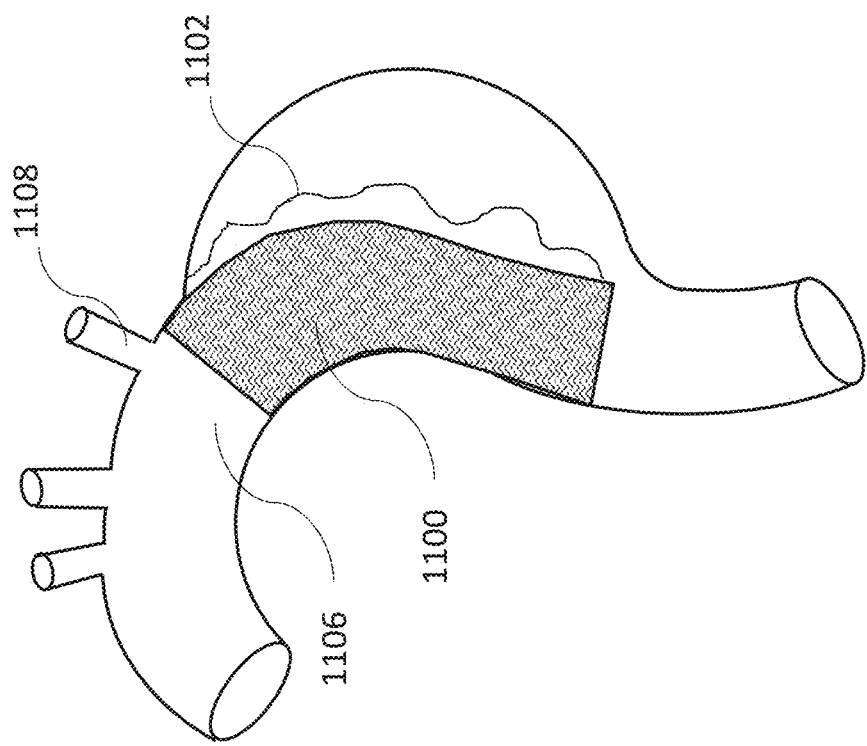
FIGS. 11A, 11B, 11C, and 11D are illustrations showing some steps of deployment of a modular stent graft system placed across a thoracic aortic aneurysm, in accordance with an illustrative embodiment.
Figure 11A:
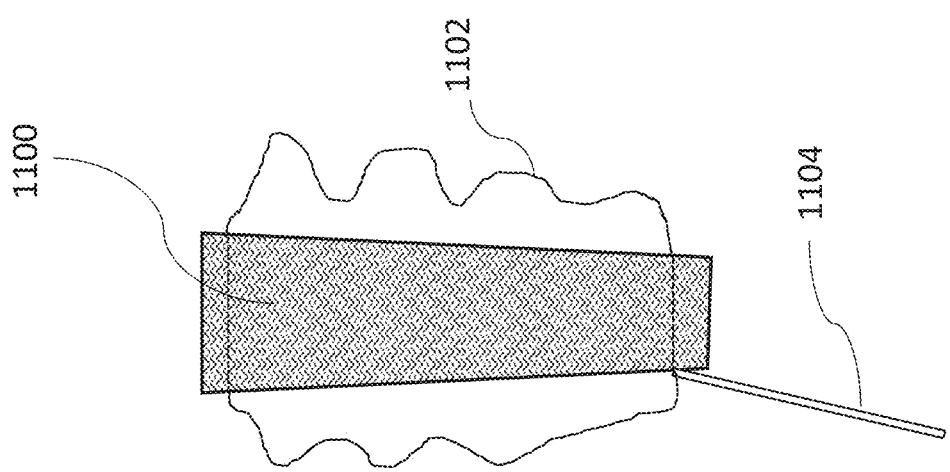
Figure 11D:
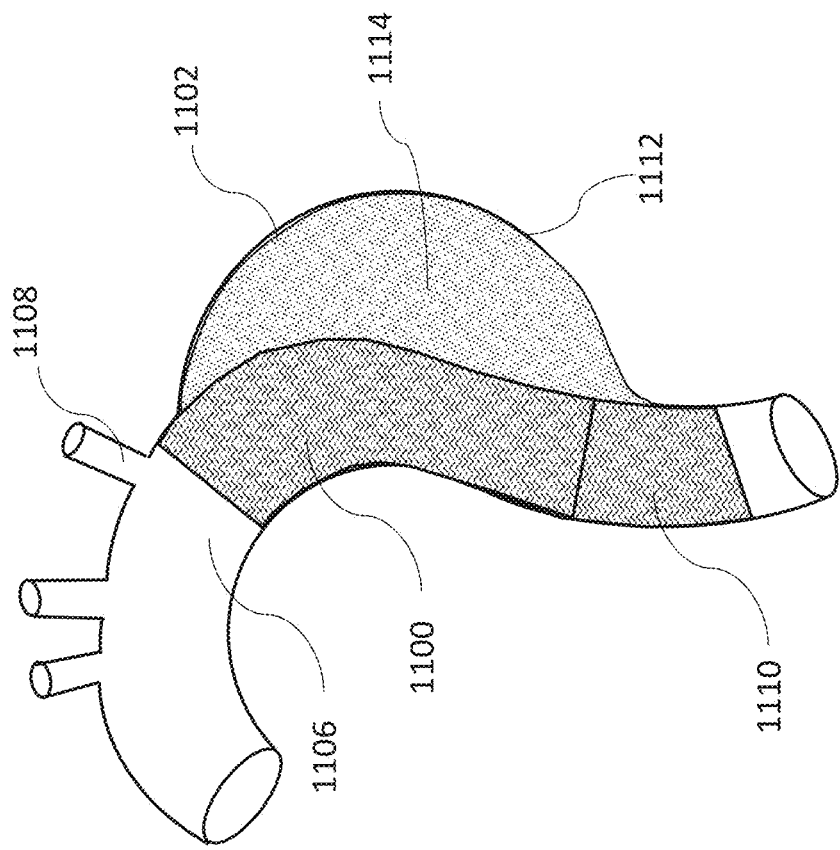
Figure 11C:
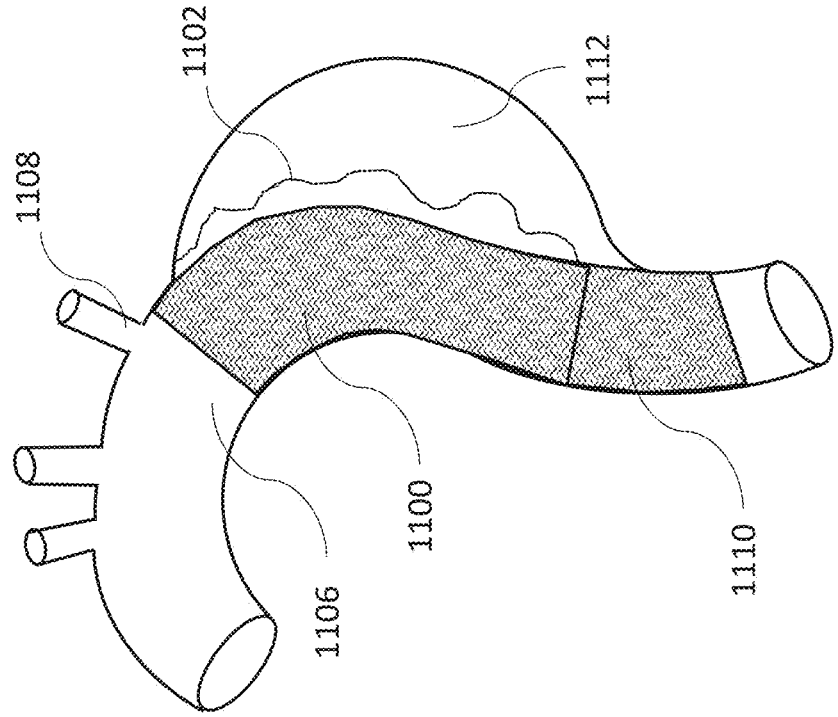
Figure 11E:
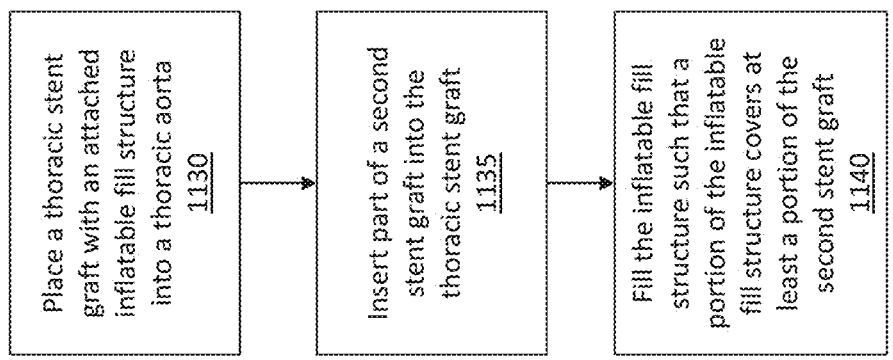
FIG. 11E is a flow diagram illustrating a method of deploying a modular stent graft system in a thoracic aortic aneurysm, in accordance with an illustrative embodiment.

FIG. 11E is a flow diagram illustrating a method of deploying the modular stent graft system of FIGS. 11A, 11B, 11C, and 11D in a thoracic aortic aneurysm, in accordance with an illustrative embodiment. In various embodiments, the modular stent graft system is placed in a thoracic aorta 1106 below a subclavian artery 1108. With reference to FIGS. 11B and 11E, in step 1130, the thoracic stent graft 1100 with the attached inflatable fill structure 1102 is placed into the thoracic aorta 1106, just below the subclavian artery 1108. In various embodiments, the thoracic stent graft 1100 is configured to create a proximal seal about a proximal end of the thoracic aorta 1106. With reference to FIGS. 11C and 11E, in step 1135, the second stent graft 1110 is placed partially within the thoracic stent graft 1100. In this manner, the second stent graft 1110 extends the aneurysm repair by the thoracic stent graft 1100 distally, thereby excluding an aneurysm 1112.

With reference to FIGS. 11D and 11E, in step 1140, the inflatable fill structure 1102 is filled with fill medium 1114. In various embodiments, the inflatable fill structure 1102 fills an aneurysm space adjacent to the thoracic stent graft 1100 and adjacent to the second stent graft 1110, such that a portion of the inflatable fill structure 1102 covers at least a portion of the second stent graft 1110 when the inflatable fill structure 1102 is in the filled state. In various embodiments, the inflatable fill structure 1102 extends beyond an end of the thoracic stent graft 1100 and over at least a portion of the second stent graft 1110 when inflated or filled. In various embodiments, a wall of the inflatable fill structure 1102 contacts an inner wall of the aneurysm 1112 and an outer surface of the second stent graft 1110 and an outer surface of the thoracic stent graft 1100. In some embodiments, a placement of the thoracic stent graft 1100 with the attached inflatable fill structure 1102 is swapped with a placement of the second stent graft 1110, such that the thoracic stent graft 1100 can be configured to provide a seal about a distal end of the thoracic aorta 1106 while the second stent graft 1110 can be configured to provide a proximal seal about the thoracic aorta 1106.

In some embodiments, an inflatable fill structure is configured to have wall dimensions that allow the inflatable fill structure to expand radially as well as axially, thereby allowing the inflatable fill structure to fill an aneurysm space as fully as possible. FIG. 12 is an illustration of an inner wall 1202 and an outer wall 1204 of an inflatable fill structure 1200 in close proximity to a tubular stent graft 1206, in accordance with an illustrative embodiment. A wall of the inflatable fill structure 1200 may be divided into the inner wall 1202, indicated by a continuous bold line, and the outer wall 1204 indicated by a broken bold line. In some embodiments, the inner wall 1202 extends along the stent graft 1206. In some embodiments, the inner wall 1202 extends along a portion of the stent graft 1206. In some embodiments, the inflatable fill structure 1200 is fixed to the stent graft 1206. In various embodiments, the inflatable fill structure 1200 is configured such that when the inflatable fill structure 1200 is filled with fill medium, the inner wall 1202 substantially conforms to the stent graft 1206. In some embodiments, the inner wall 1202 has a cylindrical shape with a diameter equal to or slightly greater than an outer diameter of the stent graft 1206 when fully expanded. In some embodiments, when the inflatable fill structure 1200 is filled with fill medium, the outer wall 1204 extends in a proximal and a distal direction, beyond the proximal and distal ends of the stent graft 1206, as shown in FIG. 12. In some embodiments, the outer wall 1204 is configured to extend in either a proximal or a distal direction, beyond the proximal or the distal end of the stent graft 1206. In various embodiments, the outer wall 1204 is configured to not be constrained by the stent graft 1206. Some embodiments include an inflatable fill structure that extends about only a portion of the stent graft 1206. Other embodiments, however, can have an inflatable fill structure extend about the entire stent graft 1206.

Figure 13B:
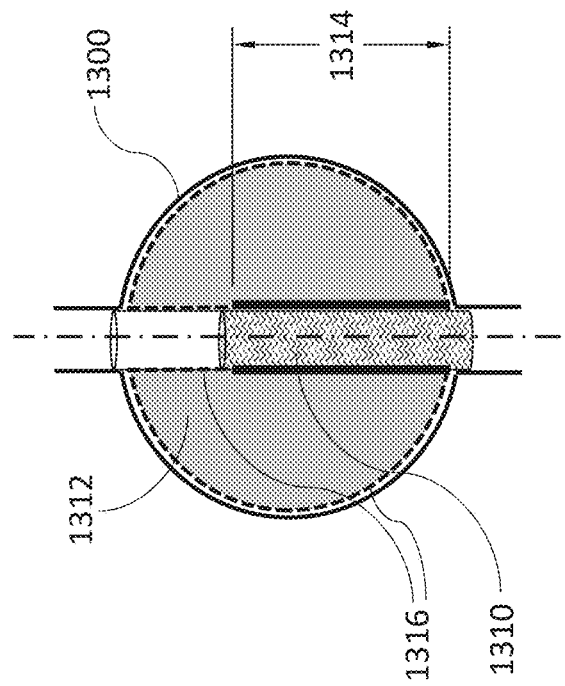
FIGS. 13A and 13B are illustrations of some variables that can be used in calculating a length dimension of an inner wall and a length dimension of an outer wall, in accordance with illustrative embodiments.
Figure 13A:
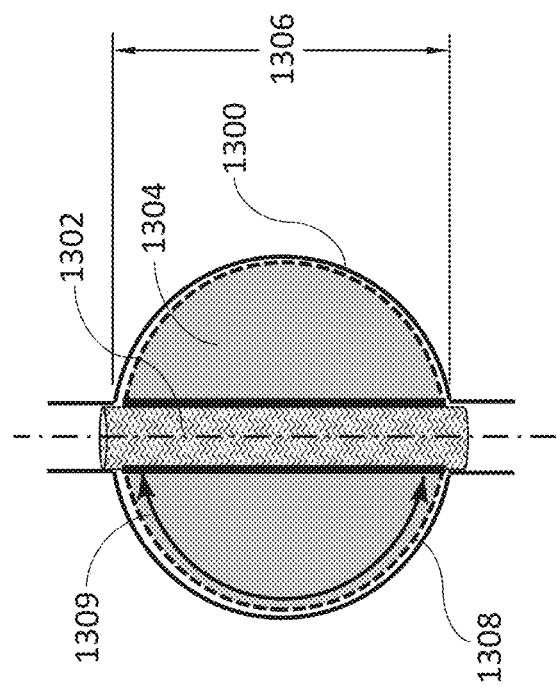

FIGS. 13A and 13B are illustrations of some variables that can be used in calculating a length dimension of an inner wall and a length dimension of an outer wall for an inflatable fill structure, in accordance with various embodiments. An inflatable fill structure for use in conjunction with a single stent graft as shown in FIG. 13A can be compared to an inflatable fill structure for use in a modular stent graft system as shown in FIG. 13B. Infrarenal aneurysms can have a length, for example, of 80-120 mm and a diameter, for example, of 55-80 mm. FIG. 13A depicts an example in which there is an idealized or extreme case of a spherical aneurysm 1300 without mural thrombus. The aneurysm diameter can be equal to the length 1306 of the aneurysm 1300. A single stent graft 1302 can have an attached inflatable fill structure 1304 and can be placed in the aneurysm 1300. A length of an inner wall of the inflatable fill structure 1304 can be equal to the length 1306 of the aneurysm 1300. For the inflatable fill structure 1304 to fill the entire aneurysm sac and conform to an inner wall of the aneurysm 1300, an outer wall 1308 of the inflatable fill structure 1304 can have a length equal to an outer aneurysm wall length 1309. Using the geometrical relationship between the diameter and the circumference of a circle, the outer aneurysm wall length 1309 may be, for example, 1.57 times (i.e., 3.14/2 times) the length of the inner wall length 1306 to fill an aneurysm of circular shape. That is, the length 1309 of the outer wall 1308 can be equal, for example, to the length 1306 of the inner wall times pi divided by 2.

FIG. 13B illustrates a stent graft component 1310 of a modular stent graft system with an inflatable fill structure 1312 placed in the spherical aneurysm 1300. The stent graft component 1310 does not bridge the entire aneurysm 1300, but can be connected to other stent graft components for bridging the entire aneurysm 1300. In various embodiments, a length 1314 of an inner wall of the inflatable fill structure 1312 is shorter than a length of the aneurysm 1300. In various embodiments, for the inflatable fill structure 1312 to fill the entire aneurysm sac, an outer wall 1316 of the inflatable fill structure 1312 is dimensioned so as to allow for covering the inner wall of the aneurysm 1300 plus a length of the aneurysm not spanned by the stent graft component 1310. In various embodiments, the inflatable fill structure 1312 has an outer wall 1316 with a length of more than 1.57 times the length 1314 of the inner wall of the inflatable fill structure 1312. For example, if the stent graft component 1310 in the embodiment of FIG. 13B only covered half of the total length of the aneurysm 1300, the length 1314 of the inner wall of the inflatable fill structure 1312 would equal one-half of the diameter of the spherical aneurysm 1300. In such an example, the length of the outer wall 1316 of the inflatable fill structure 1312 would have to be at least 0.5+1.57=2.07 times the diameter of the aneurysm 1300 to completely fill the aneurysm 1300. In this case, the length of the outer wall 1316 would be more than 4 times the length 1314 of the inner wall. Therefore, in some embodiments, a length of an outer wall of an inflatable fill structure is between 2 and 6 times a length of an inner wall of the inflatable fill structure. For example, the length of the outer wall can be 2, 2.5, 2.75, 3, 4, 5, 6, or any other suitable number times the length of the inner wall of the inflatable fill structure.

Figure 14A:
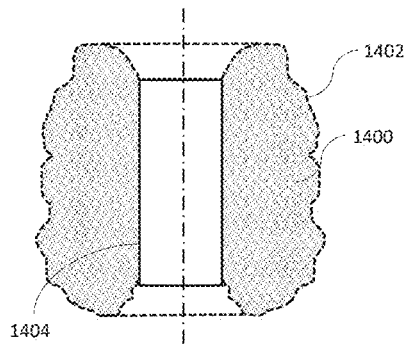
FIGS. 14A, 14B, 14C, and 14D are illustrations of shapes of inflatable fill structures, in accordance with some illustrative embodiments.
Figure 14B:
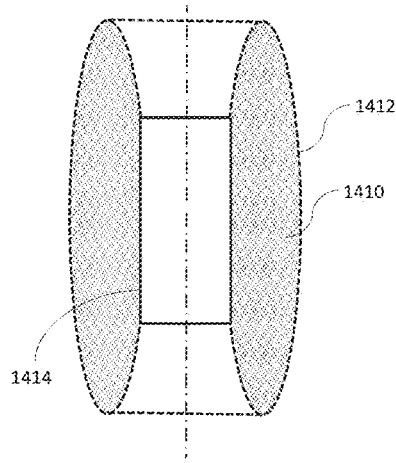
Figure 14C:
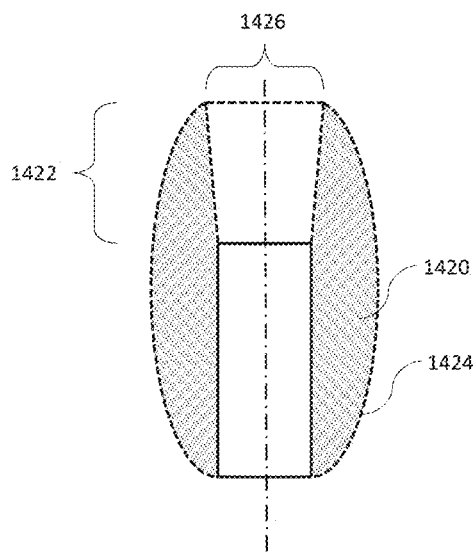
Figure 14D:
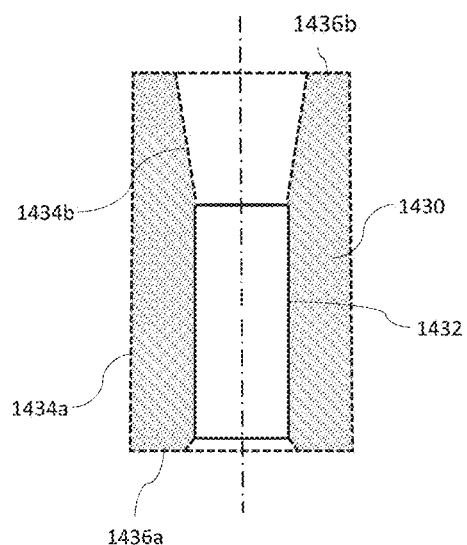

FIGS. 14A, 14B, 14C, and 14D are illustrations of examples of symmetric and asymmetric shapes of inflatable fill structures, in accordance with some illustrative embodiments. With reference to FIG. 14A, in some embodiments an inflatable fill structure 1400 has any arbitrary relaxed shape and is dimensioned such that an outer wall 1402 of the inflatable fill structure 1400, when the inflatable fill structure 1400 is filled with fill medium, can contact an aneurysm wall and fill an aneurysm space. In various embodiments, an inner wall 1404 of the inflatable fill structure 1400 conforms to a tubular stent graft. The embodiments shown in FIGS. 14B, 14C, and 14D provide examples of some shapes that can minimize an uninflated profile of an inflatable fill structure and/or ease manufacturing. FIG. 14B shows a symmetrical toroidal shaped inflatable fill structure 1410 in accordance with an embodiment having an outer wall 1412 extending beyond both ends of an inner wall 1414 of the inflatable fill structure 1410. With reference to FIG. 14C, in some embodiments that include a stent graft with an inflatable fill structure that extends beyond one end of the stent graft and over a second stent graft, an asymmetrically mounted toroid-shaped inflatable fill structure 1420 may be used. In various embodiments, a segment 1422 of an outer wall 1424 of the inflatable fill structure 1420 that conforms to a second stent graft can have a maximum diameter 1426 that is larger than a diameter of the second stent graft, thereby allowing for full radial expansion of the second stent graft. Toroid-shaped inflatable fill structures, such as those shown in FIGS. 14C and 14D, can be formed by tip molding, blow molding, or any other suitable method. In various embodiments, an inflatable fill structure may be manufactured from one or more flat sheets of material. FIG. 14D shows a geometry of an inflatable fill structure 1430 in accordance with an embodiment that can be fabricated from several flat sheets of material. An inner wall 1432 of the inflatable fill structure 1430 may be formed by a first sheet rolled into a tube shape. An outer wall of the inflatable fill structure 1430 may be formed by two sheets 1434a and 1434b rolled into tubes and by two circular sheets with central openings 1436a and 1436b, thereby forming the ends of the inflatable fill structure 1430. In various embodiments, the sheets may be fused or bonded together along their edges.

FIGS. 15A, 15B, and 15C show axial views of examples of inflatable fill structures in accordance with various embodiments. FIG. 15A shows an axi-symmetric toroid-shaped inflatable fill structure 1500. An inner wall 1504 and an outer wall 1502 of the inflatable fill structure 1500 are of tubular shape. FIG. 15B shows an inflatable fill structure 1510 made from a tubular-shaped inner wall 1512 and two flat sheets 1514a and 1514b of material fused along a seam line 1516 to form an outer wall. FIG. 15C shows a football shaped inflatable fill structure 1520 made from a tubular-shaped inner wall 1522 and four flat sheets 1524a, 1524b, 1524c, and 1524d of material to form an outer wall.

FIGS. 16A, 16B, and 16C are illustrations of connections between a stent graft and an inner wall of an inflatable fill structure, in accordance with some illustrative embodiments. FIG. 16A shows an inflatable fill structure 1600 that can be attached to an outer surface of a stent graft 1602. A proximal end 1604a and a distal end 1604b of an inner wall 1606 of the inflatable fill structure 1600 are attached to the stent graft 1602. In various embodiments, a fill tube 1608 is connected to the inflatable fill structure 1600 at the distal end 1604b. In some embodiments, the attachment of the inner wall 1606 may be at individual points along a circumference of the stent graft 1602. In some embodiments, the attachment of the inner wall 1606 can be made around a continuous circumference of the stent graft 1602. In various embodiments, the inner wall 1606 is attached to the stent graft 1602 via an adhesive and/or sutures. In some embodiments, the inner wall 1606 and the stent graft 1602 can be made from thermo-plastic and may be thermally fused together.

FIG. 16B shows an inner wall 1614 of an inflatable fill structure 1610 attached to a stent graft 1612 along an entire length of the inner wall 1614. The fill tube 1608 can be used to fill the inflatable fill structure 1610. In an embodiment shown in FIG. 16C, a stent graft 1622 forms an inner wall of an inflatable fill structure 1620. In such an embodiment, an outer wall 1624 of the inflatable fill structure 1620 can be directly bonded to the stent graft 1622 and, thus, the stent graft 1622 could be an integral part of the inflatable fill structure 1620. One advantage of such an embodiment is a reduction in device components and bonds, in addition to a reduction in an uninflated profile of the stent graft system.

Figure 17:
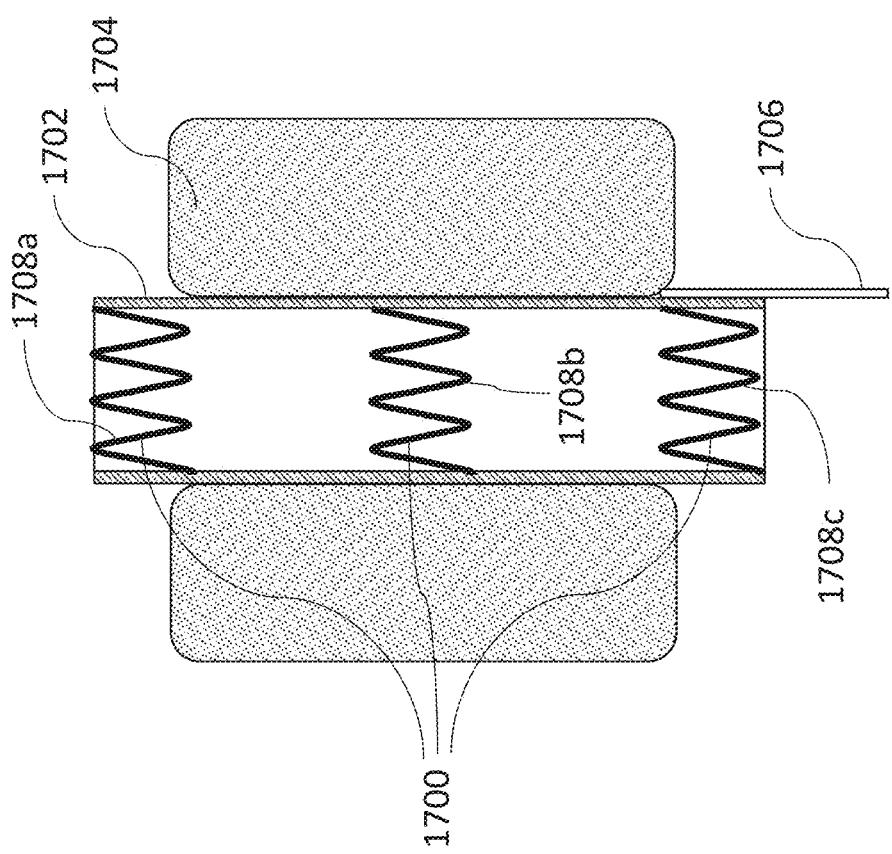
FIG. 17 is an illustration of a stent graft with an inflatable fill structure and a radially expandable scaffold, in accordance with an illustrative embodiment.

FIG. 17 is an illustration of a graft 1702 with an inflatable fill structure 1704 and radially expandable scaffolds 1700, in accordance with an illustrative embodiment. The inflatable fill structure 1704 can further include a fill tube 1706. In various embodiments, the radially expandable scaffold 1700 includes one or more radially expandable stents 1708a, 1708b, and 1708c (also referred to as radially expandable scaffolds). In various embodiments, the radially expandable stents 1708a, 1708b, and 1708c are self-expanding stents or are balloon-expandable stents. The radially expandable stents 1708a, 1708b, and 1708c may be made, for example, from a metal or a polymer. In some embodiments, the radially expandable stents 1708a, 1708b, and 1708c comprise a continuous stent such as a helical stent. Another example of a continuous, radially expandable stent are stent ring elements connected by axial connectors. The radially expandable stents 1708a, 1708b, and 1708c can support the tubular graft 1702 and maintain a patent flow lumen. In some embodiments, the proximal and distal radially expandable stents 1708a and 1708c may form a seal between the tubular graft 1702 and the wall of a blood vessel.

Figure 18:
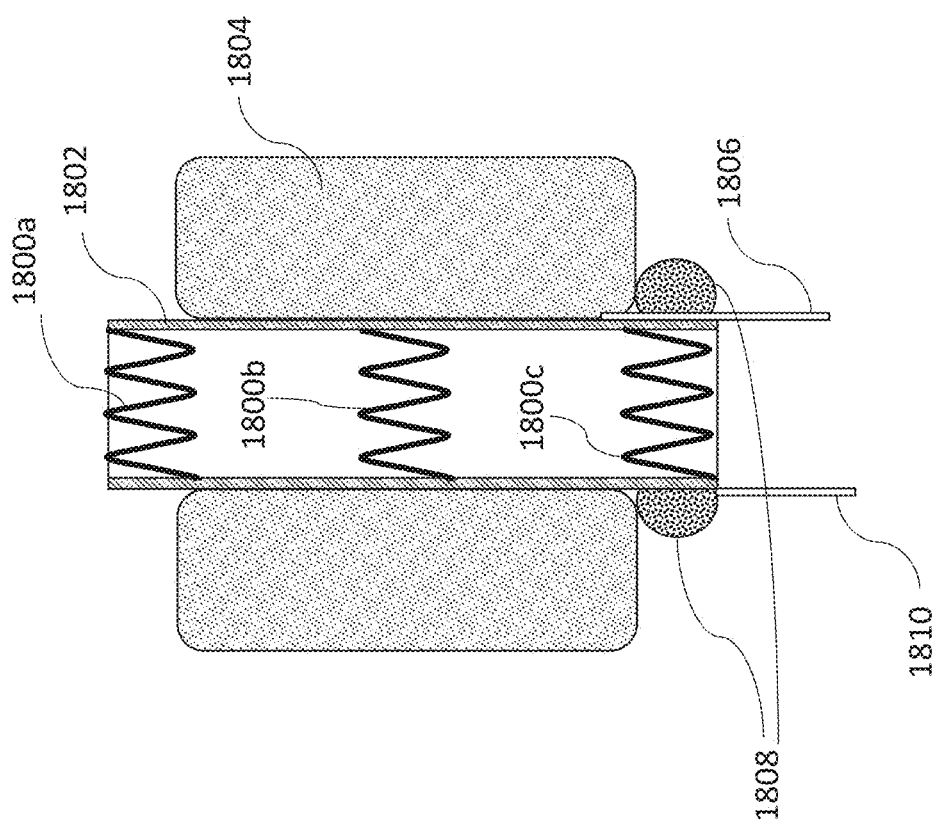
FIG. 18 is an illustration of a stent graft with two inflatable fill structures and a radially expandable scaffold, in accordance with an illustrative embodiment.

FIG. 18 is an illustration of a stent graft with two inflatable fill structures and a radially expandable scaffold, in accordance with an illustrative embodiment. A stent graft system in accordance with an embodiment includes radially expandable stents 1800a, 1800b, and 1800c, a tubular graft 1802, a first inflatable fill structure 1804, and a first fill tube 1806. In various embodiments, the stent graft system also includes a second inflatable fill structure 1808 that is connectable to a second fill tube 1810. In various embodiments, the second inflatable fill structure 1808 is configured to form a circumferential seal against a blood vessel wall. In various embodiments, the stent graft system can be placed in an aneurysm and the second inflatable fill structure 1808 can be filled with a fluid fill medium that can be hardenable.

Figure 19:
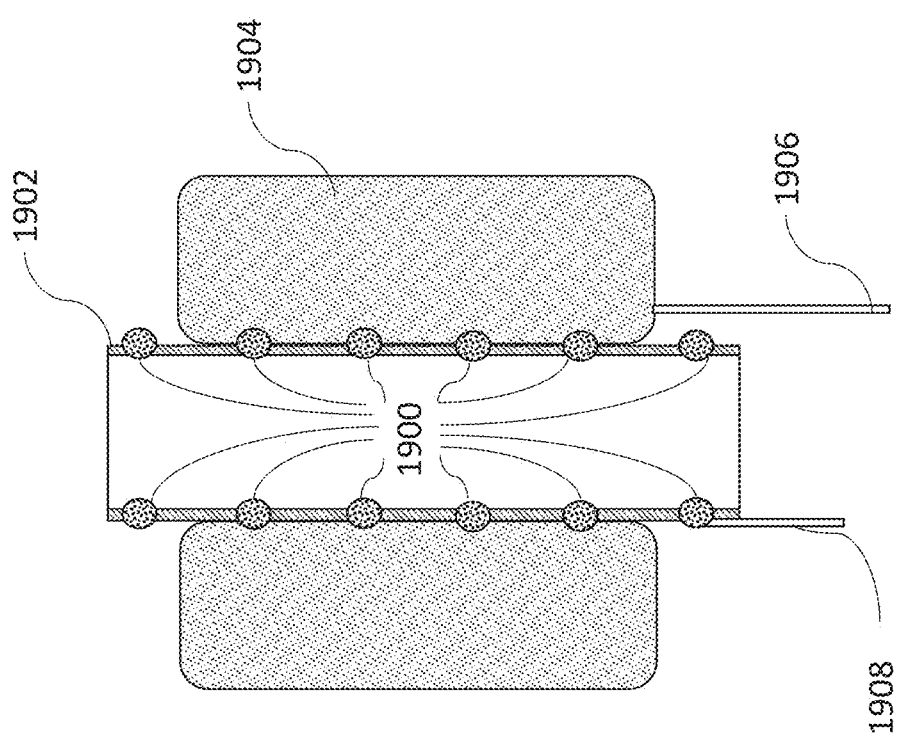
FIG. 19 is an illustration of a stent graft with an inflatable fill structure and an inflatable, radially expandable scaffold, in accordance with an illustrative embodiment.

FIG. 19 is an illustration of a stent graft 1902 with an attached inflatable fill structure 1904 and an inflatable, radially expandable scaffold, in accordance with an illustrative embodiment. The inflatable fill structure 1904 can be connected to a first fill tube 1906. In various embodiments, the stent graft 1902 includes the radially expandable scaffold that include a series of inflatable fill elements 1900 that are fillable with a fill medium that can be hardenable. The fill medium in the inflatable fill elements 1900 can form rings configured to support a graft of the stent graft 1902. In some embodiments, the inflatable fill elements 1900 are in fluid communication with each other such that they can be filled from a single second fill tube 1908.

Figure 22:
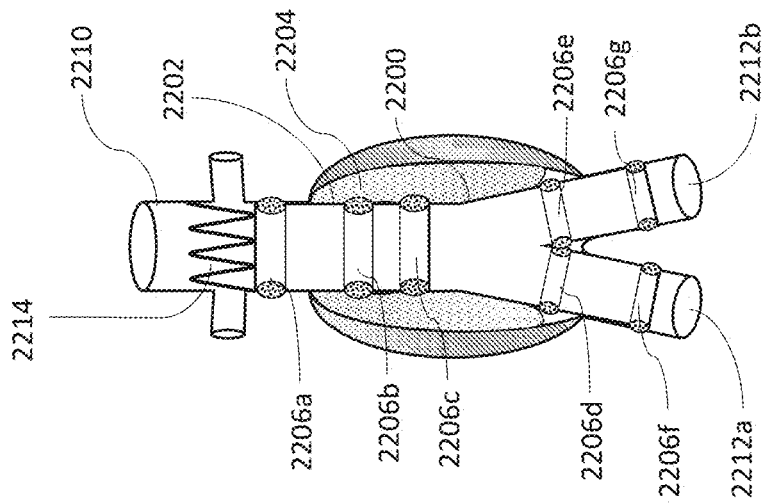
FIG. 22 is an illustration of a stent graft system with an inflatable fill structure, a rigid, radially expandable scaffold, and inflatable, radially expandable scaffolds, in accordance with an illustrative embodiment.
Figure 21:
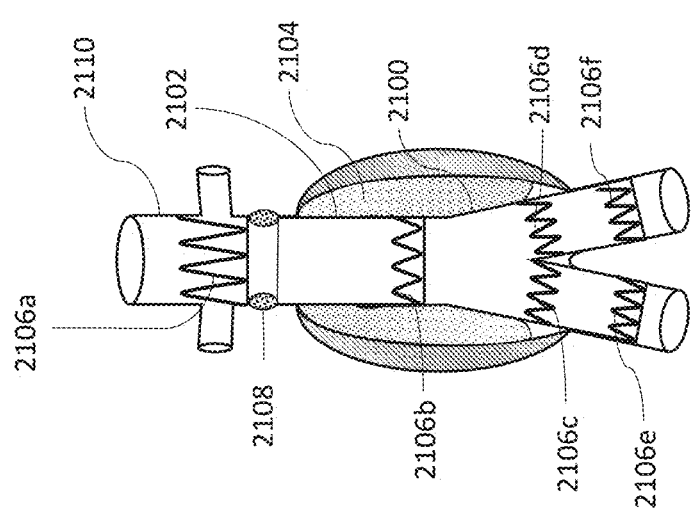
FIG. 21 is an illustration of a stent graft system with an inflatable fill structure, rigid, radially expandable scaffolds, and an inflatable, radially expandable scaffold, in accordance with an illustrative embodiment.
Figure 20:
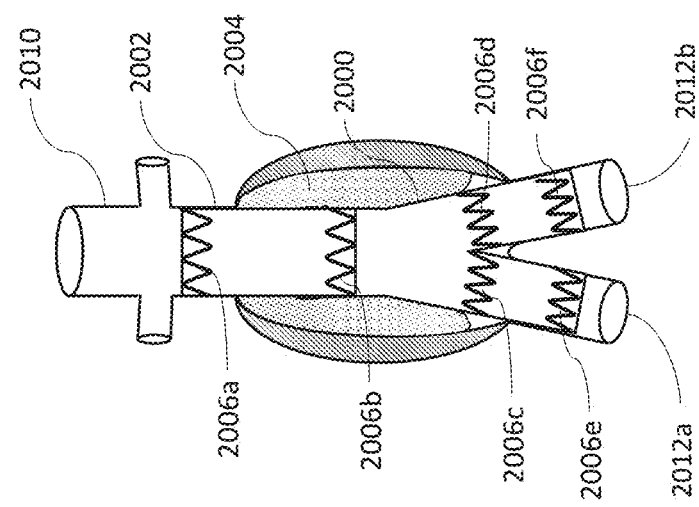
FIG. 20 is an illustration of a stent graft system with an inflatable fill structure and radially expandable scaffolds, in accordance with an illustrative embodiment.

FIGS. 20, 21, and 22 illustrate various embodiments of radially expandable scaffolds integrated in an infrarenal modular stent graft system with an inflatable fill structure. FIG. 20 is an illustration of a stent graft system with an inflatable fill structure 2004 and radially expandable scaffolds 2006a, 2006b, 2006c, 2006d, 2006e, and 2006f, in accordance with an illustrative embodiment. The stent graft system can include a bifurcated stent graft 2000 and a proximal extension stent graft 2002. The inflatable fill structure 2004 of an illustrative embodiment can be mounted on the bifurcated stent graft 2000. The bifurcated stent graft 2000 and proximal extension stent graft 2002 can be supported by the radially expandable scaffolds 2006a-2006f. The radially expandable scaffolds 2006a-2006f may be, for example, self-expanding stents or balloon expandable stents. The most proximal radially expandable scaffold 2006a and/or the most distal radially expandable scaffolds 2006e and 2006f can be configured to seal a graft of the bifurcated stent graft 2000 and the proximal extension stent graft 2002 against an aorta 2010 and iliac arteries 2012a and 2012b, respectively.

FIG. 21 is an illustration of a stent graft system with an inflatable fill structure 2104, rigid, radially expandable scaffolds 2106a, 2106b, 2106c, 2106d, 2106e, and 2106f, and an inflatable radially expandable scaffold 2108, in accordance with an illustrative embodiment. The stent graft system further includes a bifurcated stent graft 2100 and a proximal extension stent graft 2102. The inflatable fill structure 2104 is mounted on the bifurcated stent graft 2100 in an illustrative embodiment. The bifurcated stent graft 2100 and the proximal extension stent graft 2102 can be supported by the radially expandable stents 2106a-2106f. In various embodiments, the inflatable radially expandable scaffold 2108 is an inflatable ring-shaped fill structure located on the proximal extension stent graft 2102 and is configured to provide a seal against an aortic wall 2110. In various embodiments, the radially expandable scaffold 2106a provides fixation of the proximal extension stent graft 2102 in an aorta along the aortic wall 2110. The radially expandable scaffold 2106a may, for example, have hooks or barbs for penetrating into the aortic wall 2110, thereby enhancing fixation.

FIG. 22 is an illustration of a stent graft system with an inflatable fill structure 2204, a rigid, radially expandable scaffold 2214, and inflatable radially expandable scaffolds 2206a, 2206b, 2206c, 2206d, 2206e, 2206f, and 2206g, in accordance with an illustrative embodiment. The stent graft system includes a bifurcated stent graft 2200 and a proximal extension stent graft 2202. In some embodiments, the inflatable fill structure 2204 is mounted on the bifurcated stent graft 2200. The bifurcated stent graft 2200 and the proximal extension stent graft 2202 are supported by the inflatable radially expandable scaffolds 2206a-2206g, which may be, for example, ring-shaped inflatable fill elements that can be filled with a fill medium that is hardenable. The most proximal inflatable radially expandable scaffold 2206a and/or most the most distal inflatable radially expandable scaffolds 2206f and 2206g can be configured to seal the stent graft system against an aorta 2210 and iliac arteries 2212a and 2212b, respectively. In various embodiments, the radially expandable scaffold 2214 provides fixation of the stent graft system in the aorta 2210.

Figure 23:
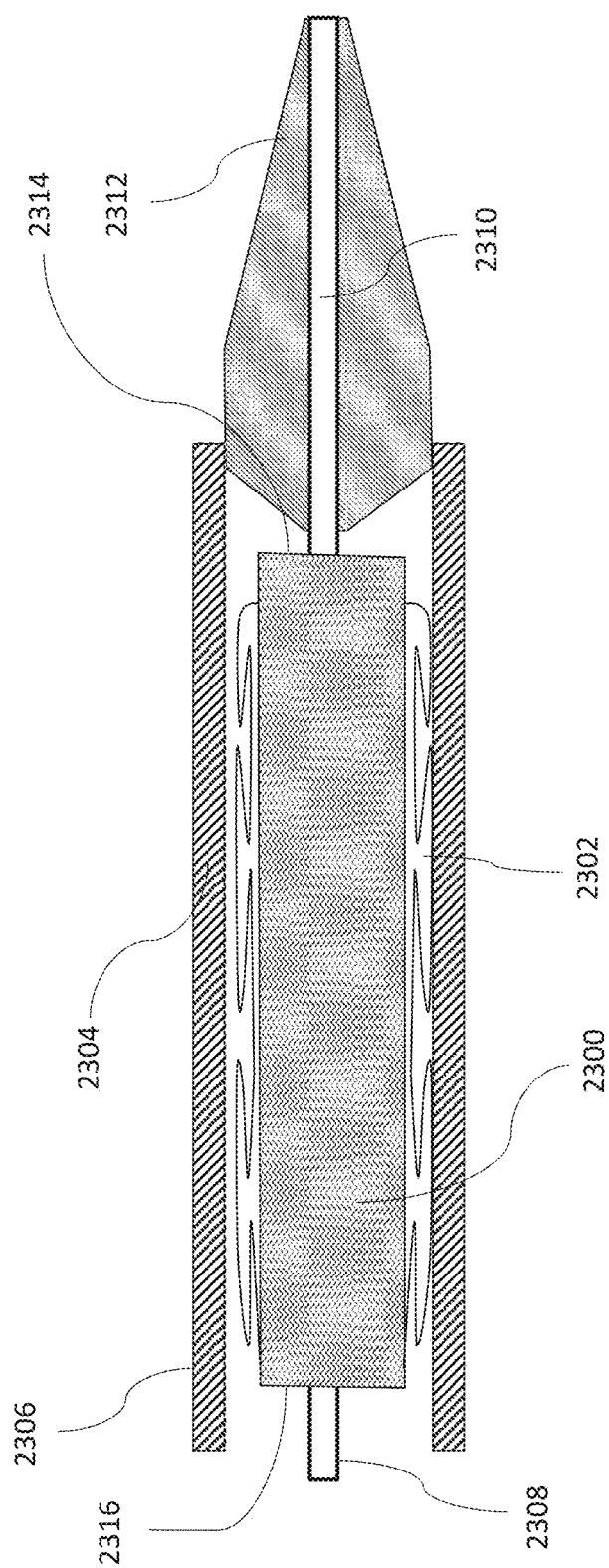
FIG. 23 is an illustration of the distal end of a delivery catheter including a tubular stent graft with an inflatable fill structure, in accordance with an illustrative embodiment.

FIG. 23 is an illustration of a distal end of a delivery catheter 2304 including a tubular stent graft 2300 with an inflatable fill structure 2302, in accordance with an illustrative embodiment. The delivery catheter 2304 allows for delivering the stent graft 2300 that has the inflatable fill structure 2302 attached thereto. In various embodiments, the delivery catheter 2304 has an outer sheath 2306 for surrounding the stent graft 2300, and also has an inner core 2308 with a guide wire lumen 2310, and a dilator tip 2312. The dilator tip 2312 can assist atraumatic insertion of the delivery catheter 2304 into a vascularity. In various embodiments, the inflatable fill structure 2302 is in a collapsed, uninflated state, on the stent graft 2300 before insertion. In an illustrative embodiment, the ends of the inflatable fill structure 2302 can be configured (e.g., folded or collapsed) as to not extend axially beyond the proximal 2314 and distal 2316 openings of the stent graft 2300 when the inflatable fill structure 2302 is in an uninflated state within the delivery catheter 2304. Such an embodiment can help to ensure that, upon deployment of the stent graft 2300 in a body, the inflatable fill structure 2302 does not obstruct a flow lumen of the stent graft 2300 or get pinched against an inner wall of the stent graft 2300 by a second, overlapping stent graft that can be partially inserted in the first stent graft 2300 before the inflatable fill structure 2302 is filled. In various embodiments, the inflatable fill structure 2302 is configured such that once it is in a filled state it extends axially beyond at least one end of the stent graft 2300.

Figure 24:
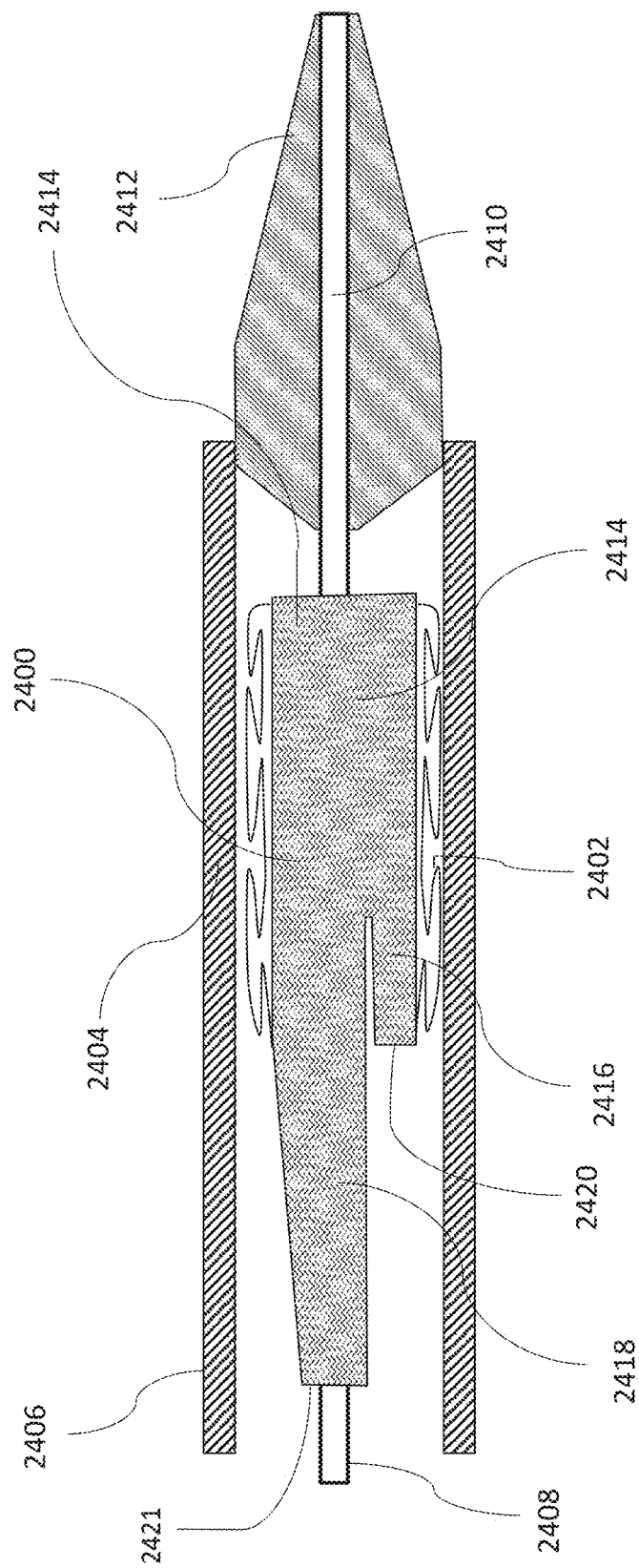
FIG. 24 is an illustration of the distal end of a delivery catheter including a bifurcated stent graft with an inflatable fill structure, in accordance with an illustrative embodiment.

FIG. 24 is an illustration of a distal end of a delivery catheter 2404 containing a bifurcated stent graft 2400 with an inflatable fill structure 2402, in accordance with an illustrative embodiment. The bifurcated stent graft 2400 with the attached inflatable fill structure 2402 can be loaded into the delivery catheter 2404. In various embodiments, the delivery catheter 2404 has an outer sheath 2406 that can surround the bifurcated stent graft 2400, an inner core 2408 with a guide wire lumen 2410, and a dilator tip 2412. The dilator tip 2412 is configured to assist atraumatic insertion of the catheter into a vascularity. The bifurcated stent graft 2400 includes a main body 2414, a short leg 2416, and a long leg 2418. There is a distal opening 2420 in the short leg 2416, and a distal opening 2421 in the long leg 2418. In various embodiments, the inflatable fill structure 2402 is configured (e.g., folded or collapsed) such that a distal end of the inflatable fill structure 2402 does not extend axially beyond the distal opening 2420 in the short leg 2416 of the bifurcated stent graft 2400 when the inflatable fill structure 2402 is in an uninflated state within the delivery catheter 2404. Such a configuration can help to prevent the inflatable fill structure 2402 from obstructing a flow lumen during installation and can help avoid impingement by a second stent graft that can be placed in the short leg 2416 of the bifurcated stent graft 2400. In various embodiments, the inflatable fill structure 2402 is configured such that once it is in a filled state it extends axially beyond an end of the short leg 2416.

The embodiments illustrated in FIGS. 23 and 24 provide examples of stent grafts with inflatable fill structures loaded in a delivery catheter for delivery and deployment in a body. FIGS. 7A, 8A, 11A, and 18 illustrate some additional embodiments of stent graft systems with inflatable fill structures that can be loaded into a similar catheter delivery system. In various embodiments, an outer wall of an inflatable fill structure is configured to extend beyond an end of an inner wall of a stent graft when inflated or filled. Thus, in such embodiments, the inflatable fill structure can axially extend beyond the stent graft. In some instances, if the inflatable fill structure extends beyond the stent graft prematurely, installation of the modular stent system can be hindered. In some embodiments, the inflatable fill structure is folded onto itself inside the delivery catheter such that the ends of the inflatable fill structure do not axially extend beyond the ends of the stent graft when the inflatable fill structure is uninflated. Thus, in such embodiments, when the stent graft is deployed in the body, the inflatable fill structure does not obstruct the distal and proximal openings of the stent graft and, therefore, does not interfere with the placement of additional, overlapping stent grafts within the lumen of the stent graft. When the inflatable fill structure is filled with fill medium, the inflatable fill structure may extend axially beyond one or more of the ends of the stent graft.

Figure 25:
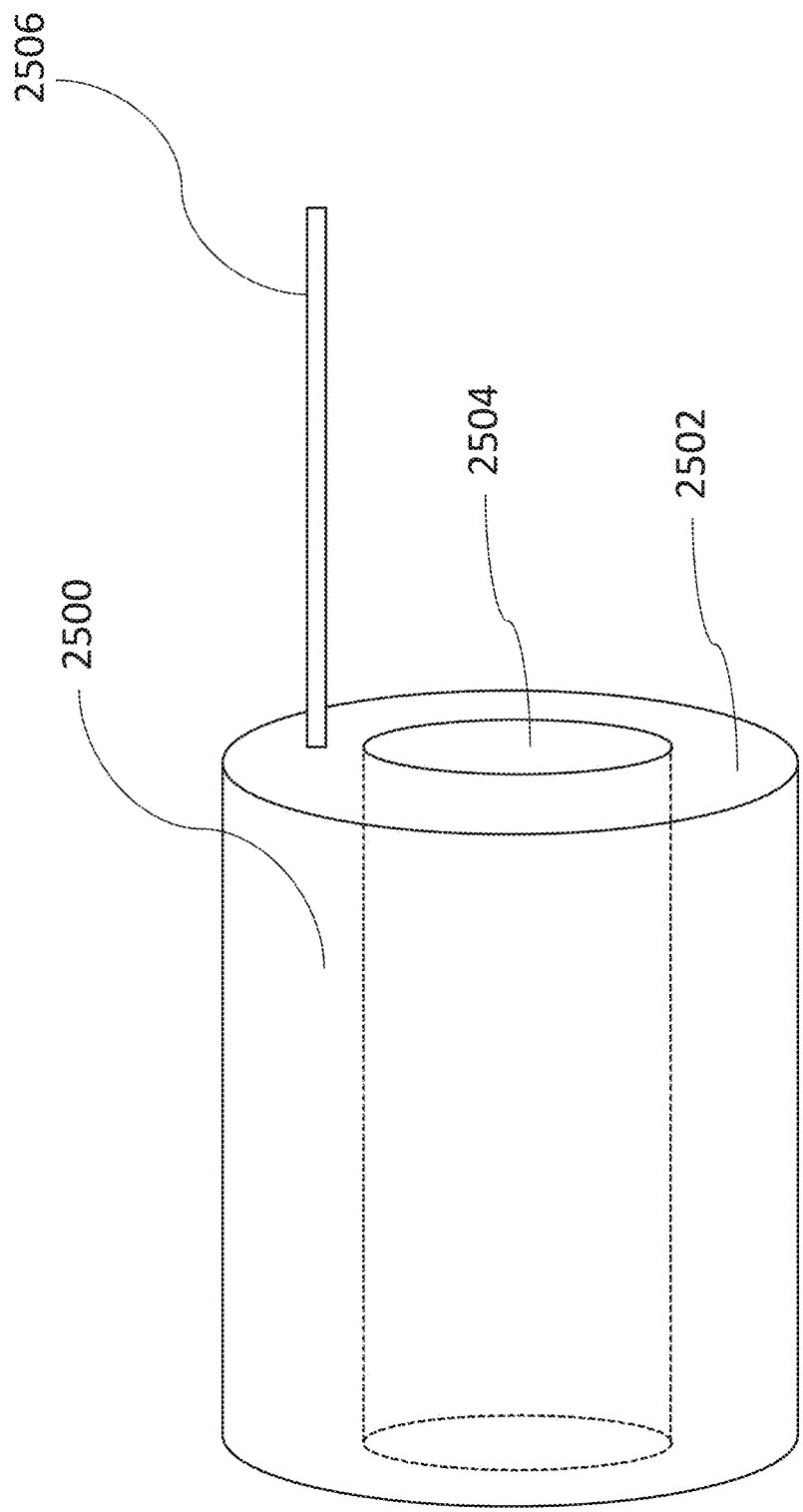
FIG. 25 is an illustration of an aneurysm fill system, in accordance with an illustrative embodiment.

Although an aneurysm fill system can have an inflatable fill structure attached to a graft, in some embodiments an aneurysm fill system can be delivered to the aneurysm separate and/or detached from a graft. FIG. 25 is an illustration of an aneurysm fill system 2500, in accordance with an illustrative embodiment. An embodiment of the aneurysm fill system 2500 can have a toroid-shaped inflatable fill structure 2502 with a central passage 2504 and a fill line 2506. The fill line 2506 can be detachable. In various embodiments, a diameter of the central passage 2504 is sufficiently large so as to accommodate a stent graft within the central passage 2504. An outer diameter of the inflatable fill structure 2502 can be sufficiently large so as to conform to an inner wall of an aneurysm when the inflatable fill structure 2502 is filled with a fill medium. A length of the inflatable fill structure 2502 can be sufficiently long so as to axially fill a substantial portion (e.g., most, if not all) of an aneurysm.

Figure 26D:
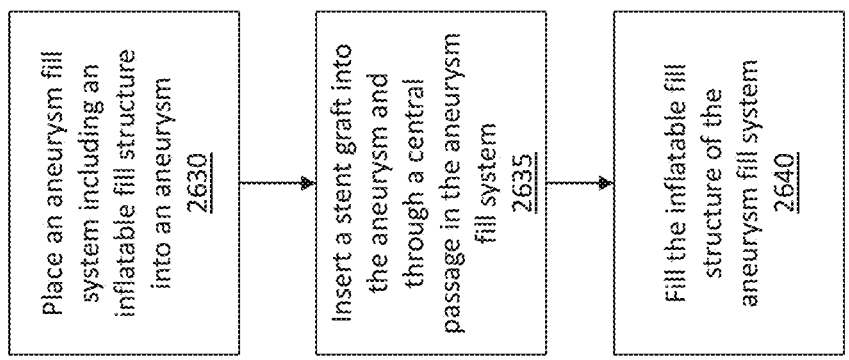
FIG. 26D is a flow diagram illustrating a method of placing and filling an aneurysm fill system, in accordance with an illustrative embodiment.

FIGS. 26A, 26B, and 26C are illustrations showing some steps during placement and inflation or filling of an aneurysm fill system 2600 through which a stent graft 2610 can be placed in an infrarenal aneurysm, in accordance with an illustrative embodiment. FIG. 26D is a flow diagram illustrating a method of using the aneurysm fill system 2600 of FIGS. 26A, 26B, and 26C with the stent graft 2610, in accordance with an illustrative embodiment. With reference to FIGS. 26A and 26D, in step 2630, the aneurysm fill system 2600 is placed in an aneurysm 2604. In some embodiments, the aneurysm fill system 2600 can be delivered to the aneurysm 2604 via a catheter. FIG. 26A illustrates the aneurysm fill system 2600 after it has been delivered and released into the aneurysm 2604. In various embodiments, the aneurysm fill system 2600 includes an inflatable fill structure 2602 and a fill tube 2606 that can fluidly connect the inflatable fill structure 2602 with an external reservoir containing a fill medium. In various embodiments, the inflatable fill structure 2602 is configured to have a central passage 2608.

With reference to FIGS. 26B and 26D, in step 2635, the stent graft 2610 is placed through the central passage 2608 (refer to FIG. 26A) of the inflatable fill structure 2602 of the aneurysm fill system 2600 and spans across the aneurysm 2604. The stent graft 2610 illustrated in FIG. 26B is a bifurcated stent graft, but any suitable stent graft can be used with the method. For example, in some embodiments a modular stent graft can be used. The stent graft 2610 is configured to exclude the aneurysm 2604 from aortic blood flow when deployed. The fill tube 2606 allows for providing a fill medium to the inflatable fill structure 2602.

With reference to FIGS. 26C and 26D, in step 2640, the inflatable fill structure 2602 of the aneurysm fill system 2600 is filled with a fill medium 2612. FIG. 26C shows the completed implant with the inflatable fill structure 2602 filled with the fill medium 2612. The fill tube 2606 (refer to FIG. 26B) can then be removed. When inflated or filled as in FIG. 26C, the inflatable fill structure 2602 conforms to an inner wall 2614 of the aneurysm and to an outer surface of the stent graft 2610. The aneurysm fill system 2600 can augment aneurysm repair with a stent graft 2610 by filling an aneurysm sac, thereby reducing or eliminating Type II endoleaks and stabilizing the aneurysm repair from long-term remodeling of the aneurysm.

One advantage of embodiments with a detached fill structure is that the aneurysm fill system can be added to any aneurysm repair that is performed using an existing stent graft. Such embodiments provide an alternative to filling the aneurysm sac with a fill medium after placement of a stent graft. Filling the aneurysm with a fill medium after stent graft placement runs the risk of embolization of the fill medium into the blood stream and blood-fill medium interaction in the aneurysm sac. The blood-fill medium interaction may interfere with the hardening of the fill medium. By placing an aneurysm fill system into the aneurysm sac prior to placement of a stent graft, the fill medium can be contained within an inflatable fill structure and embolization of the fill medium and undesired blood interaction can be avoided. In some embodiments, a detached fill structure can be placed in an aneurysm prior to placement of the stent graft, thereby providing access through a central opening of the detached fill structure for stent graft placement. The detached fill structure can be held in position in the aneurysm sac, thereby avoiding migration during stent graft placement. The detached fill structure can remain connected to a fill tube thereby allowing for filling of the inflatable fill structure after completion of the stent graft placement.

Figure 27E:
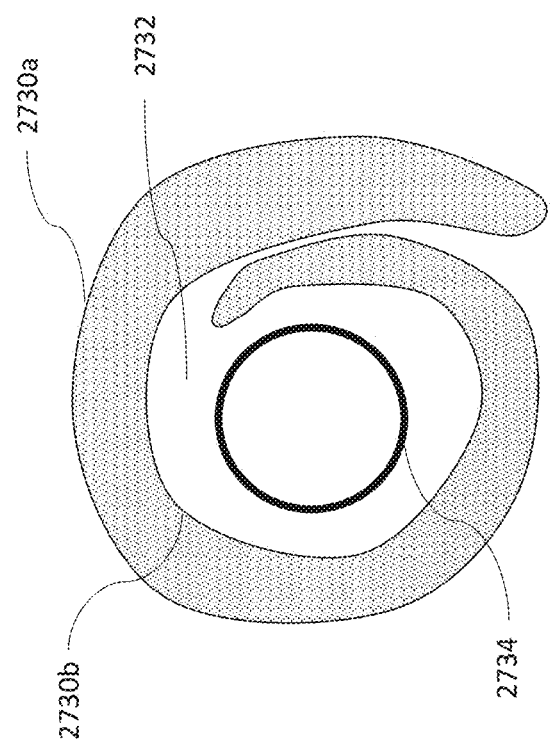

FIGS. 27A, 27B, 27C, 27D, and 27E are cross-sectional illustrations of inflation compartments of an aneurysm fill system, in accordance with some illustrative embodiments. FIG. 27A illustrates a toroid-shaped inflatable fill structure 2700. A central passage 2702 of the inflatable fill structure 2700 can have a circular cross-section configured to accommodate a stent graft 2704. FIG. 27B illustrates an inflatable fill structure including two compartments 2706 and 2707 that can be in fluid communication with each other. In various embodiments, the compartments 2706 and 2707 are each manufactured from two flat sheets of material 2708a and 2708b, and 2709a and 2709b, respectively, fused together at their edges. The two compartments 2706 and 2707 form a central passage 2710 that is configured to accommodate a stent graft 2712. FIG. 27C illustrates an embodiment of a detached inflatable fill structure with four compartments 2720a, 2720b, 2720c, and 2720d that can be in fluid communication with each other. In various embodiments, the individual compartments 2720a, 2720b, 2720c, and 2720d are manufactured from flat sheets of material fused at the edges, similar to the embodiment illustrated in FIG. 27B. In various embodiments, the four compartments 2720a, 2720b, 2720c, and 2720d form a continuous fill structure with a central passage 2722 that is configured to accommodate a stent graft 2724.

In alternative embodiments, the compartments of the inflatable fill structures illustrated in FIGS. 27B and 27C are not in fluid communication with each other. Accordingly, each of the compartments can have separate fill tubes. By inflating the individual compartments separately, a lateral force can be applied to the stent graft by the inflated compartment. By selecting the sequence of filling the individual compartments, an axis of the stent graft can be moved into a more favorable position to avoid undesirable angulations and kinking of the stent graft. Such an embodiment may be preferred in highly tortuous and distorted aneurysms. Alternatively, the compartments of the inflatable fill structures illustrated in FIGS. 27B and 27C could be delivered separately to form a closed configuration.

Figure 27D:
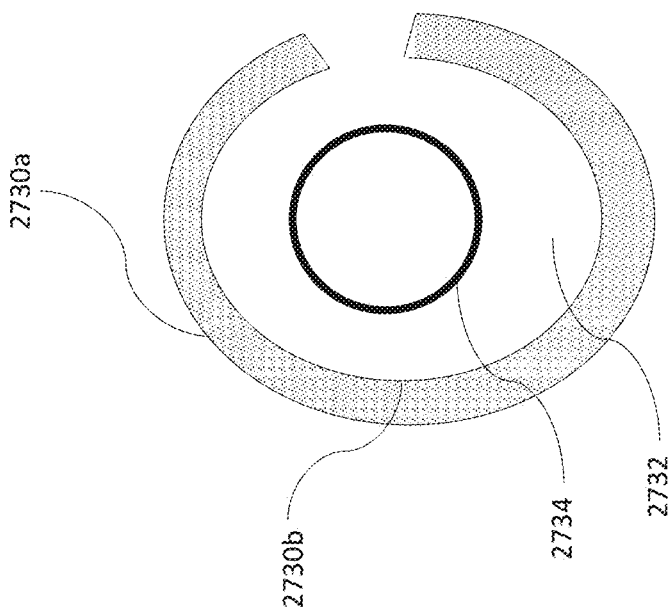

FIGS. 27D and 27E illustrate alternative embodiments of an inflatable fill structure. The inflatable fill structures illustrated in FIGS. 27D and 27E can be made from two flat sheets 2730a and 2730b fused together at their edges. A central passage 2732 can be configured to accommodate a stent graft 2734. The central passage 2732 can be formed by rolling the inflatable fill structure into a tubular configuration. The configuration may be open, as shown in FIG. 27D, or overlapping, as shown in FIG. 27E. In either embodiment, the ends of the inflatable fill structure may touch and form the central passage 2732 for the stent graft 2734 when the inflatable fill structure is filled with fill medium.

Figure 28A:
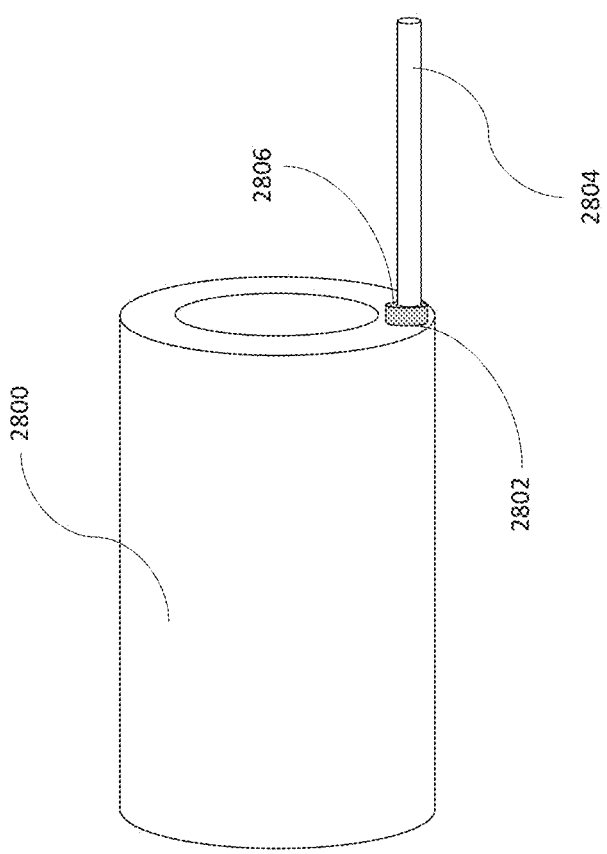
FIGS. 28A, 28B, and 28C are illustrations of detachable connections between an inflatable fill system and a fill tube, in accordance with some illustrative embodiments.
Figure 28B:
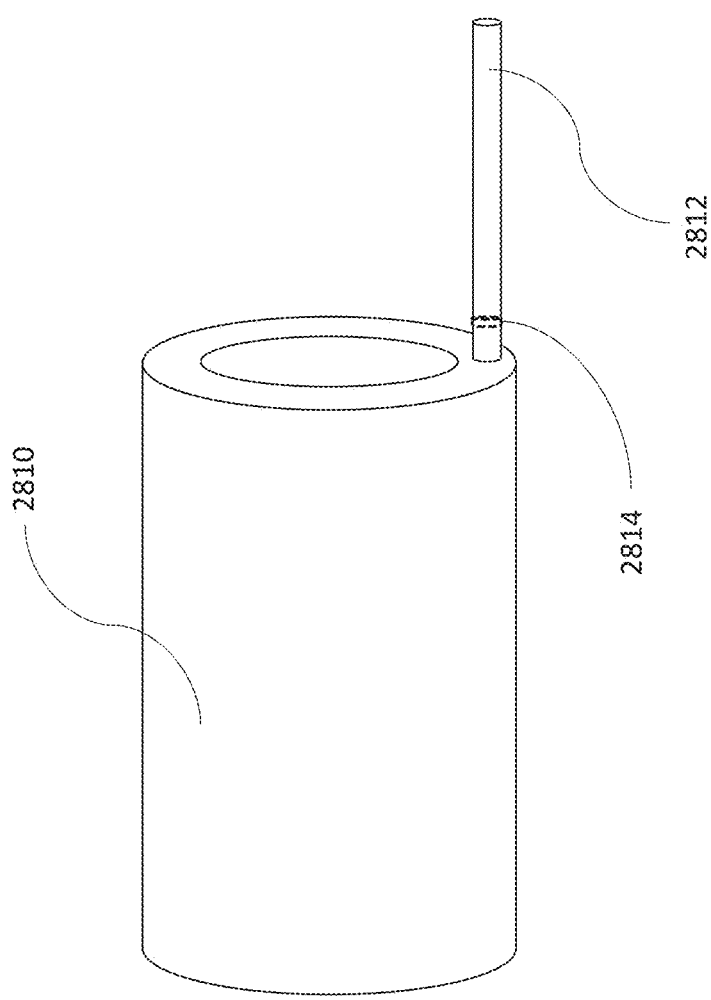
Figure 28C:
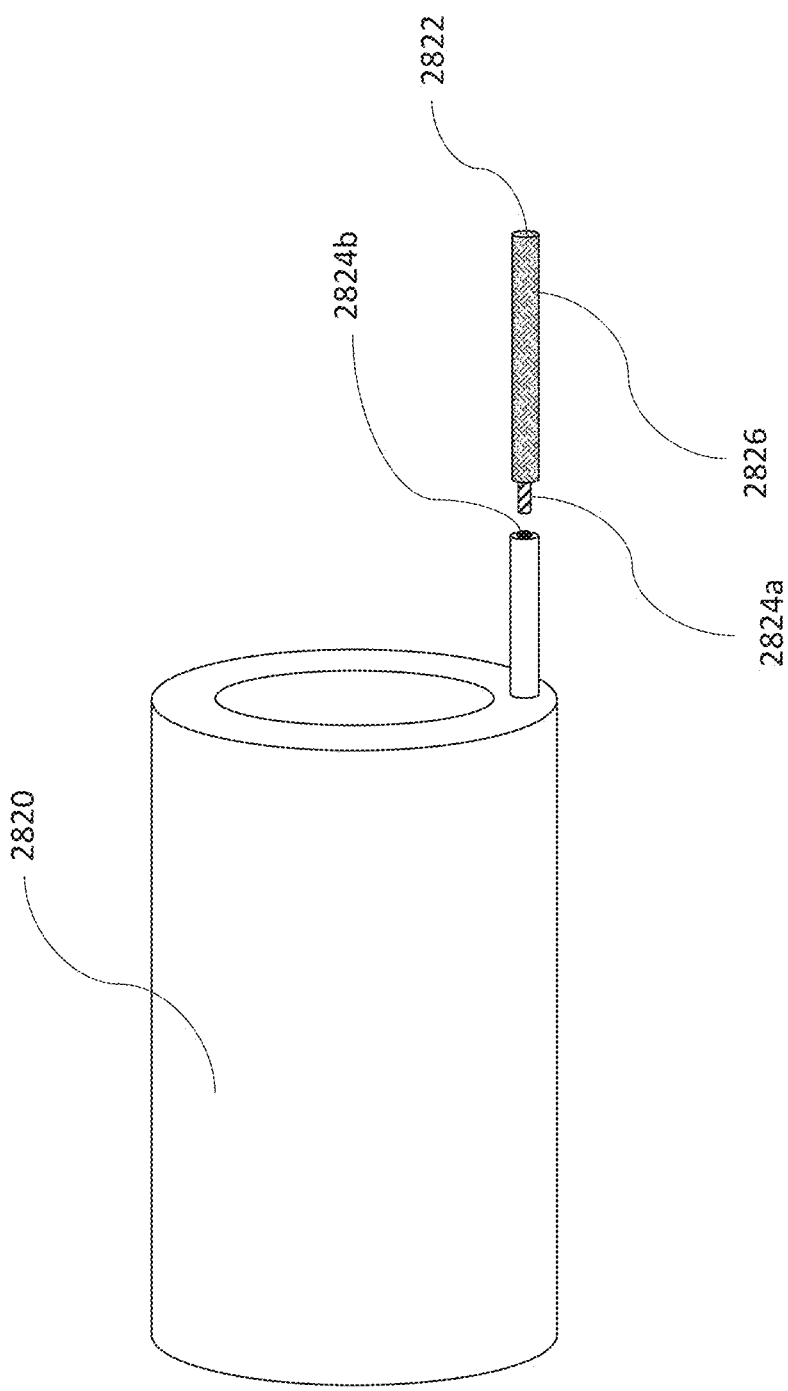

FIGS. 28A, 28B, and 28C are illustrations of detachable connections between an inflatable fill system and a fill tube, in accordance with some illustrative embodiments. FIG. 28A illustrates an inflatable fill structure 2800 with an orifice 2802 configured to accommodate a fill tube 2804. In various embodiments, a hemostasis valve 2806 is placed in the orifice 2802 to seal against a shaft of the fill tube 2804. In various embodiments, the fill tube 2804 is removable. When the fill tube 2804 is removed while in a body, the hemostasis valve 2806 can close, thereby preventing fill medium from escaping from the inflatable fill structure 2800 and interacting with blood. A hemostasis valve may be preferred when the fill medium in the inflatable fill structure does not solidify before the fill tube is removed.

FIG. 28B illustrates an inflatable fill structure 2810 with a fill tube 2812 bonded to the inflatable fill structure 2810. In various embodiments, a designated break location 2814 at an interface between the inflatable fill structure 2810 and the fill tube 2812 is weakened by perforations, reduced wall thickness, etc., such that when pulling, pushing, and/or rotating the fill tube 2812, the material can break at the designated break location 2814 and the fill tube 2812 can separate from the inflatable fill structure 2810.

FIG. 28C illustrates an alternative embodiment of a removable connection between an inflatable fill structure 2820 and a fill tube 2822 including a male-female threaded coupling 2824a and 2824b. The fill tube 2822 can be unscrewed from the inflatable fill structure coupling 2824a by rotating a shaft of the fill tube 2822. In some embodiments, the shaft of the fill tube 2822 (and/or a shaft of the inflatable fill structure 2820) are reinforced with braids or coils 2826, thereby improving torquing of the fill tube 2822 (and/or the shaft of the inflatable fill structure 2820). Removable connections that leave an opening in the inflatable fill structure may be preferred when the fill medium is hardened before removal of the fill tube 2822 or if an opening is desired to allow for continuous exchange of molecules in and out of the inflatable fill structure 2820. For example, free ion exchange between the fill medium and surrounding tissue may be advantageous to avoid an osmotic pressure across a wall of the inflatable fill structure 2820 that may result in swelling or shrinking of the inflatable fill structure 2820.

Figure 29:
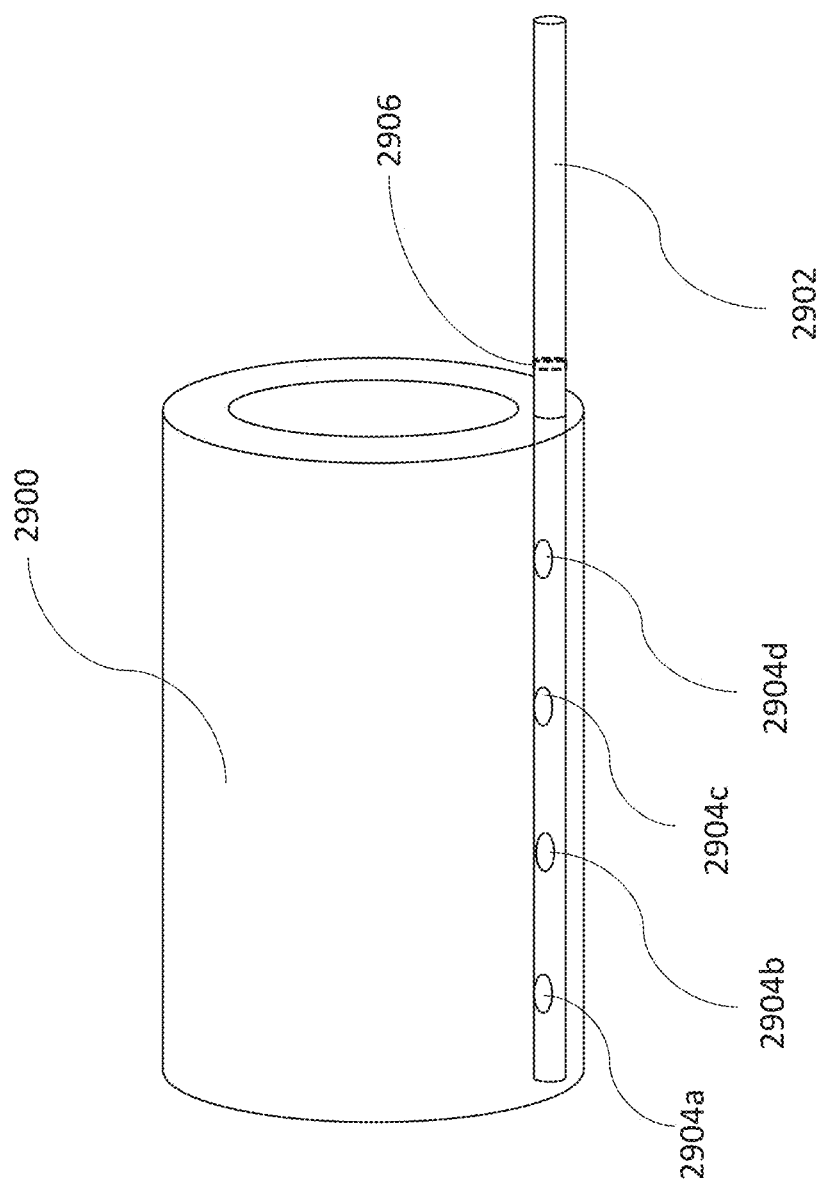
FIG. 29 is an illustration of an aneurysm fill system with a fill line that has multiple injection ports, in accordance with an illustrative embodiment.

FIGS. 29, 30, 31, and 32 illustrate further embodiments of an aneurysm fill system. FIG. 29 is an illustration of an aneurysm fill system with a fill line that has multiple injection ports, in accordance with an illustrative embodiment. In various embodiments, an inflatable fill structure 2900 includes a fill tube 2902 that enters a distal end of the inflatable fill structure 2900 and extends to a proximal end of the inflatable fill structure 2900. In some embodiments, side ports 2904a, 2904b, 2904c, and 2904d are located along a shaft of the fill tube 2902. The side ports 2904a, 2904b, 2904c, and 2904d allow for ejection of fill medium from the fill tube 2902 into the inflatable fill structure 2900. A proximal section of the fill tube 2902 can remain in the inflatable fill structure 2900 when a distal end of the fill tube 2902 is separated from the inflatable fill structure 2900 at a detachment point 2906. In other embodiments, any of the other detachment means described herein may be used. One potential advantage of such an embodiment is that the fill medium can be more evenly distributed along a length of the inflatable fill structure 2900, thereby resulting in more uniform inflation of the inflatable fill structure 2900.

Figure 30:
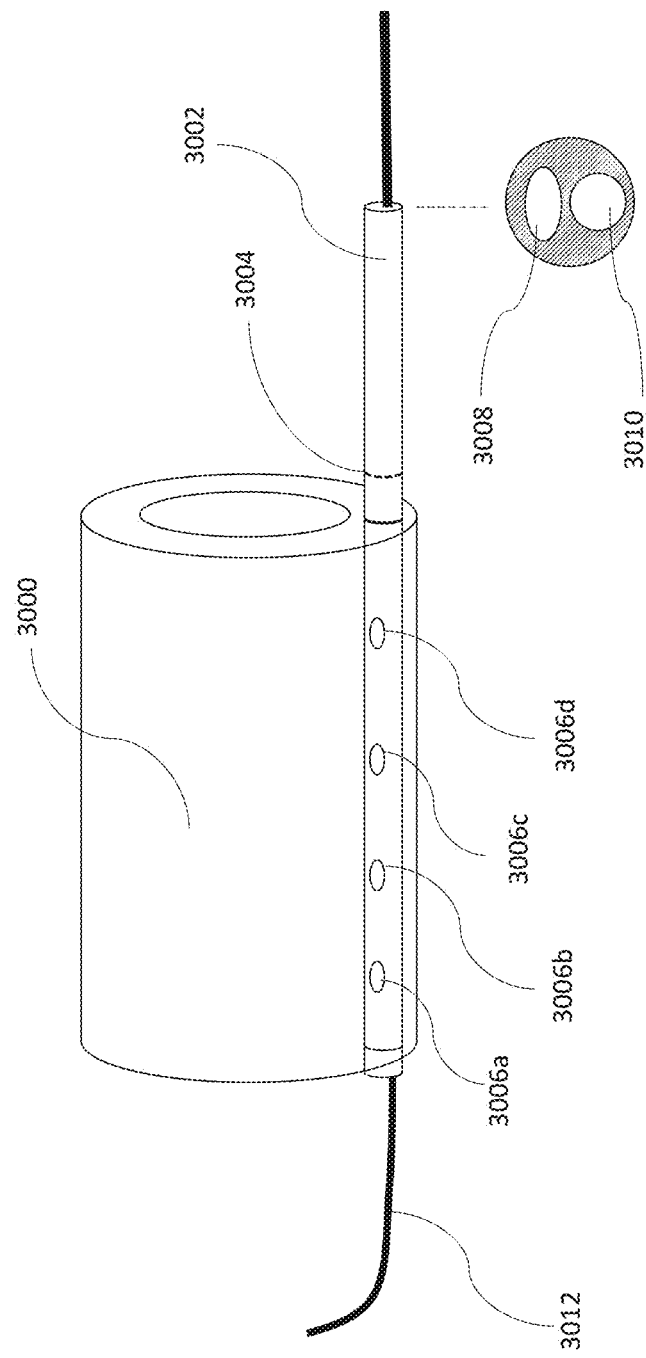
FIG. 30 is an illustration of an aneurysm fill system with a fill line that has a guidewire lumen, in accordance with an illustrative embodiment.

FIG. 30 is an illustration of an aneurysm fill system with a fill line that has a guidewire lumen, in accordance with an illustrative embodiment. In various embodiments, an aneurysm fill system includes an inflatable fill structure 3000 and a detachable fill tube 3002. The detachable fill tube 3002 can have a designated detachment point 3004. In alternative embodiments, any of the detachment means described herein may be used. The detachable fill tube 3002 includes side ports 3006a, 3006b, 3006c, and 3006d that are configured to allow for the flow of fill medium from the fill tube 3002 into the inflatable fill structure 3000. In various embodiments, a fill lumen 3008 and a guide wire lumen 3010 are integrated into a shaft of the fill tube 3002. The guidewire lumen 3010 is configured to accommodate a guidewire 3012. The guidewire 3012 can be used for positioning the aneurysm fill system including the inflatable fill structure 3000 in an aneurysm.

Figure 31:
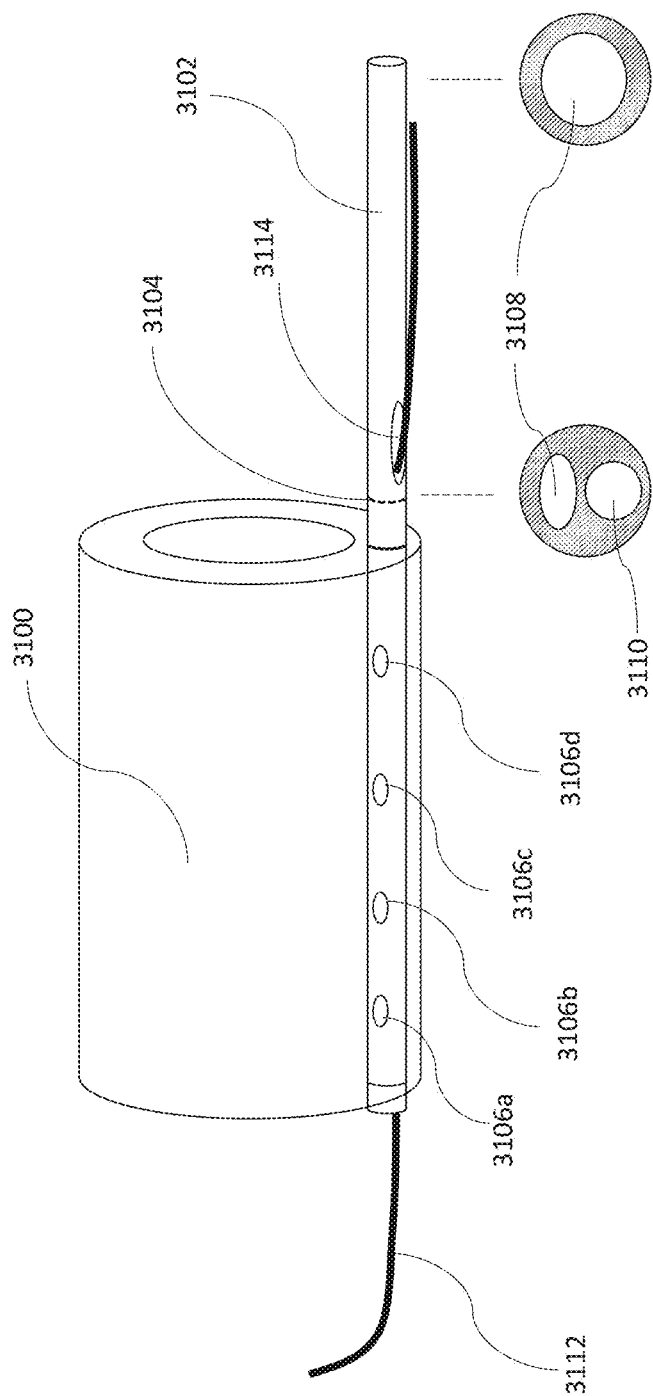
FIG. 31 is an illustration of an aneurysm fill system with a fill line that has a guidewire lumen in a portion therein, in accordance with an illustrative embodiment.

FIG. 31 is an illustration of an aneurysm fill system with a fill line that has a guidewire lumen in a portion therein, in accordance with an illustrative embodiment. In various embodiments, an aneurysm fill system includes an inflatable fill structure 3100 and a detachable fill tube 3102 with a designated detachment point 3104. In alternative embodiments, any of the detachment means described herein may be used. Fill tube 3102 includes side ports 3106a, 3106b, 3106c, and 3106d that are configured to allow for the flow of fill medium from the fill tube 3102 into the inflatable fill structure 3100. In various embodiments, a fill lumen 3108 extends along an entire shaft of the fill tube 3102. In some embodiments, a guidewire lumen 3110 has a distal side opening 3114 configured to accommodate a guidewire 3112, and the guidewire lumen 3110 extends along a proximal section of the shaft of the fill tube 3102. In various embodiments, the guidewire lumen 3110 extends from the distal side opening 3114 through the fill tube 3102 to a proximal side opening, and the guidewire 3112 passes through the guidewire lumen 3110. The guidewire 3112 can be used for positioning the aneurysm fill system in an aneurysm. Such an embodiment can be termed a "mono-rail" configuration of the guidewire lumen 3110. Such an embodiment can allow for a larger fill lumen 3108 along a distal segment of the fill tube 3102. This embodiment may be preferred when highly viscous fill medium is used and/or low injection forces are desired.

FIG. 32 is an illustration of an aneurysm fill system with a separate guidewire lumen and fill tube, in accordance with an illustrative embodiment. An aneurysm fill system can be configured to maximize the size of the fill lumen. In various embodiments, an aneurysm fill system includes an inflatable fill structure 3200 and a detachable fill tube 3202 with a designated detachment point 3204. In alternative embodiments, any of the detachment means described herein may be used. In various embodiments, the aneurysm fill system further includes a separate guidewire lumen 3206. The guidewire lumen 3206 extends along a length of a wall of the inflatable fill structure 3200. In some embodiments, the guidewire lumen 3206 is mounted internally to the inflatable fill structure 3200. In other embodiments, the guidewire lumen 3206 can be mounted externally to the inflatable fill structure 3200. In yet other embodiments, the guidewire lumen 3206 can be integral to a wall of the inflatable fill structure 3200. A guidewire 3212 can be passed through the guidewire lumen 3206.

FIGS. 33A and 33B are illustrations of a multi-compartment aneurysm fill system, in accordance with an illustrative embodiment. FIG. 33A shows an example of an aneurysm fill system including an inflatable fill structure 3300 with individually fillable compartments 3302a, 3302b, and 3302c. In some embodiments, the individually fillable compartments 3302a, 3302b, and 3302c are the same or substantially similar sizes (e.g., fill volume, length) as each other. In other embodiments, the individually fillable compartments 3302a, 3302b, and 3302c have one or more different sizes (e.g., fill volume, length) that each other. In various embodiments, the inflatable fill structure 3300 includes multiple axially adjacent individual compartments, such as the individually fillable compartments 3302a, 3302b, and 3302c.

In various embodiments, an outer fill tube 3304 extends from a distal end to a proximal end of the inflatable fill structure 3300. In some embodiments, the outer fill tube 3304 is sealed against walls of the individually fillable compartments 3302a, 3302b, and 3302c. In various embodiments, the outer fill tube 3304 includes side ports 3306a, 3306b, and 3306c that allow for the flow of fill medium into the individually fillable compartments 3302a, 3302b, and 3302c, respectively, via the outer fill tube 3304. In some embodiments, an inner fill tube 3308 is placed coaxially within the outer fill tube 3304. The inner fill tube 3308 is slideable axially along the outer fill tube 3304. The inner fill tube 3308 has a proximal opening 3310 configured to allow for the flow of fill medium into the outer fill tube 3304.

FIGS. 33A and 33B illustrate a sequential filling of the individually fillable compartments 3302a, 3302b, and 3302c of the inflatable fill structure 3300. In FIG. 33A, the proximal end of the inner fill tube 3308 having the proximal opening 3310 can be placed within the first compartment 3302a such that fill medium (illustrated with an arrow) can flow through the inner fill tube 3308 and enter the first individually fillable compartment 3302a through the side port 3306a in the outer fill tube 3304. The side ports 3306b and 3306c, corresponding to the other individually fillable compartments 3302b and 3302c, respectively, can be blocked by the shaft of the inner fill tube 3308 during the filling of the first individually fillable compartment 3302a. In FIG. 33B the first individually fillable compartment 3302a is shown after it has been filled with fill medium 3312 through the side port 3306a. The inner fill tube 3308 can then be pulled back to expose side port 3306b of the outer fill tube 3304 to the second individually fillable compartment 3302b, as illustrated in FIG. 33B, such that fill medium can pass from the inner fill tube 3308 to the second individually fillable compartment 3302b. The process can be repeated to fill the second individually fillable compartment 3302b, and then the inner fill tube 3308 can be moved to allow for filling the third individually fillable compartment 3302c through the side port 3306c. Such sequential filling may be preferred in bilobed aneurysms with lumen narrowing between the lopes or aortic-iliac aneurysms with a narrow bifurcation.

In some embodiments, the inner fill tube 3308 includes an end cap on a proximal end of the inner fill tube 3308. The end cap can prevent fill material from flowing out of the proximal end of the inner fill tube 3308. In such an embodiment, fill material can be configured to flow only through a side hole (not illustrated) of the inner fill tube 3308. In such an embodiment, fill material can flow into one of the individually fillable compartments 3302a, 3302b, 3302c when the side hole of the inner fill tube 3308 is aligned with the corresponding side port 3306a, 3306b, 3306c. In such an embodiment, the individually fillable compartments 3302a, 3302b, and 3302c can be filled in any desired order (e.g., 3302c, then 3302a, then 3302b).

FIGS. 34A, 34B, 34C, 34D, 34E, and 34F are illustrations of a distal end of a delivery catheter 3406 housing an aneurysm fill system 3400, in accordance with an illustrative embodiment. FIG. 34A shows a cross-sectional view and FIG. 34B shows a side view of a proximal section of the distal end of the delivery catheter 3406. With reference to FIGS. 34A and 34B, in various embodiments, the aneurysm fill system 3400 includes a toroid-shaped inflatable fill structure 3402 and a detachable fill tube 3404. In various embodiments, the delivery catheter 3406 includes a pusher 3408, a central shaft 3410, a guidewire lumen 3412, a dilator tip 3414, and an outer sheath 3416. In some embodiments, additional or fewer elements may be used. The outer sheath 3416 is configured to constrain at least a portion of the aneurysm fill system 3400. The aneurysm fill system 3400 can be loaded into the catheter 3406 with the central shaft 3410 passing through a central passage 3418 of the toroid-shaped inflatable fill structure 3402. FIGS. 34A and 34B show an arbitrary collapsed shape of the toroid-shaped inflatable fill structure 3402. Various embodiments can have different methods of collapsing the toroid-shaped inflatable fill structure 3402. In some embodiments, the inflatable fill structure 3402 can be collapsed in a way that minimizes a profile of the inflatable fill structure 3402. For example, the toroid-shaped inflatable fill structure 3402 may be rolled or folded. In another example, the toroid-shaped inflatable fill structure 3402 may be inflated with a gas and then gradually compressed in a radial crimper to uniformly compress the walls of toroid-shaped inflatable fill structure 3402.

Figure 34G:
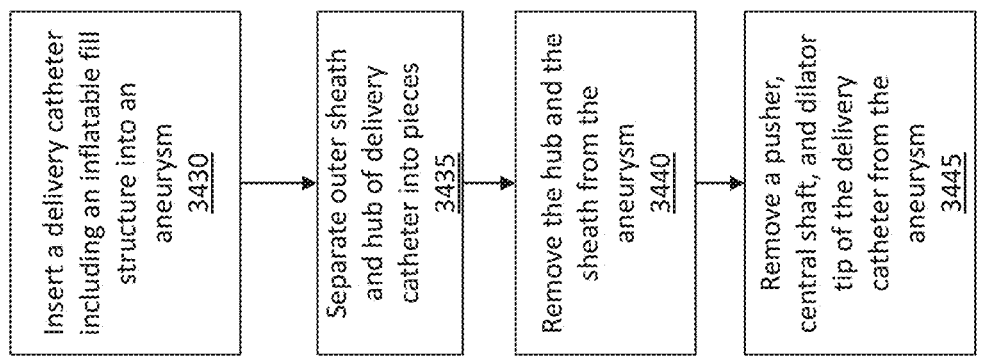
FIG. 34G is a flow diagram illustrating a method of delivering an aneurysm fill system with a catheter, in accordance with an illustrative embodiment.

FIGS. 34C and 34D illustrate a distal segment of the distal end of the delivery catheter 3406 of FIG. 34B. FIG. 34G is a flow diagram illustrating a method of delivering the aneurysm fill system 3400 with the delivery catheter 3406 of FIG. 34B, in accordance with an illustrative embodiment. With reference to FIGS. 34B, 34C, 34D, and 34G, in step 3430, the delivery catheter 3406 with the inflatable fill structure 3402 is inserted into an aneurysm. In various embodiments, the outer sheath 3416 of the delivery catheter 3406 is connected to a hub 3420 that houses a hemostasis valve 3422. The hemostasis valve 3422 can create a seal against the pusher 3408. The fill tube 3404 can sit in an open lumen 3424 in the pusher 3408. In various embodiments, a Luer lock 3426 is bonded to a distal end of the fill tube 3404 to fluidly connect the fill tube 3404 to a reservoir containing fill medium. The outer sheath 3416 and the hub 3420 can have a tear-away feature configured to assist in removing the delivery catheter 3406 from a body of a patient. The tear-away feature is illustrated in FIGS. 34E and 34F. With reference to FIGS. 34D, 34E, 34F, and 34G, in step 3435, the outer sheath 3416 and the hub 3420 are separated into two half-circular pieces 3421a and 3421b along longitudinal tear-away lines. Peeling open the outer sheath 3416 and hub 3420 assists in removal of the outer sheath 3416 and hub 3420 while leaving the fill tube 3404 with the Luer lock 3426 in place. In step 3440, the hub 3420 and the outer sheath 3416 are removed from the aneurysm. In step operation 3445, the pusher 3408 with the lumen 3424, the central shaft 3410, and the dilator tip 3414 are retracted from the patient while leaving a guidewire 3428 in place.

FIGS. 35A, 35B, and 35C are illustrations of a distal end of a delivery catheter housing an aneurysm fill system, in accordance with an illustrative embodiment. The distal end of the delivery catheter includes a pusher 3500 with a central guidewire lumen 3502, an outer sheath 3504, a hub 3506 housing a hemostasis valve 3508, and an open lumen 3510 in the pusher 3500 for housing a fill tube 3514. In various embodiments, a distal end of the fill tube 3514 has a low-profile male thread 3518. In other embodiments, other mating surfaces can be used. To remove the delivery catheter from a patient, the outer sheath 3504 and the pusher 3500 can be pulled back over a guidewire 3520 while leaving the fill tube 3514 and the guidewire 3520 in place. Once the delivery catheter is removed, a Luer-lock 3522 with a female thread can be connected to the male thread 3518 of the fill tube 3514.

FIGS. 36A and 36B are illustrations of a delivery catheter housing an aneurysm fill system, in accordance with an illustrative embodiment. FIG. 36A illustrates a cross-section of the delivery catheter and FIG. 36B illustrates a side view. With reference to FIGS. 36A and 36B, in various embodiments the aneurysm fill system includes an inflatable fill structure 3600 and a removable fill tube 3602 that has a fill lumen 3603 and a guidewire lumen 3605. A guidewire 3607 can be placed through a central passage 3601 of the inflatable fill structure 3600. In various embodiments, a sleeve 3604 with a tear-way feature 3606 retains the inflatable fill structure 3600. The tear-away feature 3606 can include, for example, a line of perforations on the sleeve 3604. In some embodiments, the sleeve 3604 may be made from a polymer material such as, for example, polytetrafluoroethylene (PTFE), polyurethane, polypropylene, or polyethylene. In some embodiments, the sleeve 3604 may be slipped onto the inflatable fill structure 3600. In some embodiments, the sleeve 3604 can be shrunk onto the inflatable fill structure 3600 by applying heat. In various embodiments, a release cord 3608 is passed through the perforations of the tear-away feature 3606, and the inflatable fill structure 3600 can be released by pulling on the release cord 3608. The release cord 3608 can tear open the sleeve 3604 along the perforation line of the tear-away feature 3606. In some embodiments, the sleeve 3604 may be left in the aneurysm sac or removed from the body by attaching a distal end of the sleeve 3604 to the release cord 3608. In some embodiments, the sleeve 3604 is bonded to the inflatable fill structure 3600, or is an integral part of the inflatable fill structure 3600. As an alternative to the release cord 3608, the sleeve 3604 may be torn open along the perforation line of the tear-away feature 3606 by filling the inflatable fill structure 3600 with a fluid in order to apply pressure to the perforation until it tears.

Figure 37G:
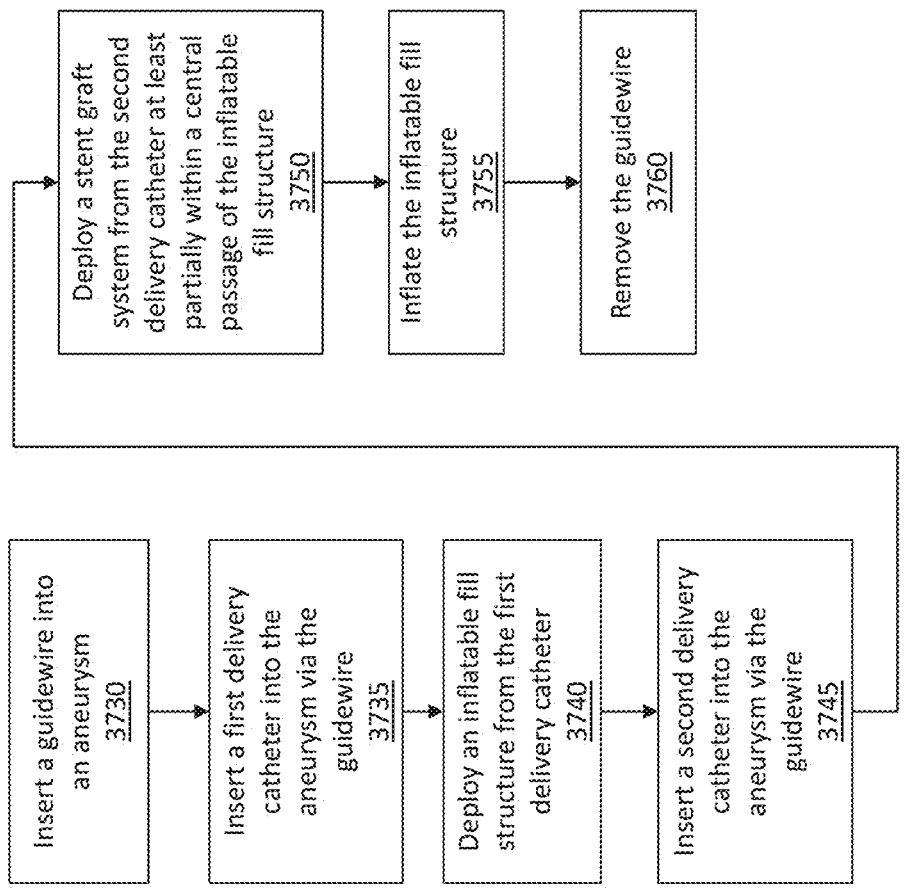
FIG. 37G is a flow diagram illustrating a method of deploying an aneurysm fill system with two catheters and one guidewire, in accordance with an illustrative embodiment.

FIGS. 37A, 37B, 37C, 37D, 37E, and 37F are illustrations showing some steps during implantation of an aneurysm fill system, in accordance with an illustrative embodiment. In various embodiments, the implantation through an ipsilateral iliac artery 3702 into an aneurysm 3706 of an aorta 3704 is accomplished using a guidewire 3700. FIG. 37G is a flow diagram illustrating a method of deploying an aneurysm fill system with two catheters, in accordance with an illustrative embodiment. With reference to FIGS. 37A and 37G, in step 3730, the guidewire 3700 is inserted into the aneurysm 3706. In various embodiments, the guidewire 3700 is inserted from a femoral artery through the ipsilateral iliac artery 3702 into the aorta 3704 proximal to the aneurysm 3706. In other embodiments, other aneurysms can be repaired and other paths can be used. In step 3735, a delivery catheter 3708 housing an aneurysm fill system is inserted into the aneurysm 3706 by passing the delivery catheter 3708 over the guidewire 3700.

With reference to FIGS. 37A, 37B, and 37G, in step 3740, an inflatable fill structure 3710 is released from the delivery catheter 3708. The delivery catheter 3708 can be withdrawn from the body, for example, using a similar method for removing a delivery catheter as described above with regard to FIGS. 34D, 34E, and 34F. FIG. 37B shows the released aneurysm fill system with the inflatable fill structure 3710 in the aneurysm 3706 and a fill tube 3712 connected to the inflatable fill structure 3710. The guidewire 3700 passes through a central passage 3714 of the inflatable fill structure 3710. With reference to FIGS. 37C and 37G, in step 3745, a delivery catheter 3716 housing a stent graft system is inserted into the aneurysm 3706. In various embodiments, the delivery catheter 3716 is advanced over the guidewire 3700 and through the central passage 3714 of the inflatable fill structure 3710. The delivery catheter 3716 can be placed while the fill tube 3712 remains attached to the inflatable fill structure 3710. With reference to FIGS. 37C, 37D, and 37G, in step 3750, a stent graft system 3718 is deployed from the delivery catheter 3716. In various embodiments, the stent graft system 3718 comprises a stent graft. In various embodiments, the stent graft system 3718 is deployed within the central passage 3714 of the inflatable fill structure 3710. The stent graft system 3718 can exclude the aneurysm 3706. In various embodiments, the fill tube 3712 passes external to an ipsilateral leg 3720 of the stent graft system 3718 to the inflatable fill structure 3710.

With reference to FIGS. 37E and 37G, in step 3755, the inflatable fill structure 3710 is filled with fill medium 3722 through the fill tube 3712. In various embodiments, the filled inflatable fill structure 3710 can conform to an inner wall of the aneurysm 3706 and to an outer surface of the stent graft system 3718 and can substantially fill the aneurysm sac. The fill tube 3712 can be separated from the inflatable fill structure 3710 and removed from the body. With reference to FIGS. 37E, 37F and 37G, in step 3760, the guidewire 3700 can be removed from the body. FIG. 37F shows the completed aneurysm repair with the stent graft system 3718 excluding the aneurysm 3706 and the filled inflatable fill structure 3710 filling the aneurysm space.

Figure 38C:
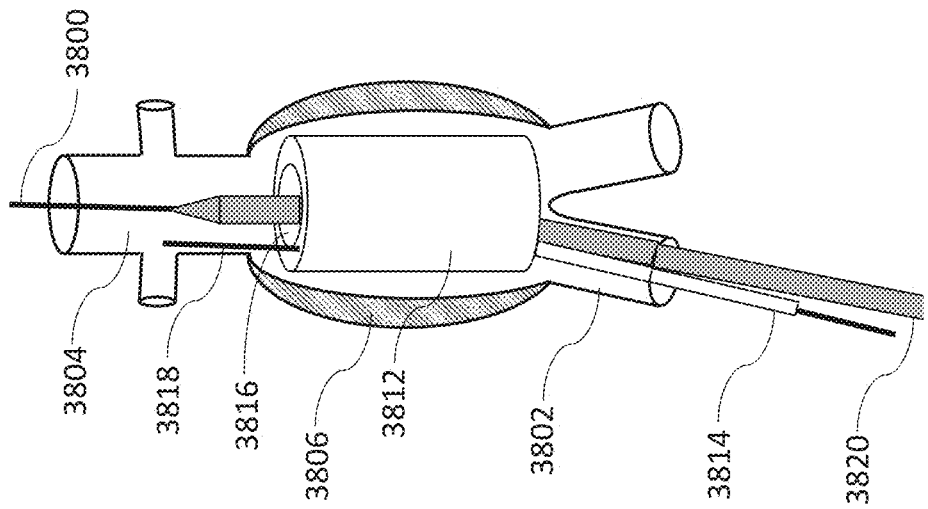
FIGS. 38A, 38B, 38C, 38D, 38E, and 38F are illustrations showing some steps during implantation of an aneurysm fill system, in accordance with an illustrative embodiment.
Figure 38B:
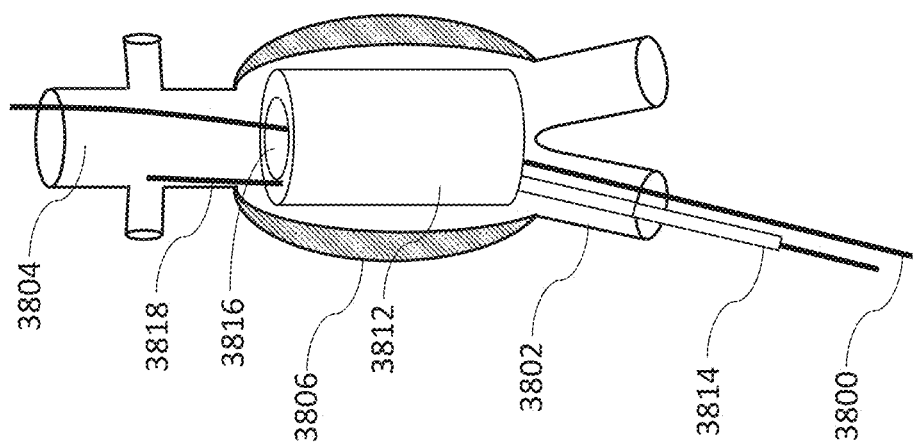
Figure 38A:
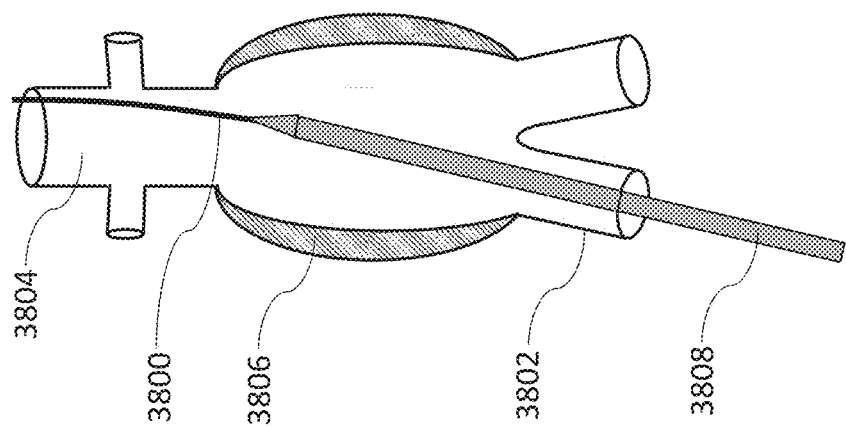
Figure 38F:
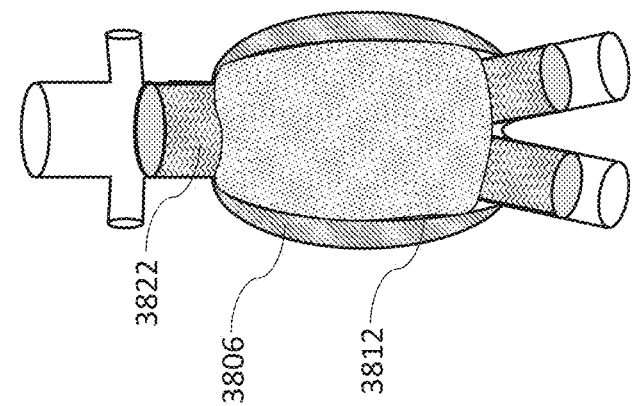
Figure 38E:
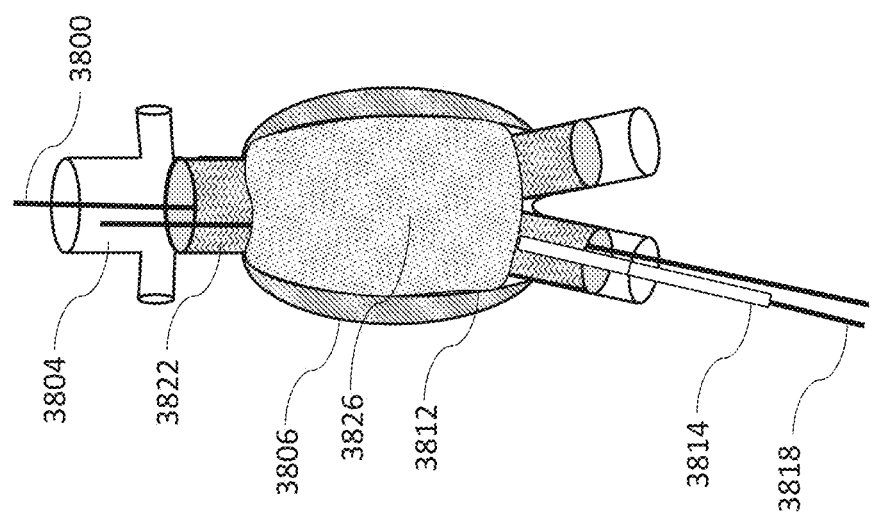
Figure 38D:
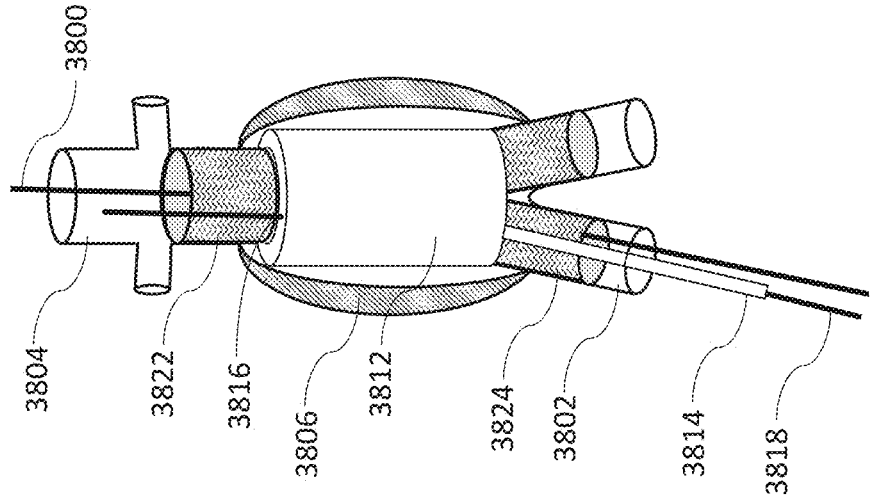
Figure 38G:
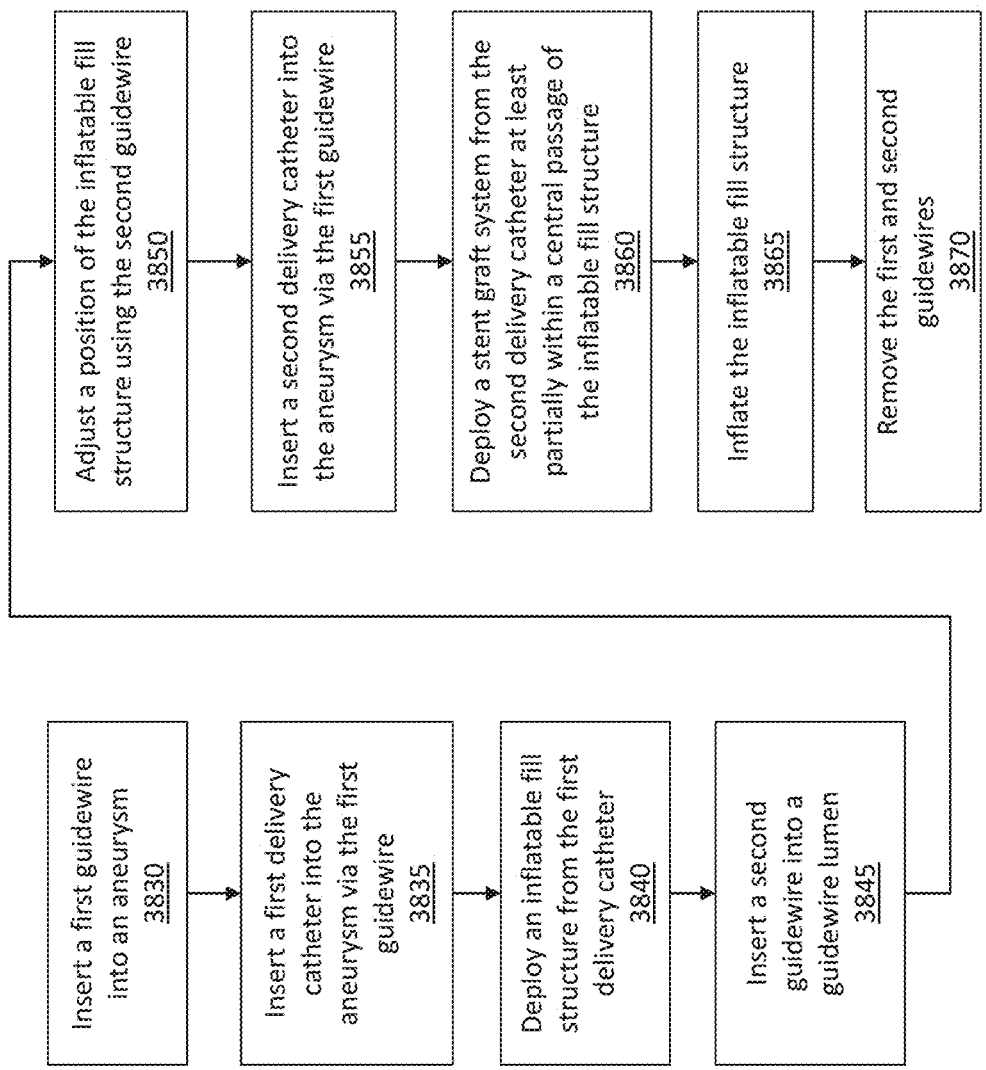
FIG. 38G is a flow diagram illustrating a method of deploying an aneurysm fill system with two guidewires, in accordance with an illustrative embodiment.

FIGS. 38A, 38B, 38C, 38D, 38E, and 38F are illustrations showing some steps during implantation of an aneurysm fill system, in accordance with an illustrative embodiment. In various embodiments, the implantation through an ipsilateral iliac artery 3802 into an aneurysm 3806 of an aorta 3804 is accomplished using a first guidewire 3800 and a second guidewire 3818. FIG. 38G is a flow diagram illustrating a method of deploying an aneurysm fill system with two guidewires, in accordance with an illustrative embodiment. With reference to FIGS. 38A and 38G, in step 3830, a first guidewire 3800 is inserted into the aneurysm 3806. In an illustrative embodiment, the first guidewire 3800 can be inserted from the femoral artery through the ipsilateral iliac artery 3802 and into the aorta 3804 proximal to the aneurysm 3806. In alternative embodiments, different aneurysms can be repaired, and different paths may be used. In step 3835, a delivery catheter 3808 housing an aneurysm fill system is passed over the first guidewire 3800 and into the aneurysm 3806. With reference to FIGS. 38A, 38B, and 38G, in step 3840, an inflatable fill structure 3812 is released from the delivery catheter 3808 in the aneurysm 3806. The delivery catheter 3808 can be retracted from the aneurysm 3806, for example, using a similar method for removing a delivery catheter as described above with regard to FIGS. 34D, 34E, and 34F.

FIG. 38B illustrates the released aneurysm fill system with the inflatable fill structure 3812 unconstrained. The first guidewire 3800 can pass through a lumen or central passage 3816 of the inflatable fill structure 3812. A fill tube 3814 can be connected to the inflatable fill structure 3812. With reference to FIGS. 38B and 38G, in step 3845, the second guidewire 3818 is passed through a guidewire lumen in a shaft of the fill tube 3814 that extends along a length of the inflatable fill structure 3812. In step 3850, the second guidewire 3818 is used to adjust a position of the inflatable fill structure 3812 within the aneurysm 3806. With reference to FIGS. 38C and 38G, in step 3855, a delivery catheter 3820 housing a stent graft system is advanced over the first guidewire 3800 through the central passage 3816 of the inflatable fill structure 3812. In various embodiments, the fill tube 3814 remains while the delivery catheter 3820 is inserted. With reference to FIGS. 38C, 38D, and 38G, in step 3860, a stent graft system 3822 is deployed from the delivery catheter 3820 at least partially within the central passage 3816 of the inflatable fill structure 3812. In various embodiments, the stent graft system 3822 comprises a stent graft. The second delivery catheter 3820 can then be removed.

FIG. 38D illustrates the deployed stent graft system 3822. The stent graft system 3822 can exclude the aneurysm 3806. The second guidewire 3818 can be pinned against the aorta 3804 by a proximal segment of the stent graft system 3822. In various embodiments, the fill tube 3814 passes external to an ipsilateral leg 3824 of the stent graft system 3822 to the inflatable fill structure 3812. With reference to FIGS. 38E and 38G, in step 3865, the inflatable fill structure 3812 is filled with fill medium 3826 through the fill tube 3814. In various embodiments, the filled inflatable fill structure 3812 conforms to an inner wall of the aneurysm 3806 and to an outer surface of the stent graft system 3822, and the inflatable fill structure 3812 substantially fills the aneurysm sac. The fill tube 3814 can then be separated from the inflatable fill structure 3812. In step 3870, the first and second guidewires 3800 and 3818 are removed from the body. In an illustrative embodiment, the fill tube 3814 can be removed together with the second guidewire 3818 from the body. In such an embodiment, the first guidewire 3800 can be removed after the procedure is completed. FIG. 38F shows the completed aneurysm repair with the stent graft system 3822 excluding the aneurysm 3806 and the inflated or filled inflatable fill structure 3812 filling the aneurysm space.

In various embodiments, a guidewire placed through a central passage of an inflatable fill structure guides a delivery catheter of a stent graft system through the central passage. In some embodiments, a stent graft system may be delivered from a contralateral iliac artery, which may require cannulation of the central passage of the inflatable fill structure from the contralateral side with a third guidewire.

Figure 39:
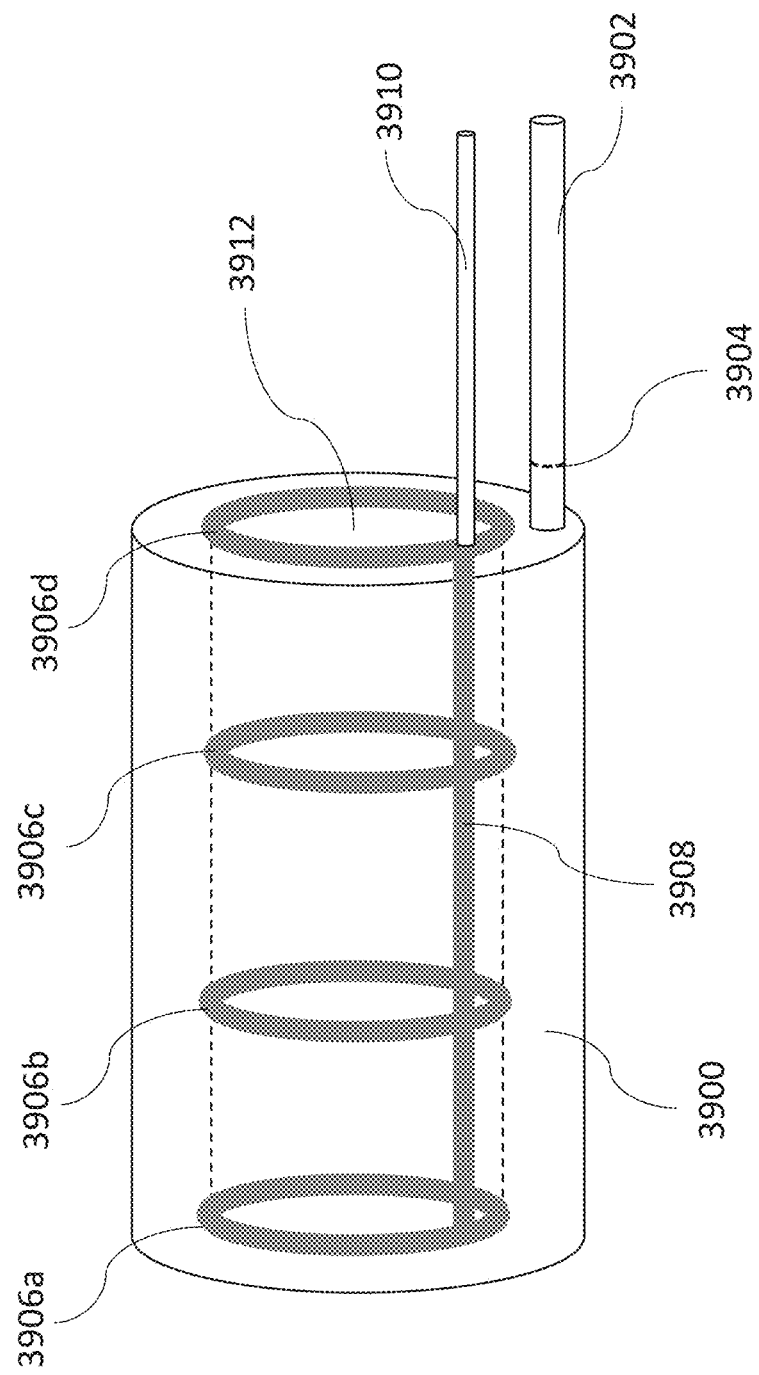
FIG. 39 is an illustration of an aneurysm fill system with an inflatable, radially expandable scaffold, in accordance with an illustrative embodiment.

FIG. 39 is an illustration of an aneurysm fill system with an inflatable, radially expandable scaffold, in accordance with an illustrative embodiment. In various embodiments, the aneurysm fill system has a feature to assist with the cannulation of a central passage of an inflatable fill structure. In various embodiments, an aneurysm fill system includes a toroidal shaped inflatable fill structure 3900 and a fill tube 3902 connected to the inflatable fill structure 3900. In some embodiments, the fill tube 3902 has a designated detachment point 3904. In alternative embodiments, any of the detachment mechanisms described herein may be used.

In various embodiments, the aneurysm fill system further includes ring-shaped inflatable fill elements 3906a, 3906b, 3906c, and 3906d at an inner wall of the inflatable fill structure 3900. The ring-shaped inflatable fill elements 3906a, 3906b, 3906c, and 3906d can be in fluid communication with each other through an axial channel 3908. In various embodiments, a second fill tube 3910 supplies fill medium to the ring-shaped inflatable fill elements 3906a, 3906b, 3906c, and 3906d. When fill medium is injected into the ring-shaped inflatable fill elements 3906a, 3906b, 3906c, and 3906d, the ring-shaped inflatable fill elements 3906a, 3906b, 3906c, and 3906d form a support scaffold and radially expand a central passage 3912 of the inflatable fill structure 3900.

Figure 40C:
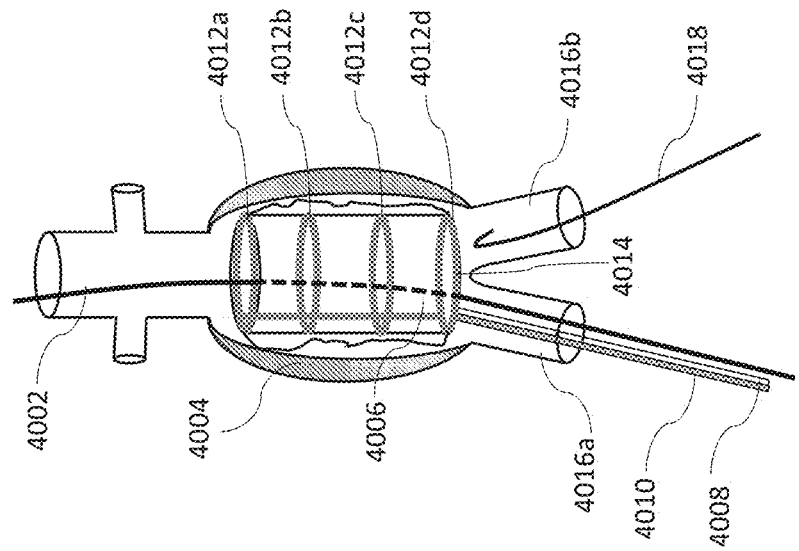
FIGS. 40A, 40B, and 40C are illustrations showing some steps during implantation of an aneurysm fill system containing an inflatable, radially expandable scaffold, in accordance with an illustrative embodiment.
Figure 40B:
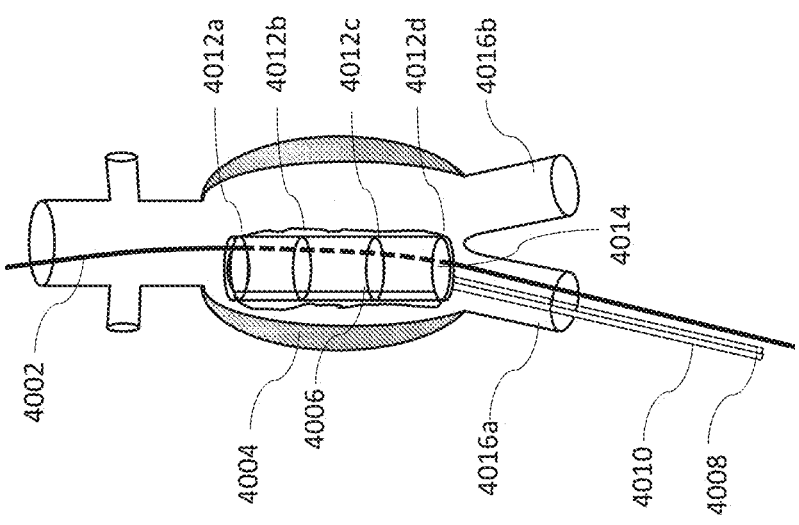
Figure 40A:
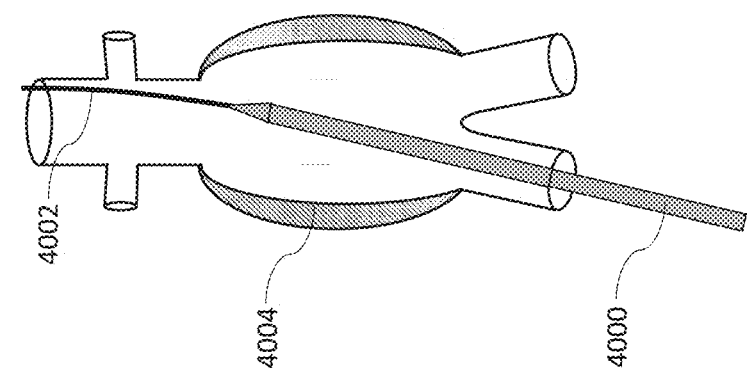
Figure 40D:
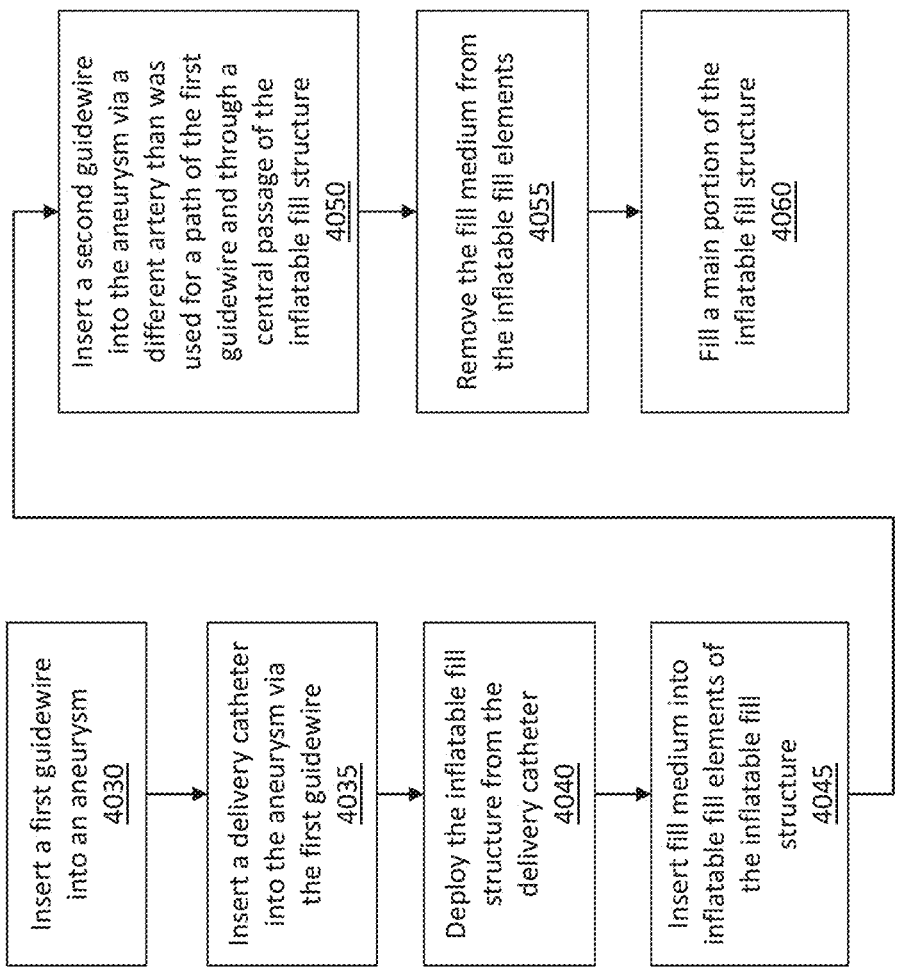
FIG. 40D is a flow diagram illustrating a method of implementing an aneurysm fill system containing an inflatable, radially expandable scaffold, in accordance with an illustrative embodiment.

FIGS. 40A, 40B, and 40C are illustrations showing some steps during implantation of an aneurysm fill system including an inflatable, radially expandable scaffold, in accordance with an illustrative embodiment. FIG. 40D is a flow diagram illustrating a method of implanting an aneurysm fill system including an inflatable, radially expandable scaffold, in accordance with an illustrative embodiment. With reference to FIGS. 40A and 40D, in step 4030, a first guidewire 4002 is inserted into an aneurysm 4004. In step 4035, a delivery catheter 4000 is inserted into the aneurysm 4004 via the first guidewire 4002. FIG. 40A shows the delivery catheter 4000, which houses an aneurysm fill system (e.g., the aneurysm fill system illustrated in FIG. 39), being advanced over the first guidewire 4002 into the aneurysm 4004. With reference to FIGS. 40A, 40B, and 40D, in step 4040, an inflatable fill structure 4006 of the aneurysm fill system is released from the delivery catheter 4000 in the aneurysm 4004. In various embodiments, a first fill tube 4008 is connected to the inflatable fill structure 4006. In various embodiments, the inflatable fill structure 4006 includes inflatable fill elements 4012a, 4012b, 4012c, and 4012d, and a second fill tube 4010 is connected to the inflatable fill elements 4012a, 4012b, 4012c, and 4012d. In some instances, a distal end of a central passage 4014 of the inflatable fill structure 4006 might be narrow and biased toward an ipsilateral iliac artery 4016a, which may make cannulation of the central passage 4014 from a contralateral iliac artery 4016b difficult. To assist with the cannulation, fill medium can be injected through the second fill tube 4010 into the inflatable fill elements 4012a, 4012b, 4012c, and 4012d, thereby expanding the central passage 4014. The first guidewire 4002 can also extend through the central passage 4014.

With reference to FIGS. 40C and 40D, in step 4045, fill medium is inserted into the inflatable fill elements 4012a, 4012b, 4012c, and 4012d of the inflatable fill structure 4006 through the second fill tube 4010. The fill medium may be, for example, a gas or a liquid. In some embodiments the fill medium may be, for example, a liquid such as saline. In some embodiments, contrast medium may be added to the fill medium to visualize the inflatable fill elements under fluoroscopy. In step 4050, a second guidewire 4018 that is separate from the first guidewire 4002 is inserted into the aneurysm 4004. The second guidewire 4018 can be advanced from a different path than was used by the first guidewire 4002, such as through a contralateral iliac artery 4016b rather than through the ipsilateral iliac artery 4016a. The second guidewire 4018 can be inserted through the central passage 4014 in preparation for placement of a stent graft system across the aneurysm 4004 using the second guidewire 4018. In step 4055, the fill medium can be withdrawn from the inflatable fill elements 4012a, 4012b, 4012c, and 4012d. In step 4060, a main portion of the inflatable fill structure 4006 is inflated or filled using the first fill tube 4008 such that a wall of the inflatable fill structure 4006 conforms to a wall of the aneurysm 4004. In some embodiments, the fill medium can be withdrawn from the inflatable fill elements 4012a, 4012b, 4012c, and 4012d through the second fill tube 4010 prior to the filling of the main portion of the inflatable fill structure 4006 through the first fill tube 4008. The second fill tube 4010 can removed along with the first fill tube 4008.

Figure 41:
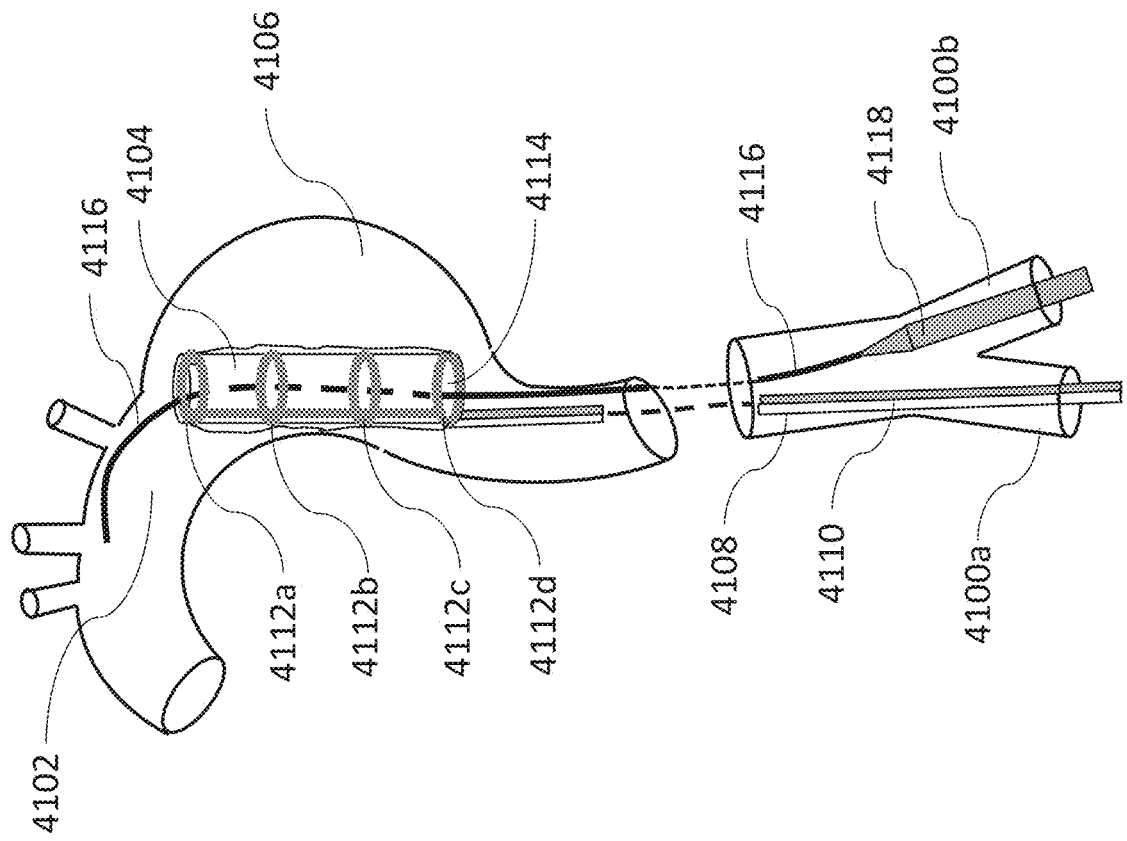
FIG. 41 is an illustration of an aneurysm fill system with an inflatable scaffold at least partially across a thoracic aneurysm, in accordance with an illustrative embodiment.

FIG. 41 is an illustration of an aneurysm fill system with an inflatable scaffold at least partially across a thoracic aneurysm, in accordance with an illustrative embodiment. In an illustrative embodiment, the aneurysm fill system can be advanced from an ipsilateral side 4100a to a thoracic aorta 4102. In various embodiments, an inflatable fill structure 4104 is released into an aneurysm 4106. In various embodiments, a first fill tube 4108 is connected to the inflatable fill structure 4104. In some embodiments, a second fill tube 4110 is connected to inflatable fill elements 4112a, 4112b, 4112c, and 4112d that allow for forming an inflatable scaffold in the inflatable fill structure 4104. The inflatable fill elements 4112a, 4112b, 4112c, and 4112d can be inflated will fill medium through a second fill tube 4110 to expand a central passage 4114 of the inflatable fill structure 4104. Expansion of the central passage 4114 can facilitate passage of a guidewire 4116 from, for example, a contralateral side 4100b. A delivery catheter 4118 housing a thoracic stent graft system including a stent graft can be advanced over the guidewire 4116, and the stent graft can be placed at least partially within the inflatable fill structure 4104. This bilateral approach allows a user, for example, to keep a delivery catheter of an aneurysm fill structure in an ipsilateral access vessel providing continuous hemostasis and access while placing a stent graft system from the contralateral side.

In an alternative approach to contralateral placement of an aneurysm fill structure described in FIG. 41, an aneurysm fill structure may be advanced into an aorta from another avenue, for example via an arm vessel or one of the head vessels branching from the thoracic aorta. In another alternative embodiment, a guidewire may be advanced from a branch vessel distal to the aneurysm and externalized at a branch vessel proximal to the aneurysm using snaring techniques. The proximal branch vessel may be, for example, the radial artery, the subclavian artery, or any other branch vessel to the head or arm. The distal branch artery may be an iliac artery or a femoral artery. The aneurysm fill system described in relation to FIG. 30 can be advanced, for example, from a distal branch vessel over a guidewire into an aneurysm. The aneurysm fill structure can be inserted over the guidewire with the fill tube 3002 ahead of the inflatable fill structure 3000. The end of the fill tube 3002 can be externalized from the body at a proximal branch vessel. The inflatable fill structure 3000 can be filled from the proximal branch vessel access point. One advantage of this approach is that the proximal placement of the fill tube 3002 does not interfere with the placement of a stent graft within at least a portion of the inflatable fill structure 3000 from the distal access point.

FIGS. 42A and 42B are illustrations of an aneurysm fill system with self-expanding structures, in accordance with an illustrative embodiment. In various embodiments, an aneurysm fill system includes a toroid-shaped inflatable fill structure 4200, a fill tube 4202, and radially self-expanding structures 4204a, 4204b, 4204c, and 4204d along a central passage 4206 of the inflatable fill structure 4200. The radially self-expanding structures 4204a, 4204b, 4204c, and 4204d can serve a similar function as the ring-shaped inflatable fill elements 3906a, 3906b, 3906c, and 3906d in the embodiment of the aneurysm fill system illustrated in FIG. 39. When released from a delivery catheter, the radially self-expanding structures 4204a, 4204b, 4204c, and 4204d can expand and open the central passage 4206 of the inflatable fill structure 4200. In various embodiments, the radially self-expanding structures 4204a, 4204b, 4204c, and 4204d are made from a shape memory alloy such as Nitinol (nickel and titanium) or spring steel. Radial expansion forces of the radially self-expanding structures 4204a, 4204b, 4204c, and 4204d can be sufficiently high to unfurl the inflatable fill structure 4200 and open the central passage 4206. As shown in FIG. 42B, the expansion force can also be sufficiently low such that pressure forces (illustrated with arrows) created by a fill medium in the inflatable fill structure 4200 can collapse the radially self-expanding structures 4204a, 4204b, 4204c, and 4204d inwards. In some embodiments, the inflatable fill structure 4200 can collapse inwards onto a stent graft that can be placed inside the central passage 4206 of the inflatable fill structure 4200. The unfurling of the inflatable fill structure 4200 may be facilitated by injecting fill medium (e.g., saline) into the inflatable fill structure 4200 to overcome stickiness and friction in the inflatable fill structure 4200 when the inflatable fill structure 4200 is crimped or compressed. In some embodiments, the fill medium injected to help unfurl the inflatable fill structure 4200 can be removed and replaced with a hardenable and/or polymer fill medium.

In some embodiments, in order to fill the aneurysm fill system with fill medium, the fill tube can stay connected to the inflatable fill structure throughout the implantation of the stent graft system. In some situations it may be advantageous to first complete the entire implantation of the aneurysm fill system before deploying the stent graft system.

Figure 43C:
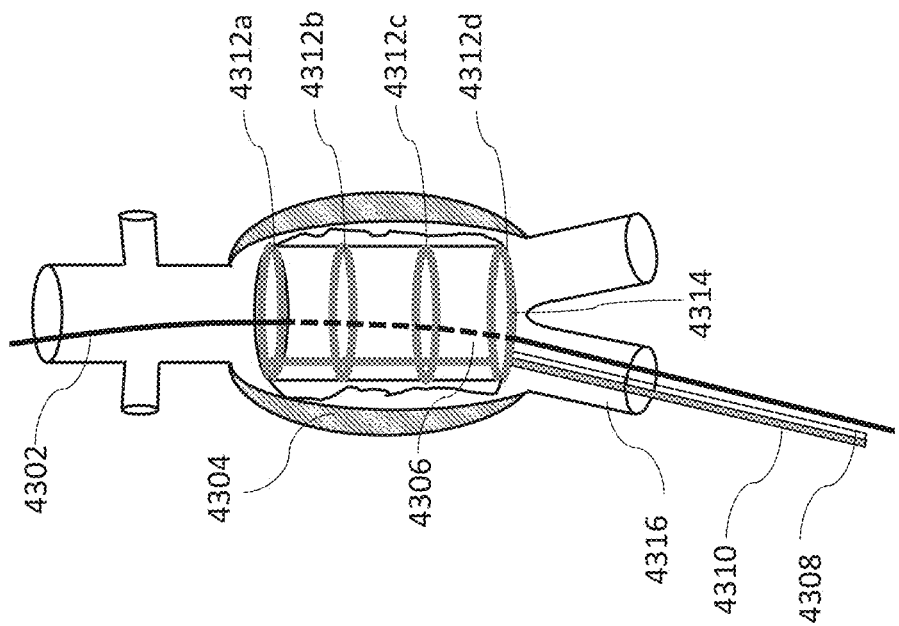
FIGS. 43A, 43B, 43C, 43D, 43E, and 43F are illustrations showing some steps during implantation of an aneurysm fill system with an inflatable permanent scaffold, in accordance with an illustrative embodiment.
Figure 43B:
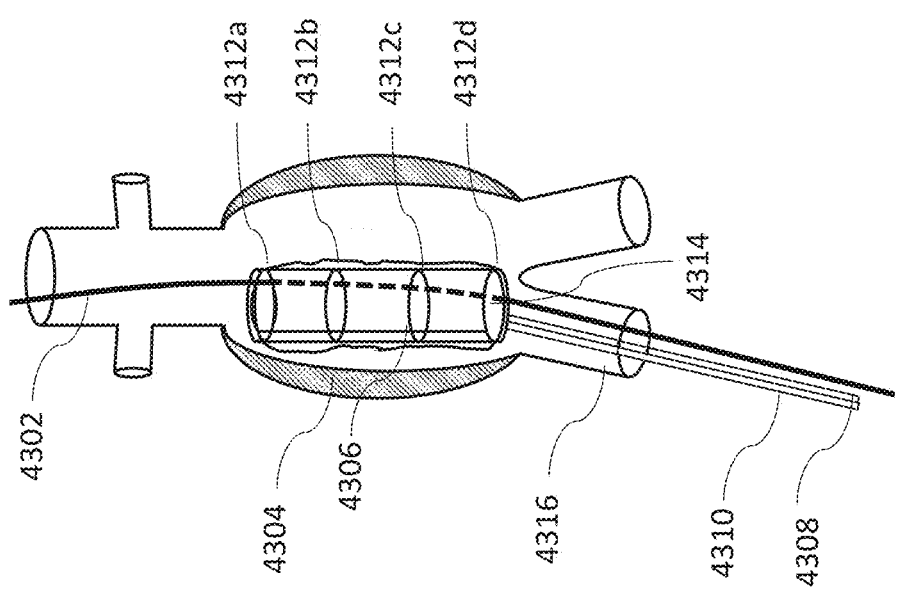
Figure 43A:
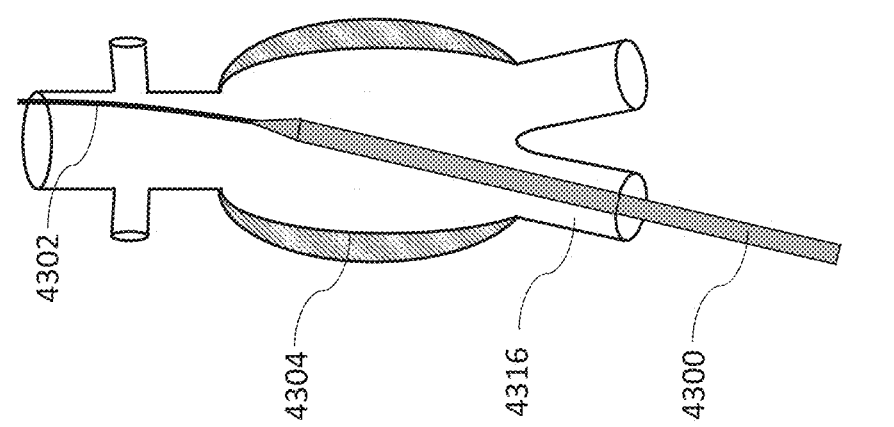
Figure 43F:
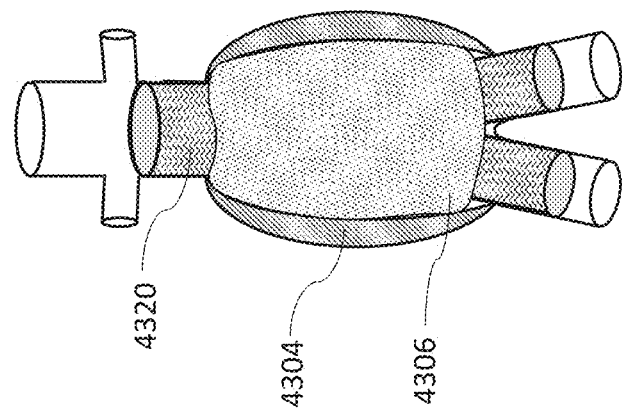

FIGS. 43A, 43B, 43C, 43D, 43E, and 43F are illustrations showing some steps during implantation of an aneurysm fill system with an inflatable permanent scaffold, in accordance with an illustrative embodiment. FIG. 43G is a flow diagram illustrating a method of implanting an aneurysm fill system with an inflatable permanent scaffold, in accordance with an illustrative embodiment. With reference to FIGS. 43A and 43G, in step 4330, a guidewire 4302 is inserted into an aneurysm 4304. In step 4335, a first delivery catheter 4300 is inserted into the aneurysm via the guidewire 4302. FIG. 43A shows the first delivery catheter 4300 that houses an aneurysm fill system being advanced over the guidewire 4302 through an ipsilateral iliac artery 4316 into the aneurysm 4304, in accordance with an illustrative embodiment. With reference to FIGS. 43A, 43B and 43G, in step 4340, an inflatable fill structure 4306 is released from the delivery catheter 4300 in the aneurysm 4304, and the delivery catheter 4300 can be retracted. In various embodiments, a first fill tube 4308 is connected to the inflatable fill structure 4306 and a second fill tube 4310 is connected to inflatable fill elements 4312a, 4312b, 4312c, and 4312d that can provide an inflatable permanent scaffold for the inflatable fill structure 4306 to allow for expanding a central passage 4314 of the inflatable fill structure 4306. The guidewire 4302 extends from the ipsilateral iliac artery 4316 through the central passage 4314.

With reference to FIGS. 43C and 43G, in step 4345, fill medium is injected into the inflatable fill elements 4312*a*, 4312*b*, 4312*c*, and 4312*d* through the second fill tube 4310. In an illustrative embodiment, the fill medium can be hardenable to form a permanent scaffold for the inflatable fill structure 4306. In various embodiments, the inflated or filled inflatable fill elements 4312*a*, 4312*b*, 4312*c*, and 4312*d* open the central passage 4314 in the inflatable fill structure 4306 and form a rigid support scaffold for the inflatable fill structure 4306. The guidewire 4302 extends from the ipsilateral iliac artery 4316 through the central passage 4314. The first fill tube 4308 allows for filling the inflatable fill structure 4306 in the aneurysm 4304. With reference to FIGS. 43D and 43G, in step 4350, the inflatable fill structure 4306 is filled with fill medium. The rigid support scaffold can prevent the inflatable fill structure 4306 from collapsing the central passage 4314. The guidewire 4302 remains extending through the central passage 4314 while the inflatable fill structure 4306 is filled. The inflatable fill structure 4306 can be filled to conform to a wall of the aneurysm 4304. The first and second fill tubes 4308 and 4310 (refer to FIG. 43C) can be removed.

Figure 43E:
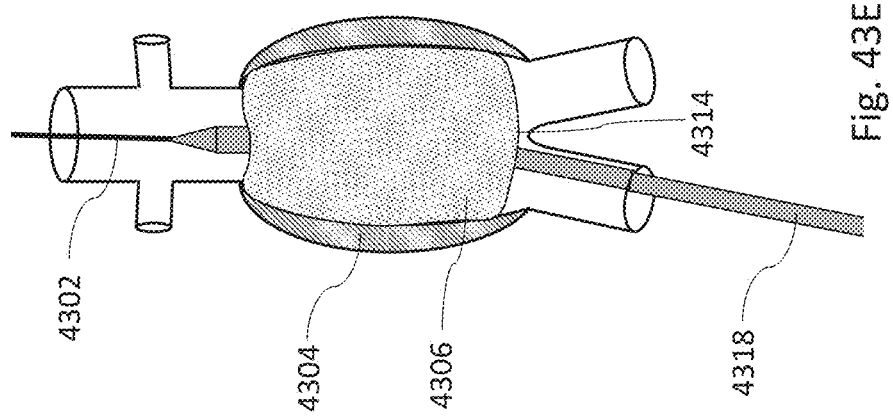
Figure 43D:
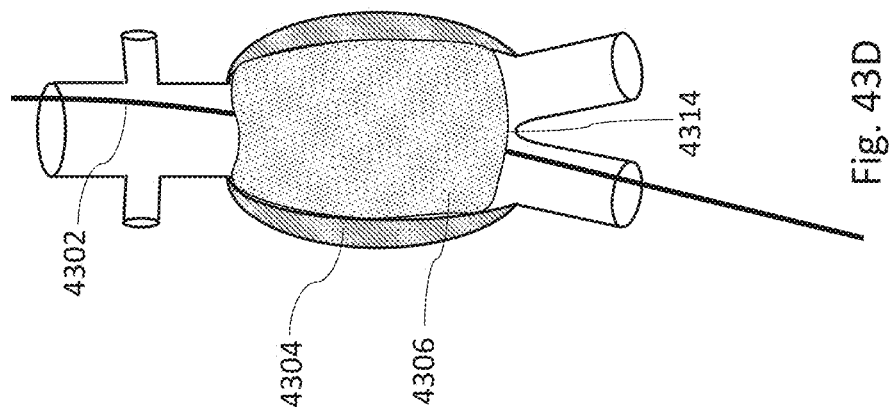
Figure 43G:
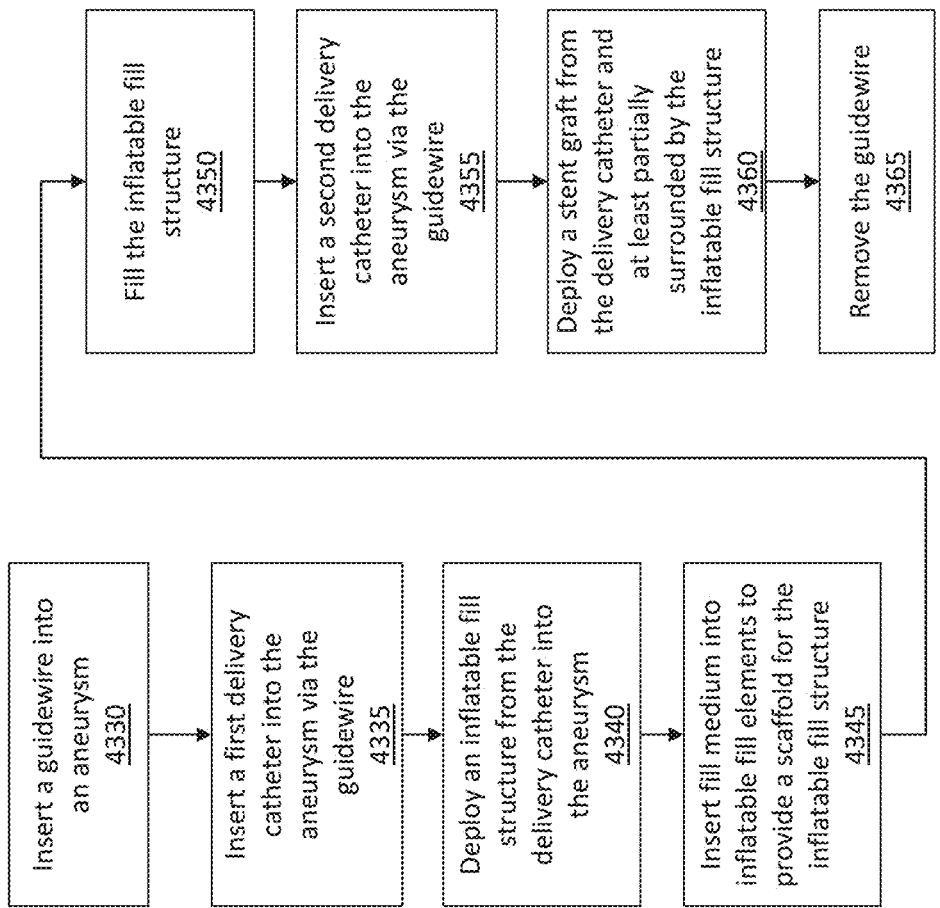
FIG. 43G is a flow diagram illustrating a method of implanting an aneurysm fill system with an inflatable permanent scaffold, in accordance with an illustrative embodiment.

With reference to FIGS. 43E and 43G, in step 4355, a second delivery catheter 4318 housing a stent graft system that includes a stent graft is advanced over the guidewire 4302 and through the central passage 4314 of the inflatable fill structure 4306 in the aneurysm 4304. With reference to FIGS. 43E, 43F, and 43G, in step 4360, the stent graft system 4320 is deployed from the delivery catheter 4318 at least partially surrounded by the inflatable fill structure 4306. In step 4365, the guidewire 4302 is removed. FIG. 43F illustrates the completed aneurysm repair with the stent graft system 4320 deployed across the aneurysm 4304.

In some embodiments, an inner wall of the inflatable fill structure 4306 might not conform to an outer surface of the stent graft system 4320, but the inflatable fill structure 4306 can conform to an inner wall of the aneurysm 4304, thereby eliminating potential Type II endoleaks from branch vessels and providing support against negative remodeling of the aneurysm 4304. An exemplary embodiment of the aneurysm fill system shown in FIG. 42A may also be used complete the entire deployment of the aneurysm fill system prior to stent graft implantation. In various embodiments, the radial strength of the radially self-expanding structures 4204*a*, 4204*b*, 4204*c*, and 4204*d* shown in FIG. 42A can be increased to withstand a collapse of the central passage 4206 by fill pressure in the inflatable fill structure 4200. Such an embodiment could use, for example, a self-expanding stent with high expansion forces for the radially self-expanding structures 4204*a*, 4204*b*, 4204*c*, and 4204*d* or balloon expanded stents.

Figure 44C:
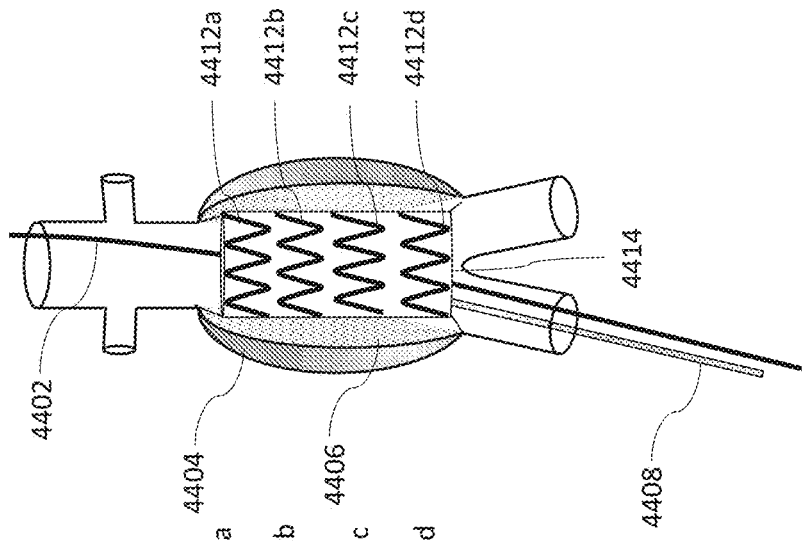
FIGS. 44A, 44B, 44C, 44D, 44E, and 44F are illustrations showing some steps during implantation of an aneurysm fill system with a stent, in accordance with an illustrative embodiment.
Figure 44B:
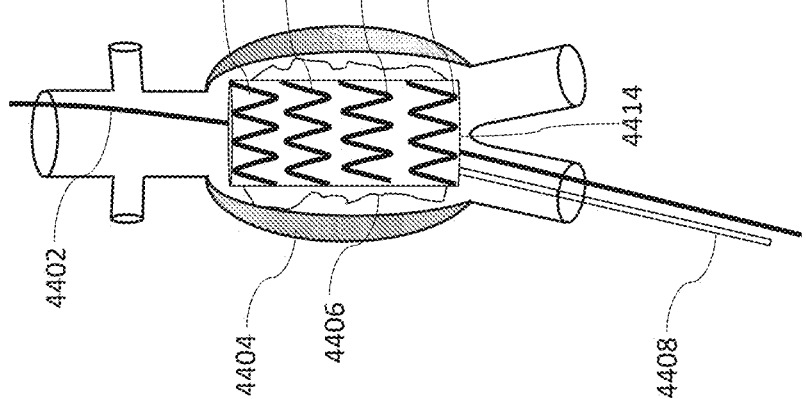
Figure 44A:
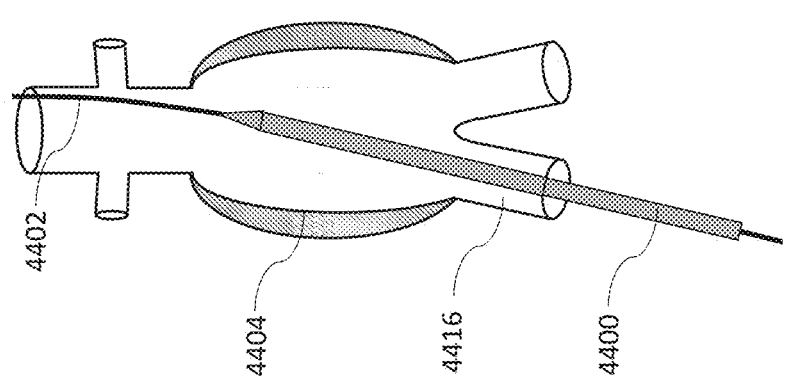
Figure 44F:
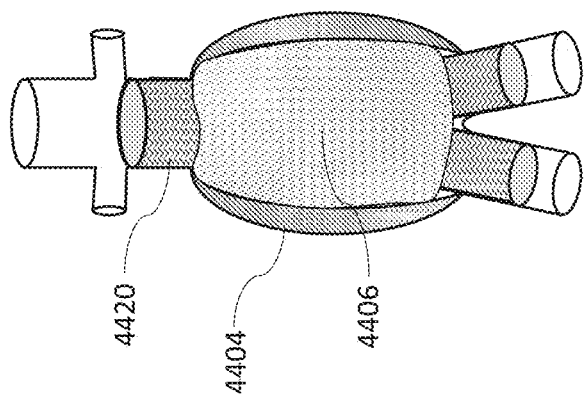

FIGS. 44A, 44B, 44C, 44D, 44E, and 44F are illustrations showing some steps during implantation of an aneurysm fill system and a stent graft, in accordance with an illustrative embodiment. FIG. 44G is a flow diagram illustrating a method of implanting an aneurysm fill system and a stent graft, in accordance with an illustrative embodiment. With reference to FIGS. 44A and 44G, in step 4430, a guidewire 4402 is inserted into an aneurysm 4404. In step 4435, a first delivery catheter 4400 is inserted into the aneurysm via the guidewire 4402. FIG. 44A shows the first delivery catheter 4400 that houses an aneurysm fill system being advanced over the guidewire 4402 through an ipsilateral iliac artery 4416 into the aneurysm 4404.

With reference to FIGS. 44A, 44B, and 44G, in step 4440, an inflatable fill structure 4406 is released from the delivery catheter 4400 into the aneurysm 4404. Self-expanding structures 4412*a*, 4412*b*, 4412*c*, and 4412*d* of the inflatable fill structure 4406 can unfurl the inflatable fill structure 4406 and radially expand a central passage 4414 of the inflatable fill structure 4406. In some embodiments, the self-expanding structures 4412*a*, 4412*b*, 4412*c*, and 4412*d* include one or more stents. In various embodiments, the guidewire 4402 extends through the central passage 4414 of the inflatable fill structure 4406. In various embodiments, a fill tube 4408 allows for filling the inflatable fill structure 4406. With reference to FIGS. 44C, 44D, and 44G, in step 4445, fill medium is injected through the fill tube 4408 into the inflatable fill structure 4406. The self-expanding structures 4412*a*, 4412*b*, 4412*c*, and 4412*d* are configured to prevent the inflatable fill structure 4406 from collapsing the central passage 4414 when the inflatable fill structure 4406 is filled. The inflatable fill structure 4406 can be filled to conform to a wall of the aneurysm 4404. The fill tube 4408 can be removed. The guidewire 4402 can remain in place for further guiding of a delivery catheter. FIG. 44D shows the fully deployed aneurysm fill system in the aneurysm sac.

Figure 44E:
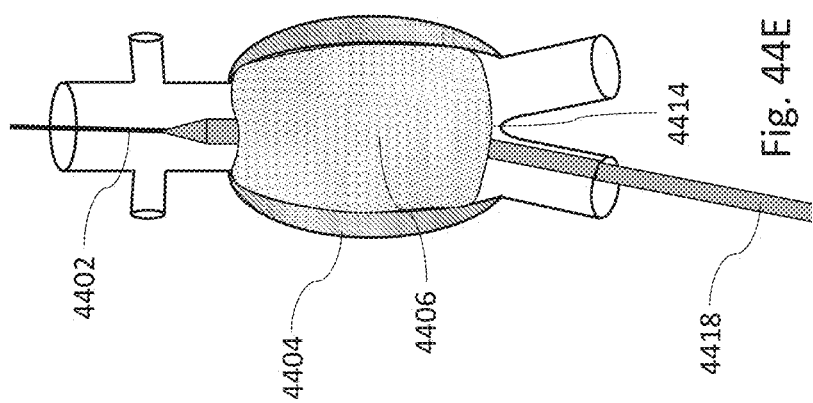
Figure 44D:
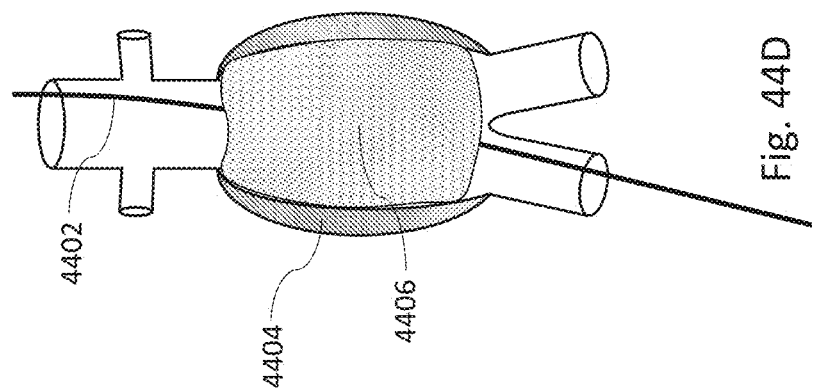
Figure 44G:
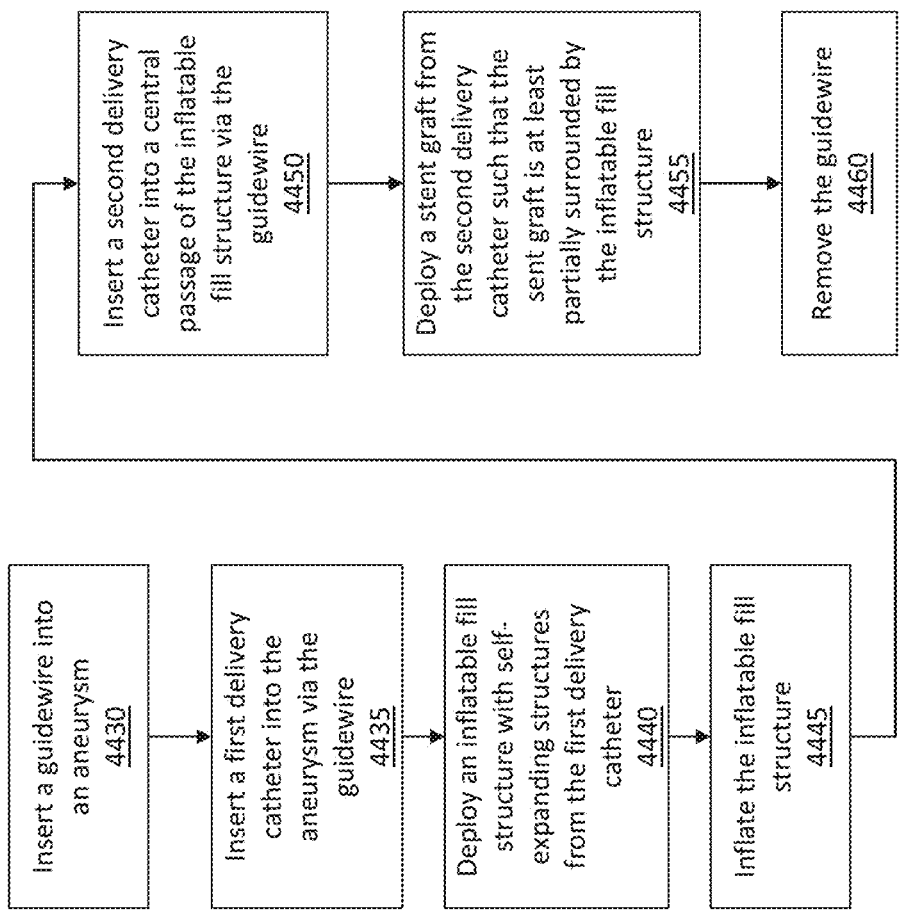
FIG. 44G is a flow diagram illustrating a method of implanting an aneurysm fill system with a stent, in accordance with an illustrative embodiment.

With reference to FIGS. 44E and 44G, in step 4450, a second delivery catheter 4418 housing a stent graft system including a stent graft is advanced over the guidewire 4402. The second delivery catheter 4418 can pass through the central passage 4414 of the inflatable fill structure 4406 in the aneurysm 4404. With reference to FIGS. 44E, 44F, and 44G, in step 4455, the stent graft system 4420 is deployed from the second delivery catheter 4418 and is at least partially surrounded by the inflatable fill structure 4406. In step 4460, the guidewire 4402 is removed. FIG. 44F shows the completed aneurysm repair with the stent graft system 4420 excluding the aneurysm 4404. The inflatable fill structure 4406 can fill the aneurysm space.

Figure 45C:
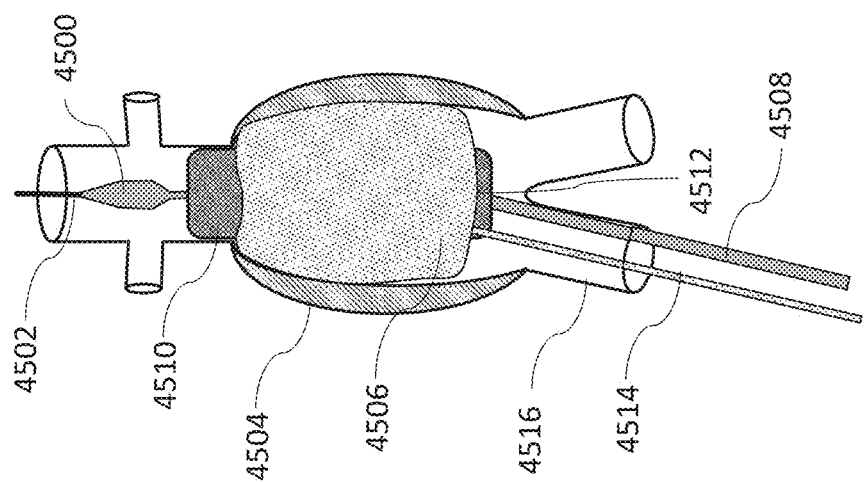
Figure 45B:
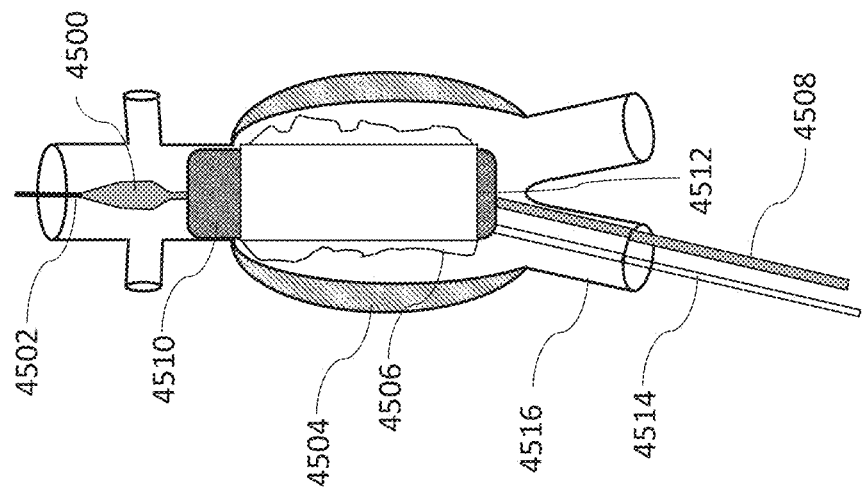

In various embodiments of an aneurysm fill system, a temporary support of a central lumen or central passage of an inflatable fill structure is provided by a balloon. In some embodiments, the inflatable fill structure is mounted onto a balloon and loaded into a delivery system, such as a delivery catheter. FIGS. 45A, 45B, 45C, 45D, 45E, and 45F are illustrations showing some steps during implantation of an aneurysm fill system with an inflatable balloon, in accordance with an illustrative embodiment. FIG. 45G is a flow diagram illustrating a method of implanting an aneurysm fill system with an inflatable balloon, in accordance with an illustrative embodiment.

Figure 45A:
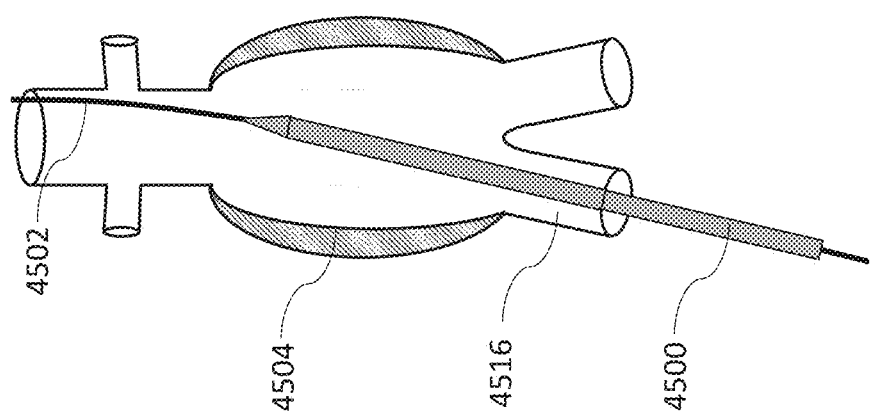
Figure 45G:
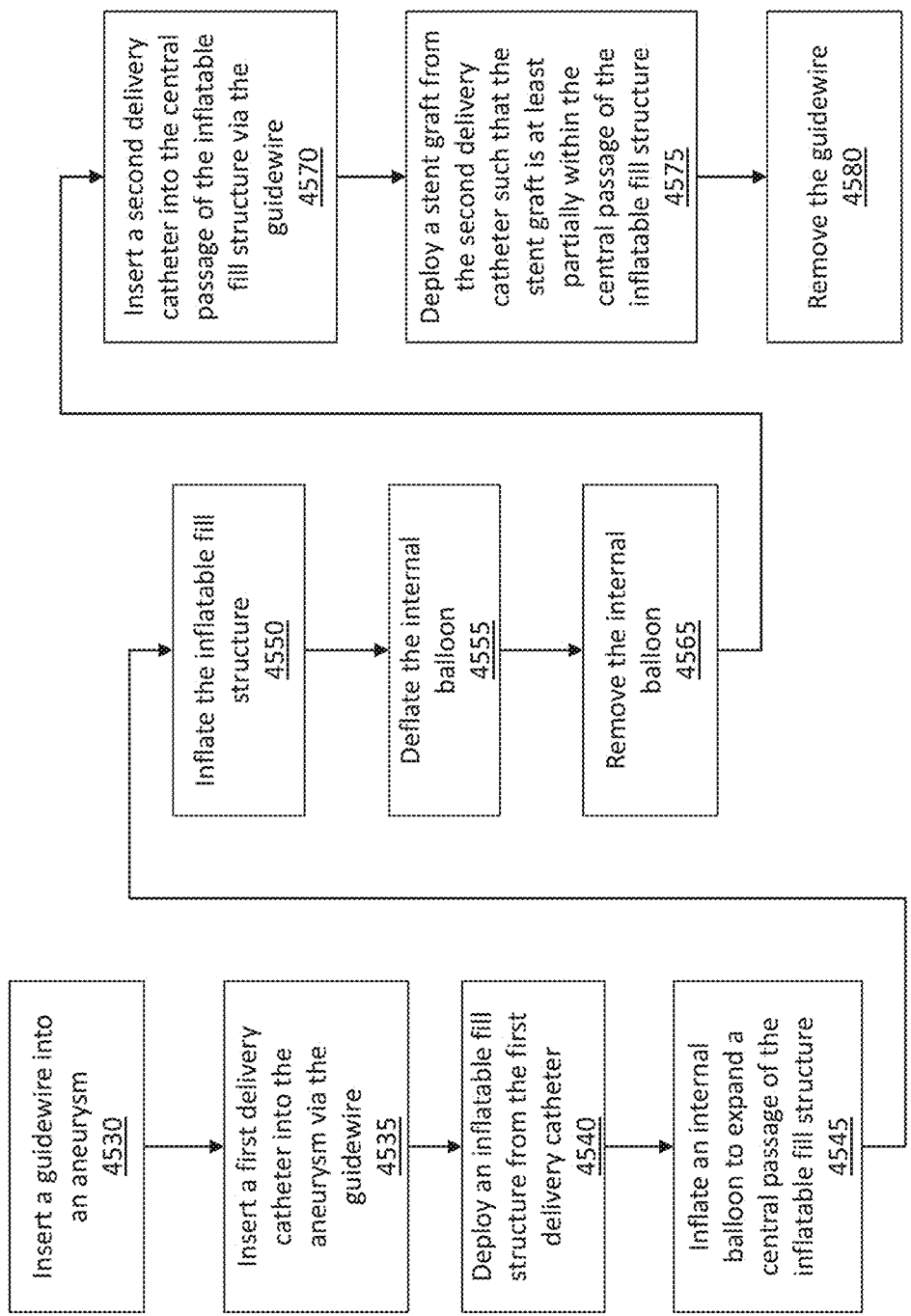
FIG. 45G is a flow diagram illustrating a method of implanting an aneurysm fill system with an inflatable balloon, in accordance with an illustrative embodiment.

With reference to FIGS. 45A and 45G, in step 4530, a guidewire 4502 is inserted into an aneurysm 4504. In step 4535, a first delivery catheter 4500 is inserted into the aneurysm 4504 via the guidewire 4502. FIG. 45A shows the first delivery catheter 4500 that houses an aneurysm fill system being advanced over the guidewire 4502 through an ipsilateral iliac artery 4516 into the aneurysm 4504, in accordance with an exemplary embodiment. With reference to FIGS. 45A, 45B, and 45G, in step 4540, an inflatable fill structure 4506 is released from the delivery catheter 4500. In step 4545, an internal balloon 4510 is inflated. In various embodiments, fluid is injected through a balloon fill lumen 4508 to inflate the internal balloon 4510. The internal balloon 4510 can unfurl the inflatable fill structure 4506 and radially expand a central passage 4512 of the inflatable fill structure 4506. A fill tube 4514 that extends though the ipsilateral iliac artery 4516 allows for filling a fill medium into the inflatable fill structure 4506 in the aneurysm 4504. The guidewire 4502 can remain while the internal balloon 4510 is inflated.

With reference to FIGS. 45C and 45G, in step 4550, fill medium is injected through the fill tube 4514 into the inflatable fill structure 4506. In various embodiments, the fill medium injected into the inflatable fill structure 4506 is hardenable. In various embodiments, the inflatable fill structure 4506 is configured to conform to a wall of the aneurysm 4504 and to an outer surface of the internal balloon 4510. The internal balloon 4510 can remain inflated in the central passage 4512 of the inflatable fill structure 4506 while the inflatable fill structure 4506 is being filled. The internal balloon 4510 can prevent the inflatable fill structure 4506 from collapsing inward while the inflatable fill structure 4506 is being filled. In various embodiments, the fill medium in the inflatable fill structure 4506 can harden, and the fill tube 4514 can be removed. In various embodiments, the delivery catheter 4500 on the guidewire 4502 remains extending through the internal balloon 4510 and can be used for removing the internal balloon 4510 and the balloon fill lumen 4508 through the ipsilateral iliac artery 4516 after the internal balloon 4510 has been deflated.

With reference to FIGS. 45D, and 45G, in step 4555, the internal balloon 4510 is deflated, and in step 4565, the internal balloon 4510 is removed. FIG. 45D shows the fully deployed inflatable fill structure 4506 in the aneurysm 4504 with the deflated internal balloon 4510 still in place. In various embodiments, the delivery catheter 4500 on the guidewire 4502 is used to remove the deflated internal balloon 4510. With reference to FIGS. 45E and 45G, in step 4570, a second delivery catheter 4516 housing a stent graft system including a stent graft is advanced over the guidewire 4502 through the central passage 4512 in the inflatable fill structure 4506 in the aneurysm 4504. The second delivery catheter 4516 can span across the aneurysm 4504, as shown in FIG. 45E. With reference to FIGS. 45E, 45F, and 45G, in step 4575, the stent graft system 4518 is deployed from the second delivery catheter 4516 and is at least partially surrounded by the inflatable fill structure 4506. In step 4580, the guidewire 4502 is removed. FIG. 45F shows the completed aneurysm repair with the stent graft system 4518 excluding the aneurysm 4504 and the inflatable fill structure 4506 filling the aneurysm space.

In some of the various embodiments of aneurysm repair systems containing an inflatable fill structure described herein, aneurysm exclusion is obtained by a stent graft. The filled inflatable fill structure augments the repair by the stent graft by reducing the risk of Type II endoleaks and potentially stabilizing the aneurysm against negative remodeling. Various fill media may be considered for filling the inflatable fill structure. To be able to pass the fill medium through the fill tube, fill media consisting of a liquid or a liquid with suspended solid particles may be preferred. Once delivered into the inflatable fill structure, the fill medium may remain in its original consistency, may increase in viscosity, or may harden. In embodiments where the fill medium remains liquid, a hemostasis valve at the orifice into the inflatable fill structure may be preferred to prevent fill medium from escaping after removal of the fill tube. Slow, long-term escape of liquid fill medium may be acceptable, if the inflatable fill structure covers the ostia of the branch vessels in the aneurysm long enough to cause complete thrombosis of the branch vessels. In embodiments where the fill medium hardens, a permanent seal of the inflatable fill structure might not be required. Additionally, in various embodiments, a hemostasis valve may not be required to retain the fill medium in the inflatable fill structure. In some embodiments, the inflatable fill structure may be made from biodegradable material to allow for tissue ingrowth into the hardened fill medium.

In embodiments where a fluid fill medium is to remain liquid, a biocompatible liquid such as saline may be chosen. Biocompatible high-viscosity fluids such as polyethyleneglycol (PEG) solutions or silicone may be preferred. If the consistency of the fill medium is to change to a viscoelastic material, smart hydrogels that undergo phase transition may be preferred. Phase transitions may be triggered by a body temperature, a change in pH, etc. In some embodiments, a patient's own blood may be considered as a fill medium. In some such embodiments, stagnant blood in an inflatable fill structure can coagulate. The coagulation process may be accelerated by adding thrombin or any other coagulation agent to the blood. In embodiments where a hardened fill medium is preferred, various polymers may be considered such as PEG-acrylate, polyurethane formulations, or the like. The polymeric precursors may cross-link with each other by a radical reaction or may be connected by cross-linking agents. Polymeric precursors may react with water to form a hardened fill medium. Catalysts may be added to accelerate a cross-linking reaction.

Figure 46B:
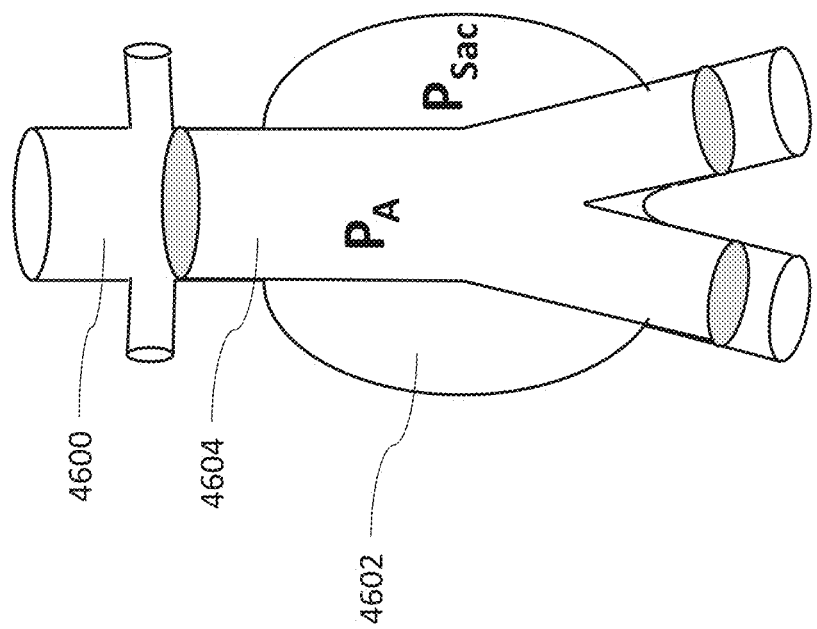
FIGS. 46A and 46B are example illustrations of the location of pressures $P_A$ and $P_{SAC}$ in an abdominal aortic aneurysm prior to and after deployment of an aneurysm exclusion device, respectively.
Figure 46A:
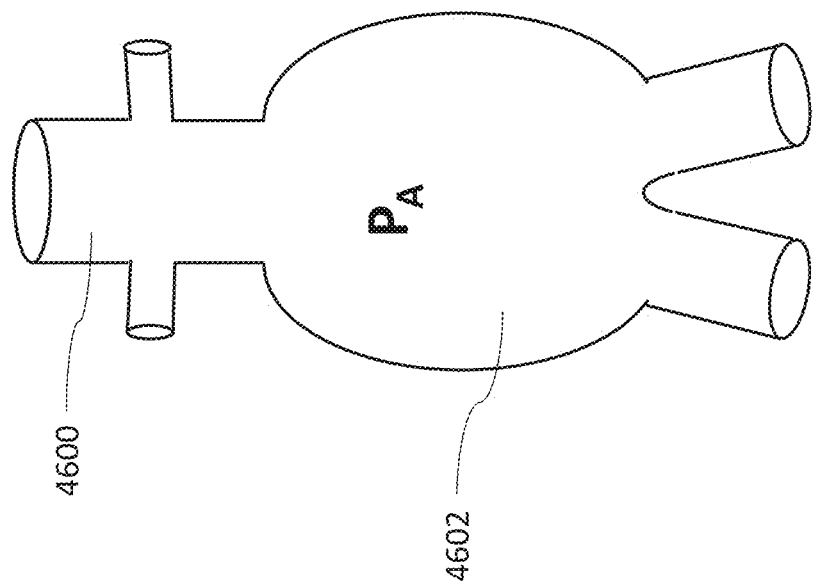

In various embodiments, pressure force relationships within an excluded aneurysm may be used to control the delivery of a fill medium. FIGS. 46A and 46B are illustrations of the location of pressures $P_A$ (representing a pressure in an aorta) and $P_{SAC}$ (representing a pressure in an aneurysm sac) in an abdominal aortic aneurysm prior to and after deployment of an aneurysm exclusion device, respectively. FIG. 46A shows an infrarenal aneurysm 4602 before an endovascular repair where the pressure in the aneurysm 4602 is equal to the pressure ($P_A$) in an aorta 4600. FIG. 46B shows the infrarenal aneurysm 4602 excluded by a stent graft system 4604. In the absence of a leak from the aorta 4600 into the aneurysm 4602, the aneurysm sac pressure, $P_{SAC}$, is less than the aortic pressure, $P_A$. As the aneurysm sac thrombosis over time, the aneurysm sac pressure $P_{SAC}$ can drop to zero.

Figure 47:
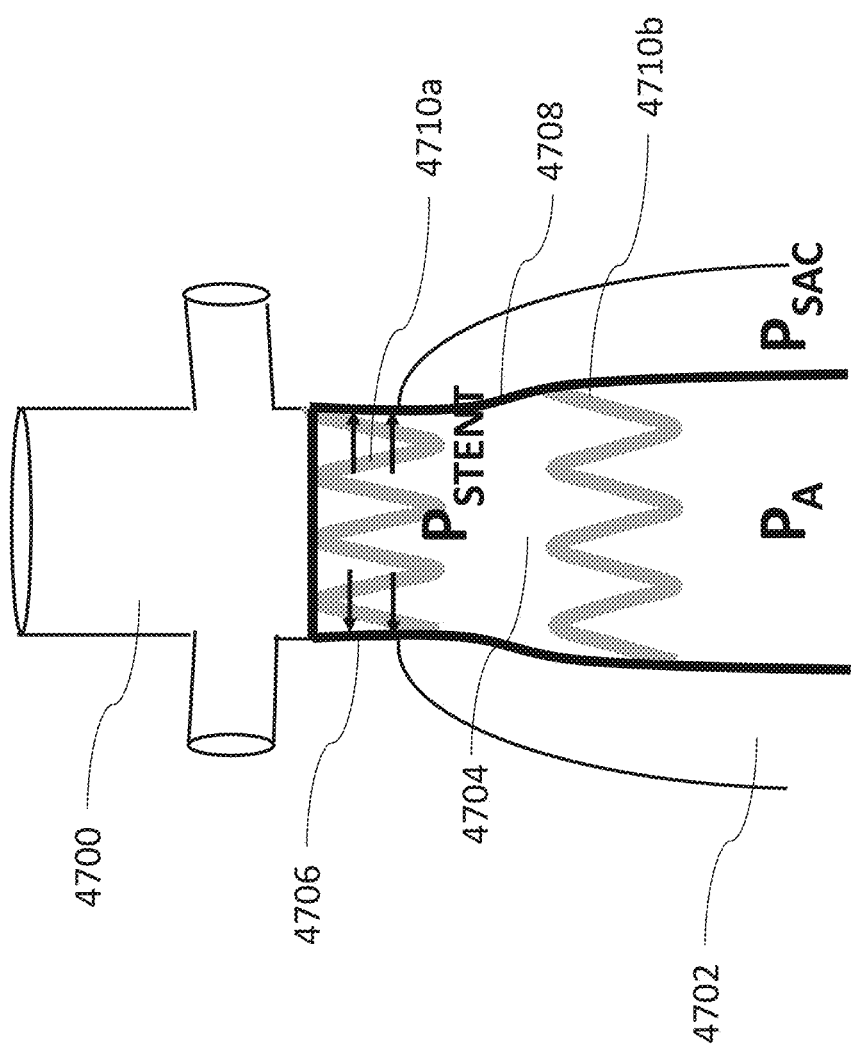
FIG. 47 is an example illustration of the location of pressures $P_{STENT}$, $P_A$, and $P_{SAC}$ in an area of a proximal neck for an aneurysm with a stent graft deployed in the aneurysm.

FIG. 47 is an illustration of a location of pressures $P_{STENT}$ (representing an expansion pressure of a stent element), $P_A$, and $P_{SAC}$ in an area of a proximal neck of an abdominal aortic aneurysm with a stent graft deployed in an infrarenal aneurysm. FIG. 47 shows an example of a stent graft 4704 placed in an aorta 4700 across an infrarenal aneurysm 4702. The stent graft 4704 has a tubular graft 4708 and supporting self-expanding stent elements 4710a and 4710b. A diameter of the stent graft 4704 can be oversized as compared to a diameter of a proximal neck 4706. For example, the diameter of the stent graft 4704 may be 10%-40% larger than the diameter of the proximal neck 4706. As a result, the most proximal self-expanding stent element 4710a can be compressed to the diameter of the proximal neck 4706, which exerts the expansion pressure $P_{STENT}$ onto the aortic wall at the proximal neck 4706. The pressure $P_{STENT}$ and the aortic pressure $P_A$ push the tubular graft 4708 against the proximal neck 4706, thereby creating a proximal seal. The self-expanding stent element 4710b outside of the proximal neck 4706 can be fully expanded to its nominal diameter and might not exert an outward force.

Figure 48:
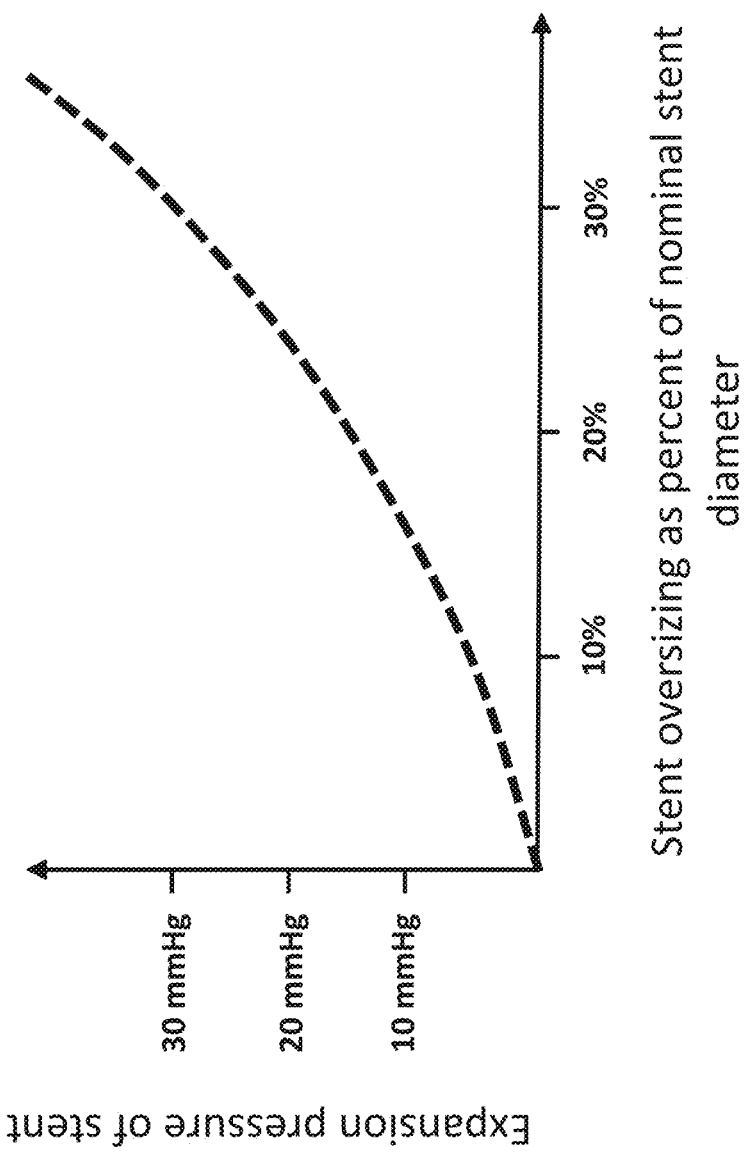
FIG. 48 is an example plot of stent oversizing nominal diameter percentage (%) versus expansion force converted to pressure in a circular or cylindrical lumen of a self-expanding stent.

FIG. 48 is an example of a plot of stent oversizing nominal diameter percentage (%) versus expansion force converted to pressure in a circular or cylindrical lumen of a self-expanding stent. FIG. 48 illustrates a relationship between stent diameter and an expansion pressure of the stent $P_{STENT}$. The expansion pressure $P_{STENT}$ of the stent increases with the degree of oversizing. In some instances, $P_{STENT}$ can be of the order of 5 mmHg-60 mmHg in a proximal neck.

Figure 49:
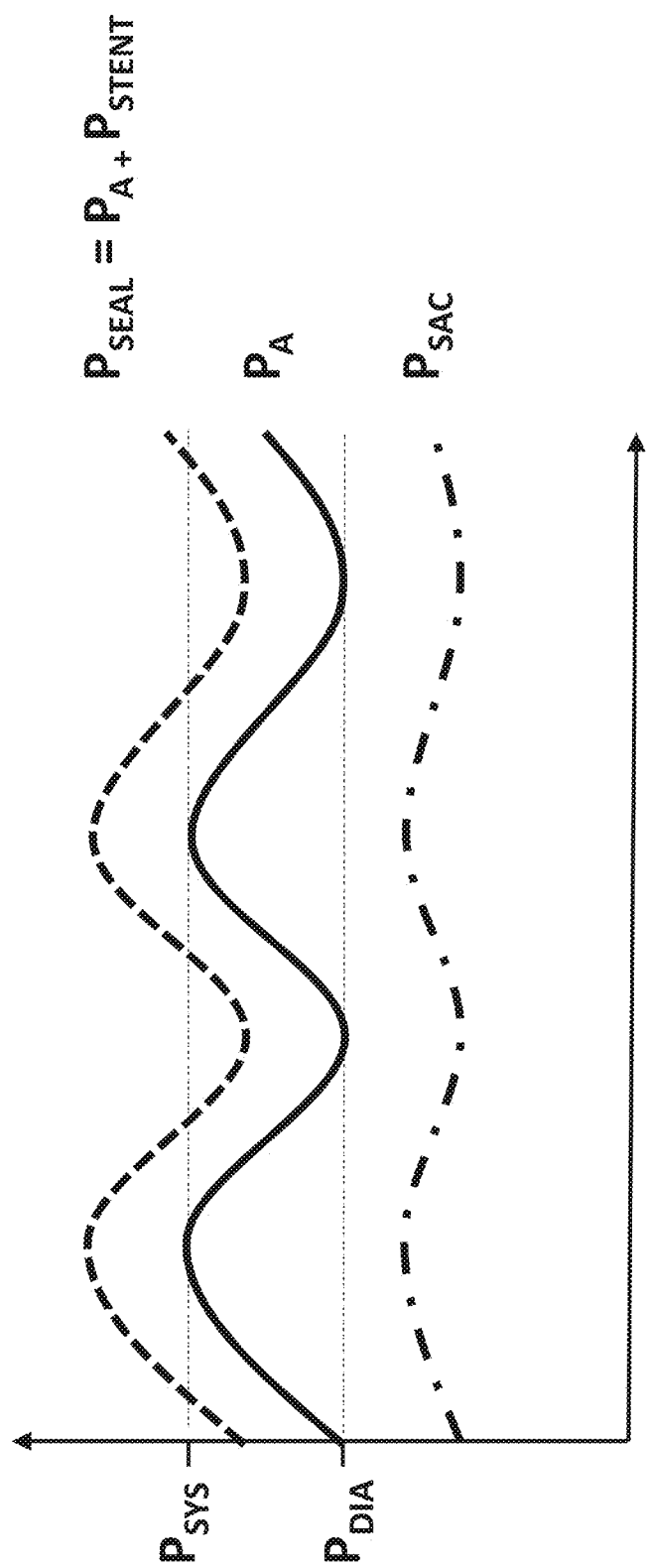
FIG. 49 is an example plot representing pressures $P_{SEAL}$, $P_A$, $P_{SYS}$ (systolic), $P_{DIA}$ (diastolic), and $P_{SAC}$ versus time.

FIG. 49 is a plot of pressures $P_A$, $P_{SYS}$ (representing systolic aortic pressure), $P_{DIA}$ (representing diastolic aortic pressure), $P_{SAC}$, and $P_{SEAL}$ (representing $P_A+P_{STENT}$) versus time prior to full deployment of an aneurysm exclusion device. The aortic pressure $P_A$ (solid line) oscillates between the diastolic aortic pressure $P_{DIA}$ and the systolic aortic pressure $P_{SYS}$. In some instances, a ratio $P_{SYS}/P_{DIA}$ is of the order of 120 mmHg/80 mmHg in healthy patients to 180 mmHg/120 mmHg in chronic hypertensive patients. In a patient undergoing an aneurysm repair procedure, the ratio may be as low as, for example, 80 mmHg/50 mmHg. In the plot of FIG. 49, the aneurysm sac pressure $P_{SAC}$ is less than the aortic pressure $P_A$ with a reduced pressure amplitude. The seal pressure acting on the stent graft in the proximal neck $P_{SEAL}$ is equal to a sum of the aortic pressure $P_A$ and the pressure of the stent $P_{STENT}$ exerted on the aortic wall. A net pressure exerted onto the stent graft in the aneurysm is the difference between the aortic pressure $P_A$ and the aneurysm sac pressure $P_{SAC}$. Because $P_A$ is larger than $P_{SAC}$ in this example, a net outward pressure acts on the stent graft. Thus, in accordance with the example, the unconstrained stent graft would be in its fully expanded configuration.

Figure 50:
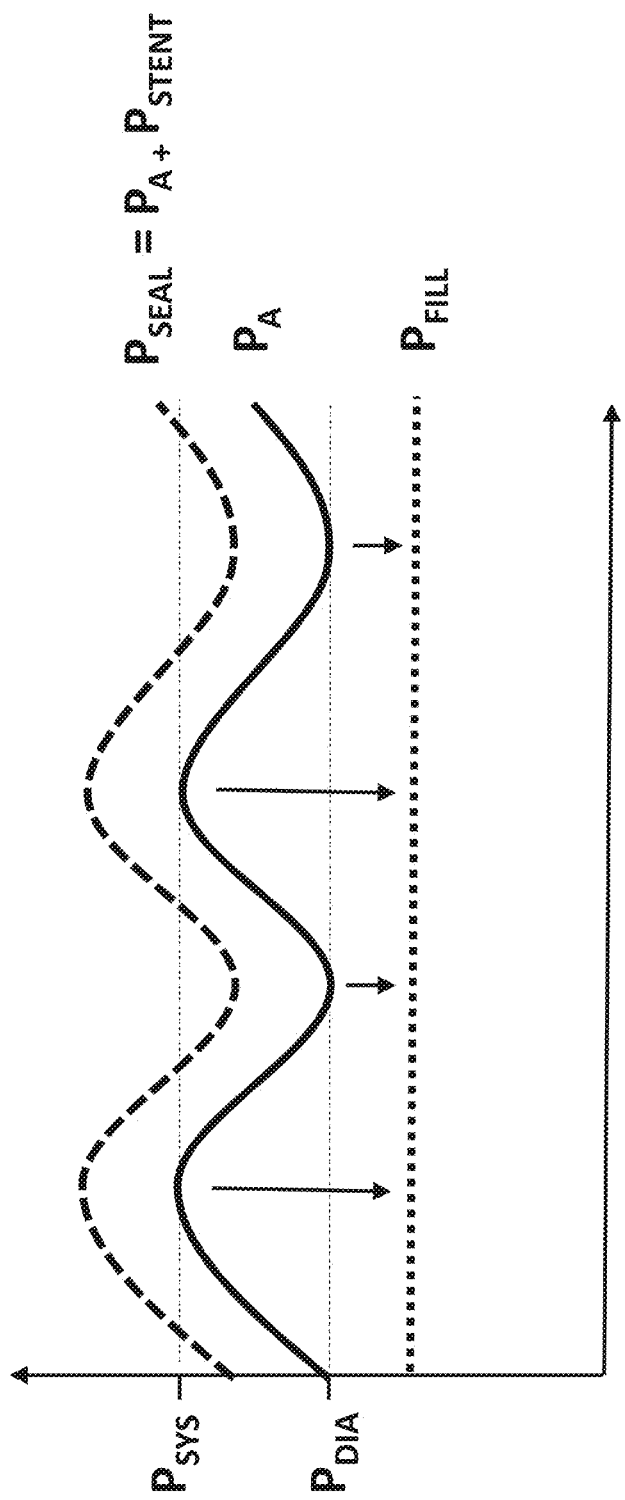
FIG. 50 is a plot representing the pressures $P_{SEAL}$, $P_A$, $P_{FILL}$, $P_{SYS}$ (systolic), and $P_{DIA}$ (diastolic) versus time prior to full deployment of an aneurysm exclusion device with a partially filled aneurysm fill system, in accordance with an illustrative embodiment.
Figure 51:
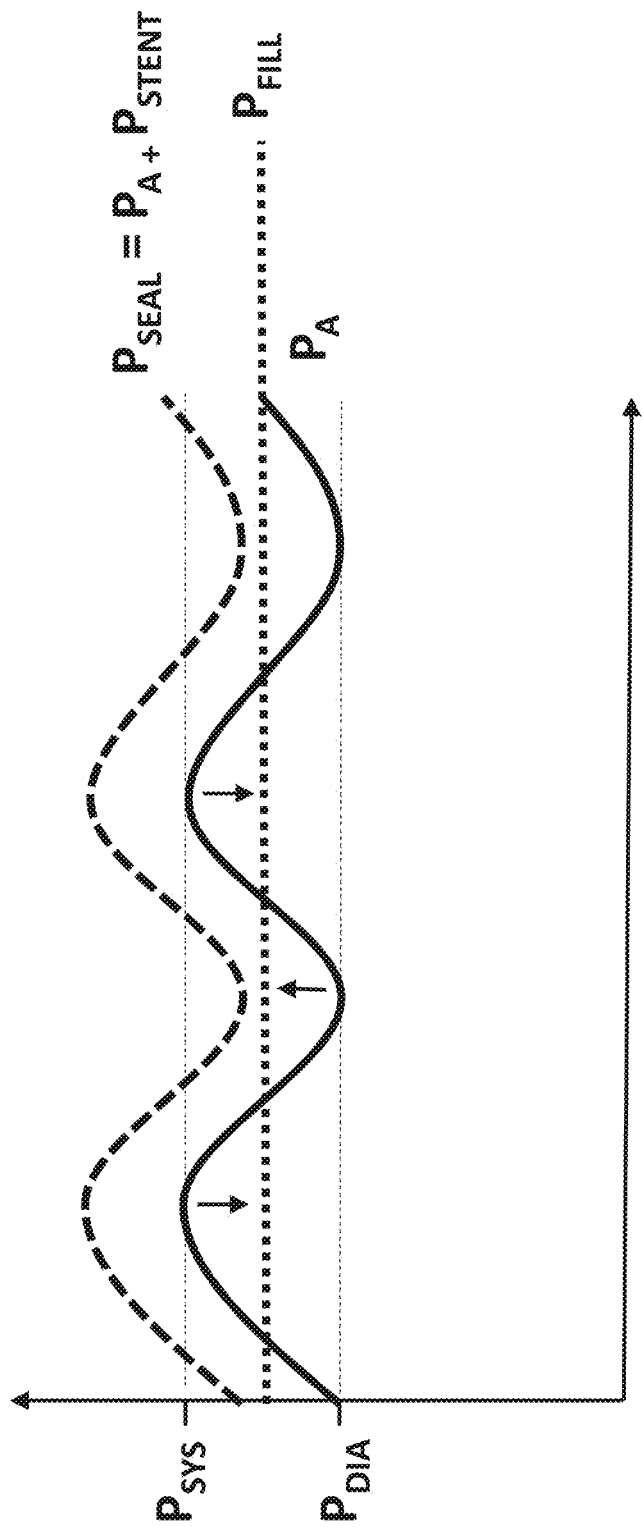
FIG. 51 is a plot representing the pressures $P_{SEAL}$, $P_A$, $P_{FILL}$, $P_{SYS}$ (systolic), and $P_{DIA}$ (diastolic) versus time at a condition of full deployment of an aneurysm exclusion device with an aneurysm fill system pressurized such that the fill pressure $P_{FILL}$ is greater than the $P_{DIA}$, in accordance with an illustrative embodiment.

FIGS. 50 and 51 illustrate dynamic pressures in an aneurysm repair that is augmented by placement of an inflatable fill structure in the aneurysm. FIG. 50 is an example plot of the pressures $P_{SEAL}$ (representing $P_A+P_{STENT}$), $P_{FILL}$, (representing a pressure in an inflatable fill structure), $P_{SYS}$ (systolic), and $P_{DIA}$ (diastolic) versus time prior to full deployment of an aneurysm exclusion device with a partially filled inflatable fill structure, in accordance with an illustrative embodiment. FIG. 51 is a plot representing the pressures $P_{SEAL}$ (representing $P_A+P_{STENT}$), $P_{FILL}$, $P_{SYS}$ (systolic), and $P_{DIA}$ (diastolic) versus time at the condition of full deployment of an aneurysm exclusion device with an aneurysm fill system pressurized such that the fill pressure of the inflatable fill structure, $P_{FILL}$, is greater than the $P_{DIA}$, in accordance with an illustrative embodiment.

During an initial phase of a filling process, shown in FIG. 50, the pressure in the inflatable fill structure $P_{FILL}$ is less than the aortic pressure $P_A$. The inflatable fill structure has not yet filled the entire aneurysm space and the walls of the inflatable fill structure are not yet pushing against the aneurysm. Since $P_A$ is larger than $P_{FILL}$, a net outward pressure (indicated by arrows) acts on the stent graft. The unconstrained stent graft remains in its fully expanded configuration.

FIG. 51 shows an example pressure relationships in an advanced stage of filling of the inflatable fill structure. The fill volume has reached a point at which the expansion of the inflatable fill structure is being constrained by the space in the aneurysm sac. The pressure $P_{FILL}$ exceeds the diastolic aortic pressure $P_{DIA}$, but has not yet reached the systolic aortic pressure $P_{SYS}$. During the systolic phase of the cardiac cycle, $P_A$ is greater than $P_{FILL}$ and a net outward pressure (indicated by downward arrows) acts onto the stent graft. During the diastolic phase of the cardiac cycle, $P_A$ is less than $P_{FILL}$ and a net inward pressure (indicated by an upward arrow) acts on the stent graft. The inward pressure tends to compress the stent graft radially inward.

Figure 52:
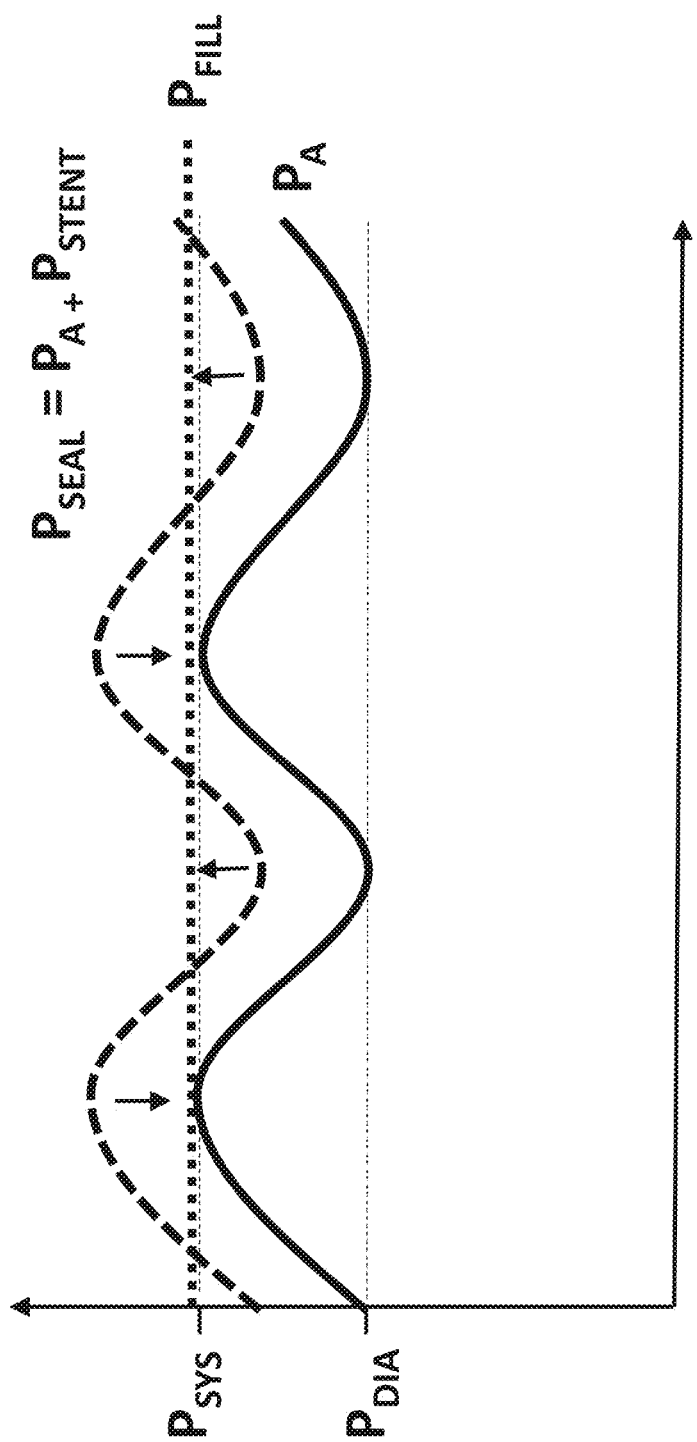
FIG. 52 is a plot representing the pressures $P_{SEAL}$, $P_A$, $P_{FILL}$, $P_{SYS}$ (systolic), and $P_{DIA}$ (diastolic) versus time at a condition of full deployment of an aneurysm exclusion device with an aneurysm fill system pressurized such that the fill pressure $P_{FILL}$ is greater than the $P_{SYS}$ and greater than the minimum pressure of the $P_{SEAL}$ pressure cycle, in accordance with an illustrative embodiment.

FIG. 52 is an example plot of the pressures $P_{SEAL}$ (representing $P_A+P_{STENT}$), $P_{FILL}$, $P_{SYS}$ (systolic), and $P_{DIA}$ (diastolic) versus time at the condition of full deployment of an aneurysm exclusion device with an aneurysm fill system pressurized such that the fill pressure in the inflatable fill structure, $P_{FILL}$, is greater than the $P_{SYS}$ and greater than a minimum pressure of the $P_{SEAL}$ pressure cycle, in accordance with an illustrative embodiment. FIG. 52 shows the pressure relationships in an extreme stage of filling of the inflatable fill structure. The fill pressure $P_{FILL}$ exceeds the systolic aortic pressure $P_{SYS}$ and is in excess of the proximal seal pressure $P_{SEAL}$ at some times. During the diastolic phase of the cardiac cycle, the seal pressure $P_{SEAL}$ is lower than the fill pressure $P_{FILL}$. The resulting net inward pressure may break the seal of the stent graft in the proximal neck. In various instances, such a situation should be avoided.

Figure 53B:
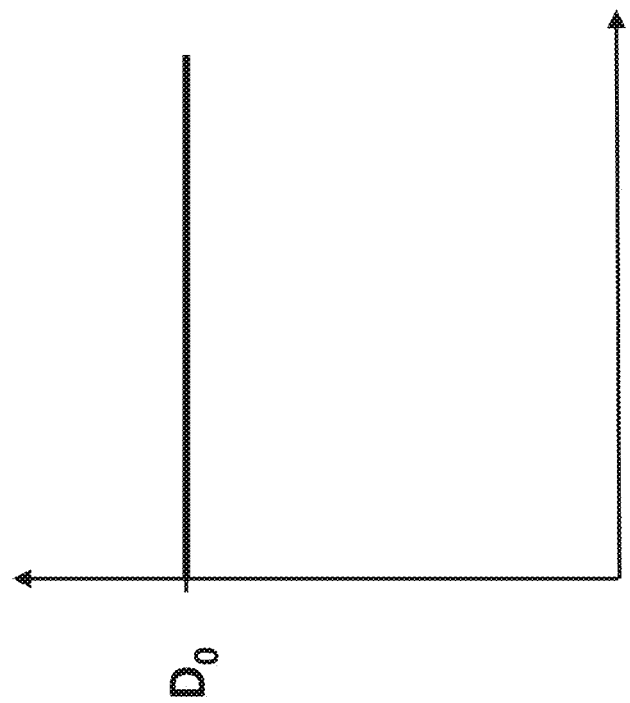
FIGS. 53A and 53B are plots of the pressures $P_A$ and $P_{FILL}$, and stent graft diameter versus time, respectively, prior to full deployment of an aneurysm exclusion device with a partially filled aneurysm fill system, in accordance with an illustrative embodiment.
Figure 53A:
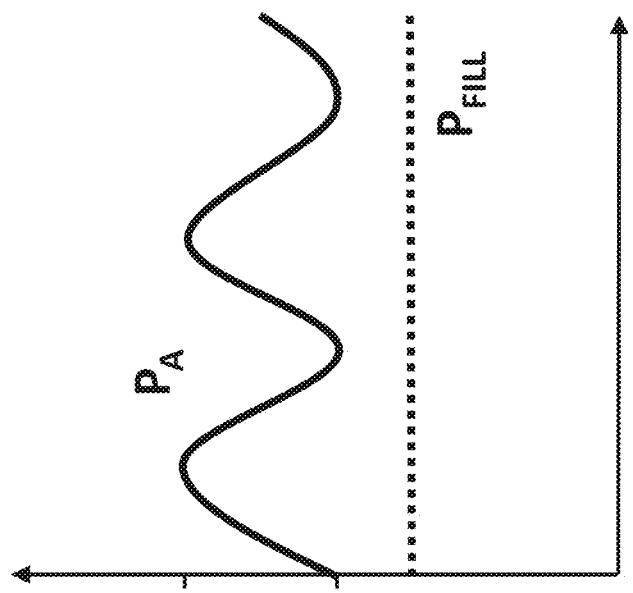

FIGS. 53A, 53B, 54A, 54B, 55A, and 55B further illustrate examples of a dynamic relationship between the fill pressure $P_{FILL}$ and an diameter of a lumen of the stent graft. FIGS. 53A and 53B are plots of $P_A$ and $P_{FILL}$, and stent graft diameter versus time, respectively, prior to full deployment of an aneurysm exclusion device with a partially filled aneurysm fill system in which an inflatable fill structure is partially filled, in accordance with an illustrative embodiment. FIG. 53A depicts the scenario from FIG. 50 in which the fill pressure $P_{FILL}$ is less than the aortic pressure $P_A$ throughout the cardiac cycle. The corresponding stent graft lumen diameter is plotted in FIG. 53B. Since the net pressure is always directed outward throughout the cardiac cycle, the stent graft remains at its fully expanded diameter $D_0$.

Figure 54B:
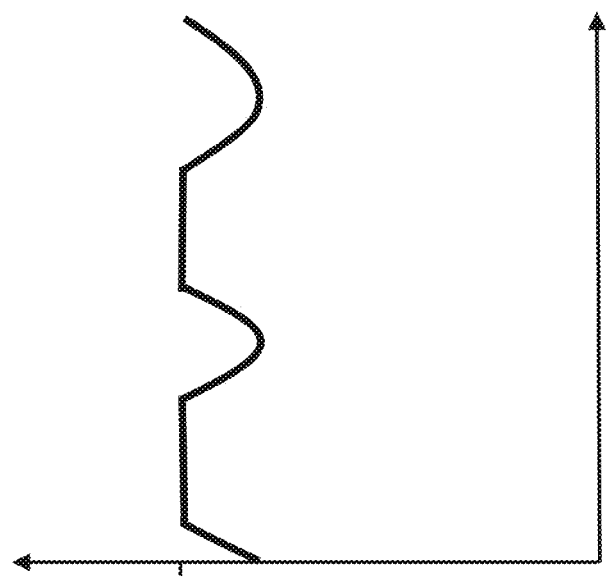
FIGS. 54A and 54B are plots of the pressures $P_A$ and $P_{FILL}$, and stent graft diameter versus time, respectively, when an aneurysm exclusion device comprising a filled aneurysm fill system is pressurized such that the fill pressure $P_{FILL}$ is greater than the $P_{DIA}$, in accordance with an illustrative embodiment.
Figure 54A:
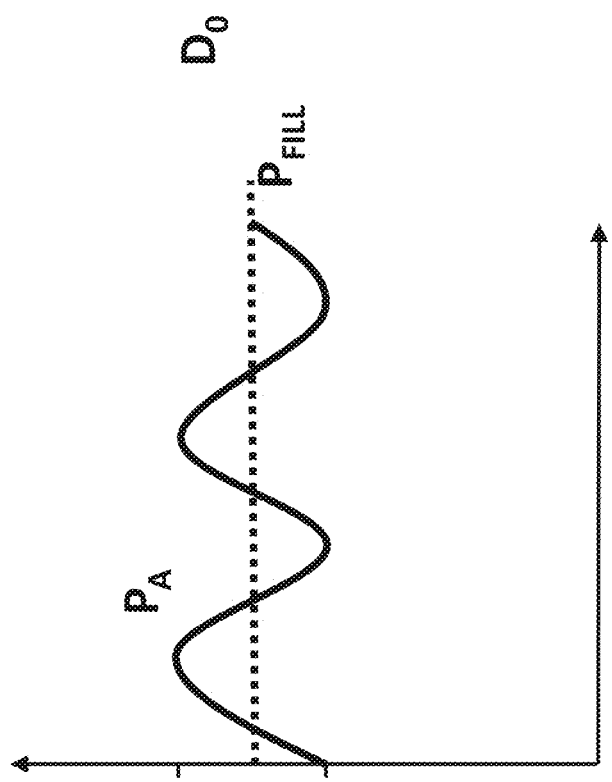

FIGS. 54A and 54B are plots of $P_A$ and $P_{FILL}$, and stent graft diameter versus time, respectively, when an aneurysm exclusion device comprising a filled aneurysm fill system pressurized such that the fill pressure $P_{FILL}$ in the inflatable fill structure is greater than the $P_{DIA}$, in accordance with an illustrative embodiment. FIG. 54A depicts the scenario from FIG. 51 in which the fill pressure $P_{FILL}$ (dotted line) is greater than the diastolic aortic pressure $P_{DIA}$ but less than the systolic aortic pressure $P_{SYS}$. The net inward pressure during the diastolic phase of the cardiac cycle causes the stent graft lumen to compress radially inward, as illustrated in FIG. 54B. The stent graft recoils to its fully expanded diameter $D_0$ during the systolic phase of the cardiac cycle.

Figure 55B:
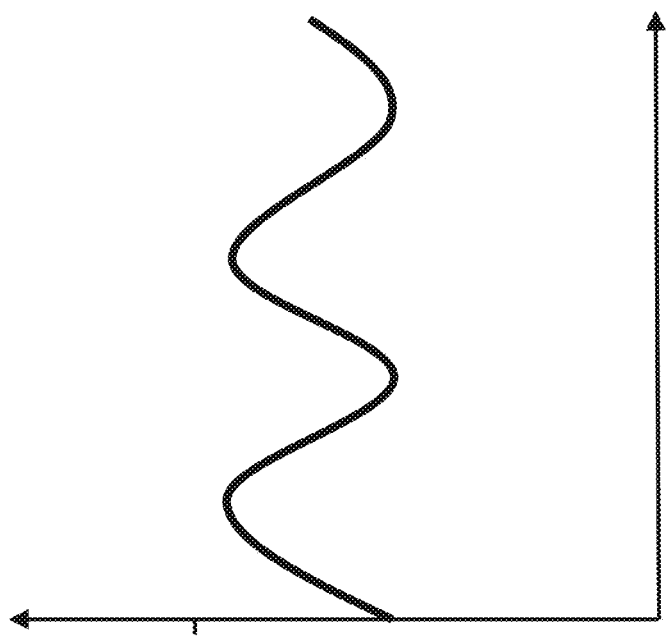
FIGS. 55A and 55B are plots of pressures $P_A$ and $P_{FILL}$, and stent graft diameter versus time, respectively, during aneurysm repair with an aneurysm exclusion device with an aneurysm fill system pressurized such that the fill pressure $P_{FILL}$ is greater than the $P_{SYS}$ and greater than a minimum pressure of a $P_{SEAL}$ pressure cycle, in accordance with an illustrative embodiment.
Figure 55A:
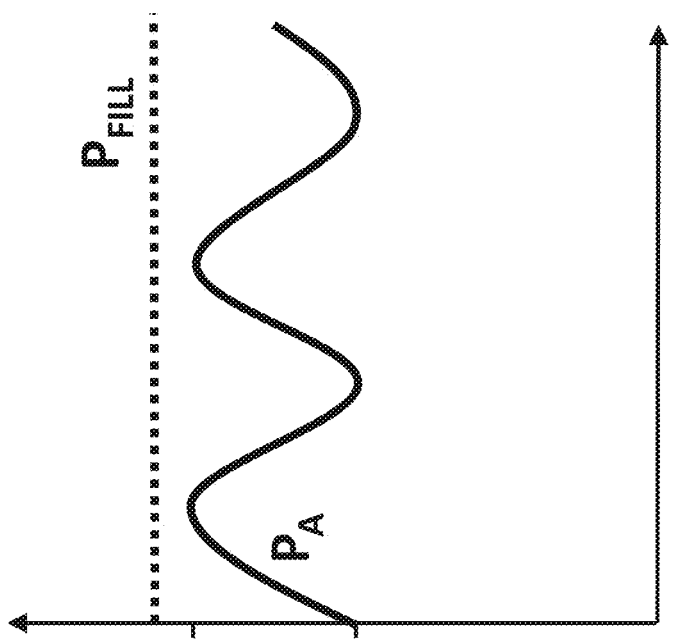

FIGS. 55A and 55B are plots of $P_A$ and $P_{FILL}$, and stent graft diameter, respectively, during aneurysm repair with an aneurysm exclusion device with an aneurysm fill system pressurized such that the fill pressure $P_{FILL}$ in the inflatable fill structure is greater than the $P_{SYS}$ and greater than the minimum pressure of the $P_{SEAL}$ pressure cycle, in accordance with an illustrative embodiment. FIG. 55A depicts the extreme scenario from FIG. 52 in which the fill pressure $P_{FILL}$ (dotted line) is greater than the systolic aortic pressure $P_{SYS}$. A net inward pressure acts on the stent graft during the cardiac cycle. As a result, the diameter of the stent graft lumen oscillates around values less than the fully expanded diameter $D_0$, as illustrated in FIG. 55B.

Based on the above analysis, it may be advantageous in various embodiments to fill an inflatable fill structure to a volume at which the fill pressure $P_{FILL}$ is less than the systolic aortic pressure $P_{SYS}$. This ensures that the fill pressure does not compromise the proximal and distal seal of the stent graft repair. In some embodiments, the final fill pressure $P_{FILL}$ can be closer to the diastolic aortic pressure $P_{DIA}$ than the systolic aortic pressure $P_{SYS}$. In some embodiments, the final fill pressure $P_{FILL}$ is in the range of $P_{DIA}-20$ mmHg and $P_{DIA}+20$ mmHg. In some embodiments, the final fill pressure $P_{FILL}$ is in the range of $P_{DIA}$ and $P_{DIA}+20$ mmHg.

In some embodiments, the fill pressure in an inflatable fill structure may be monitored by placing a pressure sensor into the inflatable fill structure. In some embodiments, the pressure sensor may be placed in a location that is in fluid communication with the inflatable fill structure. For example, the pressure sensor may be placed in a fill tube or in a reservoir containing the fill medium. In some embodiments, the pressure sensor may be placed in a separate cavity that is in fluid communication with the fill tube or the reservoir.

In some embodiments, a dynamic motion of a stent graft is utilized to determine a final fill volume of an inflatable fill structure. In various embodiments, the onset of an oscillatory inward motion of the stent graft as the heart beats is used as an indicator that the fill pressure is exceeding the diastolic aortic pressure. FIG. 54A, for example, depicts such a situation. In some embodiments, a radial motion of the stent graft may be imaged using ultrasound, x-ray, magnetic resonance imaging, etc. In a clinical setting, ultrasound and fluoroscopic imaging may be preferred. In some embodiments, an ultrasound probe is placed on an abdomen of a patient or inserted into the lumen of the stent graft. To enhance fluoroscopic imaging, contrast medium may be injected into the aorta to visualize the flow lumen in the stent graft.

Figure 56B:
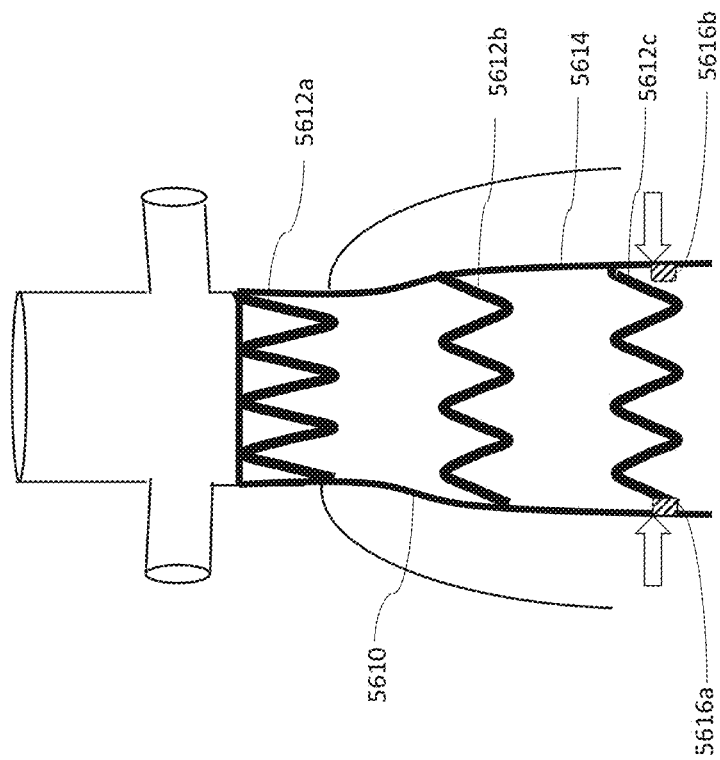
FIGS. 56A, 56B, 56C, and 56D are illustrations of stent graft embodiments showing reference locations and indicators, in accordance with illustrative embodiments.
Figure 56A:
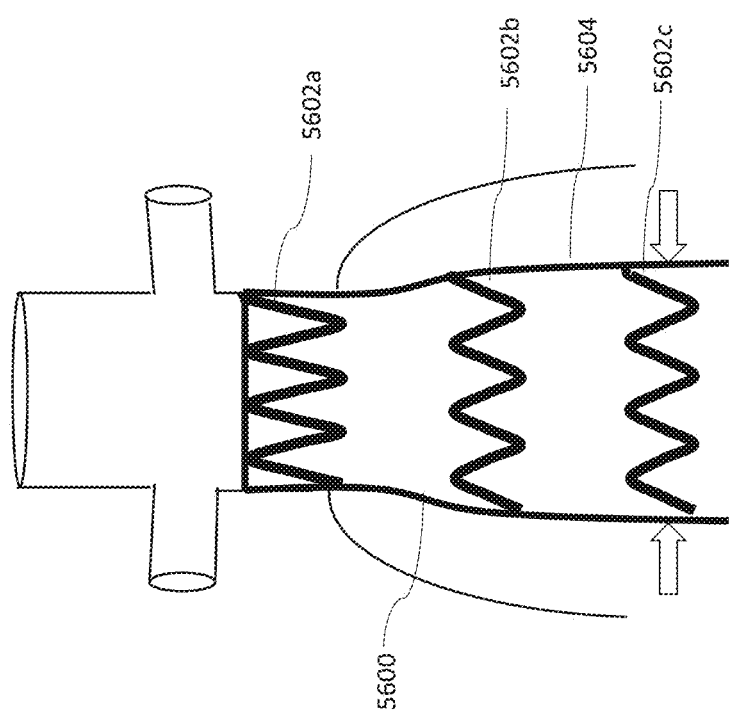

In some embodiments, radiopaque material placed on or adjacent to the stent graft may be visualized. FIGS. 56A, 56B, 56C, and 56D are illustrations of stent graft embodiments showing reference locations and indicators, in accordance with illustrative embodiments. With reference to FIG. 56A, a stent graft 5600 in accordance with various embodiments includes self-expanding stent elements 5602a, 5602b, and 5602c made from radiopaque material such as stainless steel, Co—Cr Alloy, or the like. The stent elements 5602a, 5602b, and 5602c can be directly visualized via an imaging device to monitor a diameter of a graft 5604 of the stent graft 5600. FIG. 56B illustrates a stent graft 5610 in accordance with an embodiment that includes stent elements 5612a, 5612b, and 5612c with low radiopaque properties, e.g., Nitinol. In various embodiments, radiopaque markers 5616a and 5616b are placed adjacent to, for example, the stent element 5612c on the stent graft 5610 for visualizing a dynamic motion of a graft 5614 of the stent graft 5610.

Figure 56D:
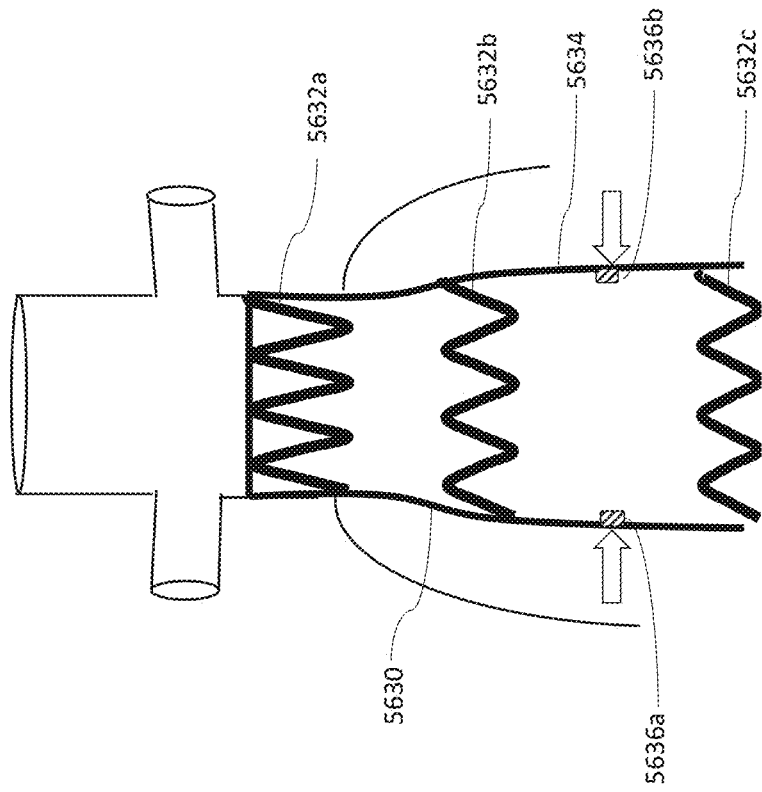
Figure 56C:
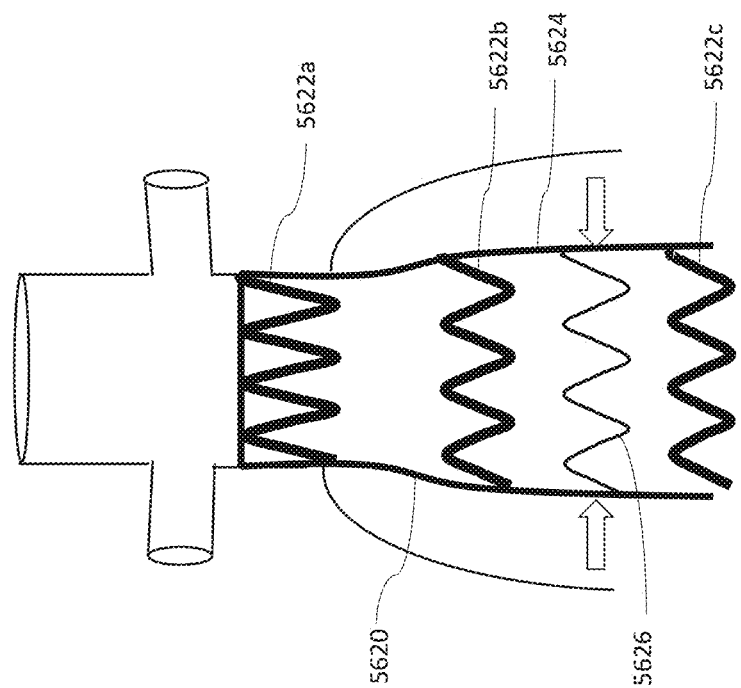

FIG. 56C illustrates a stent graft 5620 in accordance with an embodiment that includes a radiopaque stent element 5626 with an expansion force substantially less than an expansion force of adjacent stent elements 5622a, 5622b, and 5622c. In various embodiments, the radiopaque stent element 5626 is used for visualizing a motion of a graft 5624 of the stent graft 5620. In various embodiments, the weaker radiopaque stent element 5626 undergoes a higher amplitude of oscillation than the adjacent, stiffer stent elements 5622a, 5622b, and 5622c when the fill pressure of an inflatable fill structure around the stent graft 5620 exceeds the diastolic pressure, thus enhancing a sensitivity of detection.

FIG. 56D illustrates an embodiment to further enhance the sensitivity of detecting oscillatory radial motion of a stent graft. In various embodiments, a stent graft 5630 includes a segment of a graft 5634 between adjacent stent elements 5632b and 5632c that is monitored by placing radiopaque markers 5636a and 5636b in the segment of the graft 5634, as shown in FIG. 56D. The stent graft 5630 may also include a stent element 5632a. In various embodiments, radiopaque motion indicators may be placed any location along a graft that is in contact with an inflatable fill structure. In some embodiments, radiopaque motion indicators are placed along an inner wall of an inflatable fill structure. Such placement may be advantageous in situations where the inflatable fill structure is placed separately from the stent graft in the aneurysm and the stent graft does not otherwise have radiopaque motion indicators that can be utilized to detect the oscillatory radial motion of the graft.

Various embodiments described above of methods of monitoring an oscillatory radial motion of a graft can be used to determine a final fill volume of an inflatable fill structure. For example, the inflatable fill structure may be first filled with a test fluid until oscillatory motion of the graft is observed. The total injected volume of the test fluid can provide an estimate of a final fill volume. The test fluid can then be withdrawn from the inflatable fill structure and a permanent fill medium can be injected up to the estimated final fill volume without further monitoring. This approach may be preferred in situations where the permanent fill medium hardens rapidly after being injected into the inflatable fill structure, thus requiring rapid filling. Rapidly hardening fill media may quickly increase in viscosity, dampening pressure transmission to a pressure sensor. Also, rapidly hardening fill media may block fill lumens when not dispensed in a timely manner. The approach of a test fill may also be preferred in situations where the fill medium undergoes expansion after injection. For example, hydrogel based fill media may continue to swell after injection. Other reactive fill media may generate gases that expand the volume of the fill medium. The fill volume of the test fluid can be used to calculate the required injection volume of an expanding fill medium in order to reach the desired final fill volume of the fill medium in the inflatable fill structure.

In various embodiments, monitoring an onset of oscillatory motion of a graft to control an injection of fill medium is not limited to inflatable fill structures. The pressure relationships discussed above may also apply to situations in which a fill medium is directly injected into an open space in an aneurysm sac after stent graft repair. Thus, the methods of monitoring the radial motion of the graft can be used to control any type of fill medium injection into the aneurysm.

Referring again to FIG. 18, the second inflatable fill structure 1808 on the tubular graft 1802 acts as a ring-shaped inflatable fill element to create a seal between the tubular graft 1802 and an aortic wall. Referring again to FIG. 19, the stent graft 1902 includes the inflatable fill elements 1900 forming a scaffold to support the stent graft 1902 when the inflatable fill elements 1900 are filled with hardening fill medium. Referring again to FIGS. 43A-43F the inflatable fill elements 4312a, 4312b, 4312c, and 4312d of the aneurysm fill system support the inflatable fill structure 4306. In various embodiments, the inflatable fill elements in FIGS. 18, 19, and 43A-43F can be filled with hardening fluid fill medium. In some embodiments, a final fill pressure targeted for expanding those inflatable fill elements is different from the targeted fill pressure of the inflatable fill structure to fill the aneurysm sac.

Figure 57:
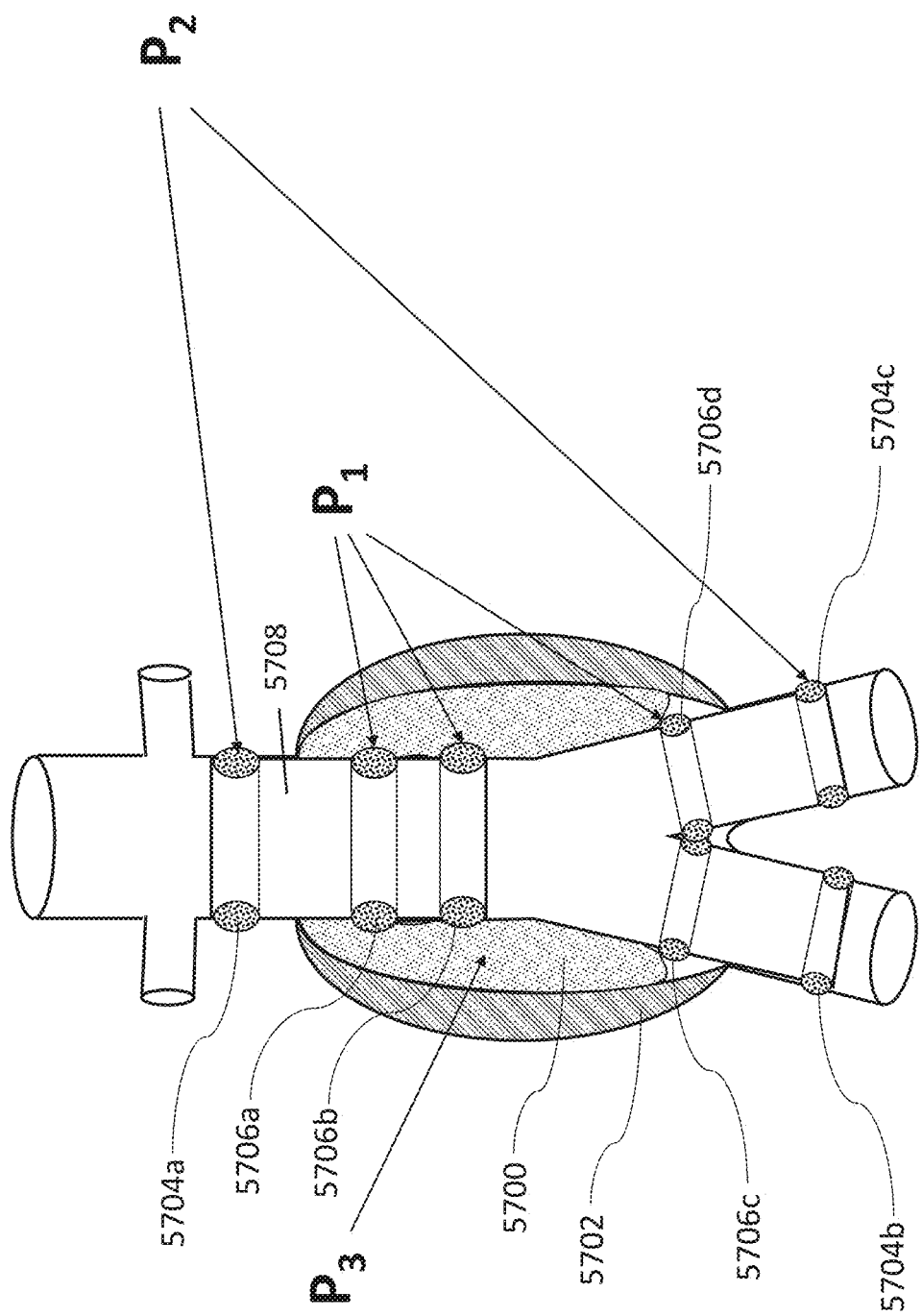
FIG. 57 is an illustration of a stent graft system with inflatable fill structures filled to various pressures, in accordance with an illustrative embodiment.

FIG. 57 is an illustration of a stent graft system with inflatable fill structures filled to various pressures, in accordance with an illustrative embodiment. In various embodiments, a stent graft system includes an inflatable fill structure 5700 that is placeable in an aneurysm 5702, ring-shaped inflatable fill elements 5704a, 5704b, and 5704c that provide a proximal and distal seal of a graft 5708, and a series of ring-shaped inflatable fill elements 5706a, 5706b, 5706c, and 5706d supporting the graft 5708. The ring-shaped inflatable fill elements 5704a-5704c and 5706a-5706d can be exposed to an aortic pressure $P_A$ that tends to collapse the inflatable fill elements 5704a-5704c and 5706a-5706d. In order for the inflatable fill elements 5704a-5704c and 5706a-5706d to fully expand, in various embodiments a fill pressure $P_1$ in the inflatable fill elements 5706a-5706d is set to be greater than the systolic aortic pressure $P_{SYS}$. Also, in various embodiments, a fill pressure $P_3$ of the inflatable fill structure 5700 in the aneurysm 5702 is set to be less than the systolic aortic pressure $P_{SYS}$. In various embodiments a fill pressure $P_2$ in the inflatable fill elements 5704a-5704c is set to maintain the proximal and distal seal of the graft 5708.

Figure 58:
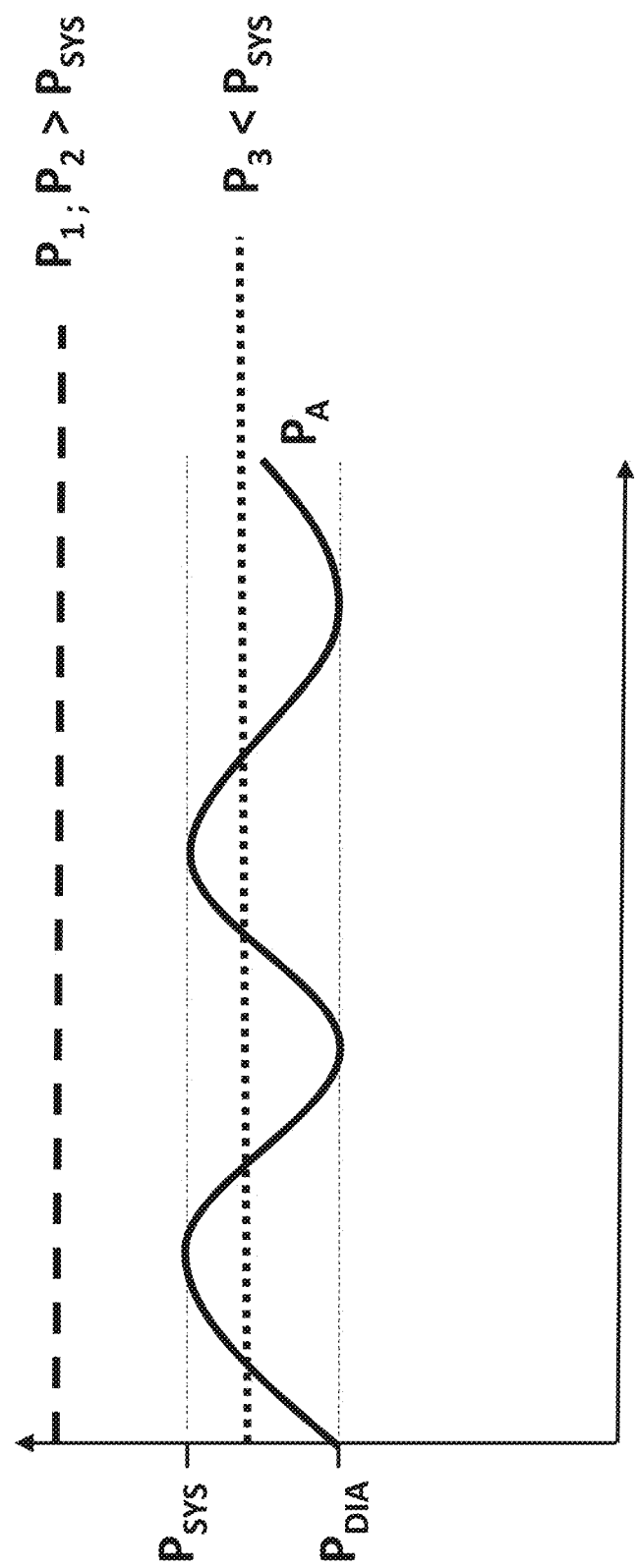
FIG. 58 is a plot of pressures $P_1$, $P_2$, $P_3$, $P_{SYS}$, $P_{DIA}$, and $P_{AORTA}$ versus time in inflatable fill structures, in accordance with an illustrative embodiment.

FIG. 58 is an example plot of pressures $P_1$, $P_2$, $P_3$, $P_{SYS}$, $P_{DIA}$, and $P_A$ versus time for a system as in FIG. 57, in accordance with an illustrative embodiment. With regard to FIGS. 57 and 58, the plot of FIG. 58 illustrates the aortic pressure $P_A$, the fill pressure $P_1$ of the inflatable fill elements 5706a-5706d, the fill pressure $P_2$ of the inflatable fill elements 5704a-5704c, and the fill pressure $P_3$ of the inflatable fill structure 5700 in the aneurysm 5702. In various embodiments, a stent graft system includes an inflatable fill structure for filling the aneurysm and inflatable fill elements for supporting and/or sealing a graft. In various embodiments, the inflatable fill structure 5700 is filled with a fill medium to a targeted fill pressure $P_3$ that is less than the systolic aortic pressure $P_{SYS}$ of the patient, and the inflatable fill elements 5706a-5706d and 5704a-5704c are filled with a fill medium to targeted fill pressures $P_1$ and $P_2$ that are greater than the systolic aortic pressure $P_{SYS}$ of the patient.

In various embodiments, fill medium can be injected from a reservoir into an aneurysm sac or into an inflatable fill structure placed in the aneurysm sac. In some embodiments, the reservoir may include a syringe and fill medium can be dispensed by pushing a plunger in the syringe. In some embodiments, a fluid fill medium is transported by a pump from the reservoir. In some embodiments, the fluid fill medium may be expelled from the reservoir by pressurizing the reservoir with a gas. In various embodiments, an operator controls the filling process, and the operator terminates the filling process once a desired fill volume is reached. In some embodiments, a target pressure below a systolic aortic pressure of the patient may be selected for terminating the filling process. In some embodiments, an indicator for reaching the target pressure is a pressure sensor in fluid communication with the fill medium. In various embodiments, an indicator for reaching the target pressure is oscillatory motion of a graft in response to the fill pressure. A method of filling an aneurysm sac with a fill medium in accordance with an embodiment includes pressurizing a reservoir to a target fill pressure to drive fill medium into the aneurysm sac.

Figure 59:
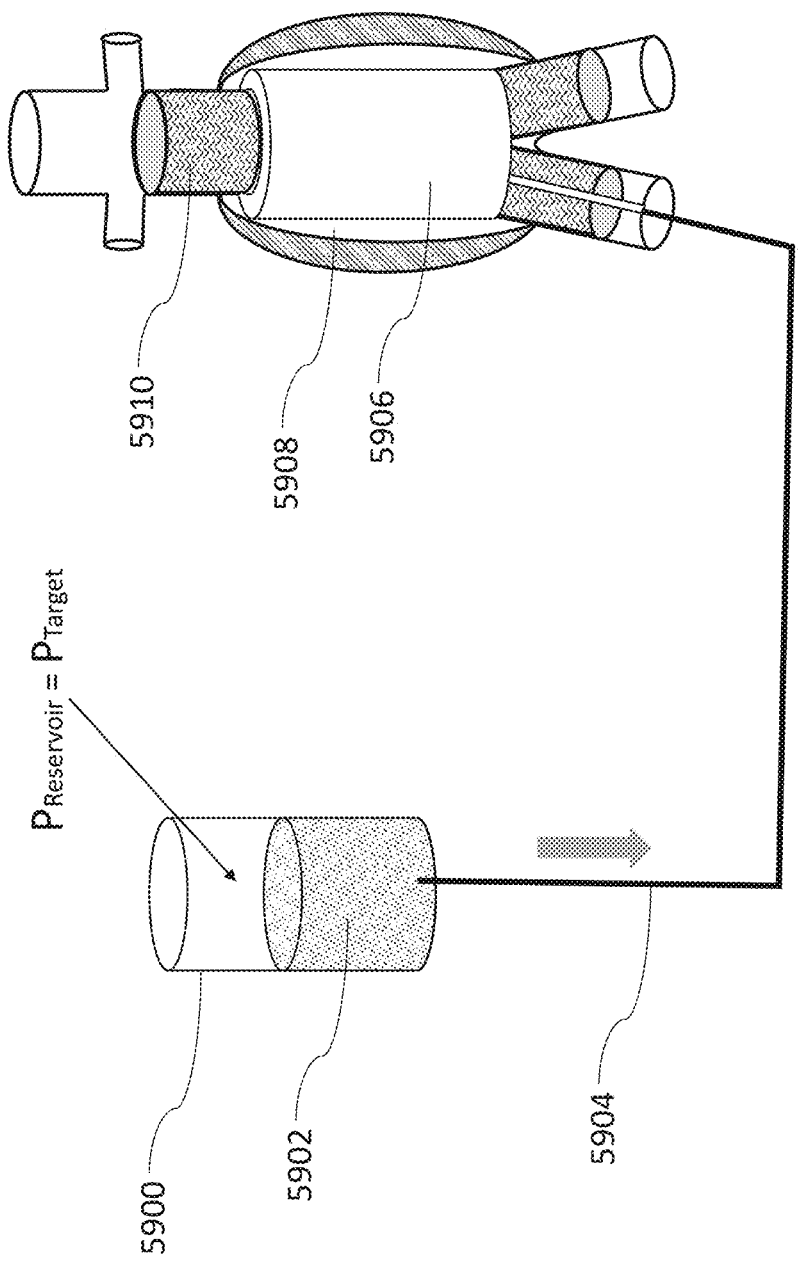
FIG. 59 is a diagram of a reservoir system having an internal pressure $P_{RESERVOIR}$ equal to $P_{TARGET}$, in accordance with an illustrative embodiment.

FIG. 59 illustrates a system including a reservoir system having an internal pressure $P_{RESERVOIR}$ equal to a target pressure $P_{TARGET}$ for an inflatable fill structure in accordance with an illustrative embodiment. In various embodiments, a fluid reservoir 5900 stores fill medium 5902, and a fill tube 5904 connects the reservoir 5900 to an inflatable fill structure 5906 in an aneurysm 5908. In various embodiments, a stent graft 5910 that is at least partially within the inflatable fill structure 5906 excludes the aneurysm 5908. To transport the fill medium 5902 from the reservoir 5900 into the inflatable fill structure 5906, the pressure in the reservoir 5900 can be set to be greater than a pressure in the inflatable fill structure 5906. In various embodiments, flow of the fill medium 5902 into the inflatable fill structure 5906 ceases when the pressure in the inflatable fill structure 5906 reaches the pressure in the reservoir 5900. In some embodiments, to fill the inflatable fill structure 5906 to a certain target fill pressure, the reservoir 5900 is pressurized to the target fill pressure. In such embodiments, the fill medium 5902 flows from the reservoir 5900 to the inflatable fill structure 5906 until the target pressure is reached. At that point, the pressure in the inflatable fill structure 5906 and the pressure in the reservoir 5900 are in equilibrium, and the filling process stops.

In some such embodiments, the filling process is self-controlled and does not require active control by an operator. The risk of accidental over-filling of the inflatable fill structure 5906 by an operator can, thus, be avoided. The driving pressure in the reservoir 5900 may be generated, for example, from an external source such as gas bottle with a pressure regulator. It may also be generated, for example, by suspending the reservoir 5900 above the patient to create a pressure differential proportional to an elevation of the reservoir 5900 above the aneurysm 5908.

In some embodiments, a blood vessel of the patient can be used as a pressure source to drive fill medium from the reservoir into the inflatable fill structure. FIG. 60 is a plot of relative nominal blood pressure in substructures of the circulatory system. Blood pressure in an arterial system can decrease the further away from the heart the measurement point is. For example, the mean blood pressure in the thoracic aorta is greater than the blood pressure in the abdominal aorta, and so forth.

FIG. 61 is a diagram showing system including a reservoir system in communication with a contained space of a fill system in an aneurysm, in accordance with an illustrative embodiment. In various embodiments, a reservoir 6100 includes two chambers 6102 and 6104. In some embodiments, the two chambers 6102 and 6104 are separated by a flexible membrane 6106. The first chamber 6102 contains the fill medium. In some embodiments, a first fill line 6107 connects the first chamber 6102 to an inflatable fill structure 6108 in an aneurysm 6110. Also, in some embodiments, a second fill line 6112 is inserted into an artery 6114 of the patient and is connected to the second chamber 6104 of the reservoir 6100. The second fill line 6112 may be inserted into the artery 6114, for example, using a needle. In some embodiments, the second fill line 6112 is connected to a catheter lumen that is in fluid communication with the artery 6114. In some embodiments, an arterial vessel at or distal to the aneurysm 6110 may be selected to help ensure that the driving pressure does not exceed the systolic aortic pressure in the lumen of a stent graft 6116 that is at least partially within the inflatable fill structure 6108.

In various embodiments, the second chamber 6104 is pre-filled with a fluid such as saline or water to minimize blood loss. Blood can flow from the artery 6114 of the patient into the second chamber 6104 until the pressure in the second chamber 6104 reaches the arterial pressure in the artery 6114. The pressure in the second chamber 6104 applies a force to the membrane 6106 and creates a pressure in the first chamber 6102 that is equal to a pressure in the second chamber 6104, which is equal to (or substantially similar to) the arterial pressure. Fill medium is then expelled from the first chamber 6102 into the inflatable fill structure 6108 until the pressure in the inflatable fill structure 6108 reaches the arterial pressure in the artery 6114. The method of using the arterial pressure as a driving pressure may also be used when filling the aneurysm sac directly without an inflatable fill structure retaining the fill medium.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. Various modifications and changes that come within the meaning and range of equivalency of the claims are intended to be within the scope of the invention.

What is claimed is:

1. A method comprising:
inserting a first delivery catheter into an aneurysm, wherein the delivery catheter comprises a first stent graft and an inflatable fill structure fixed to a portion of an outside surface of the first stent graft, and wherein the first stent graft has a first end and a second end;
deploying the first stent graft in the aneurysm; and
filling the inflatable fill structure with a fill medium, wherein a portion of the inflatable fill structure is configured to extend from a position confined between the first and second ends of the first stent graft when in an unfilled state to beyond at least one of the first end of the first stent graft or the second end of the first stent graft when the inflatable fill structure is in a filled state.

2. The method of claim 1, further comprising:
inserting a second delivery catheter into the aneurysm, wherein the second delivery catheter comprises a second stent graft with a first end and a second end and deploying the second stent graft in the aneurysm, wherein a portion of the first stent graft surrounds a first portion of the second stent graft.

3. The method of claim 2, wherein the portion of the inflatable fill structure is configured to extend over a second portion of the second stent graft when the inflatable fill structure is in a filled state.

4. The method of claim 3, wherein the first portion of the second stent graft is adjacent to the second portion of the second stent graft.

5. The method of claim 2, wherein the portion of the inflatable fill structure is configured to expand beyond the first end of the first stent graft when the inflatable fill structure is in a filled state, and wherein the portion of the first stent graft that surrounds the first portion of the second stent graft is on the first end of the first stent graft.

6. The method of claim 1, wherein the second end of the first stent graft comprises a first lumen and a second lumen.

7. The method of claim 6, wherein said deploying the first stent graft comprises inserting the first lumen into a first blood vessel and inserting the second lumen into a second blood vessel.

8. The method of claim 6, further comprising:
inserting a second delivery catheter into the aneurysm, wherein the second delivery catheter comprises a second stent graft with a first end and a second end; and
deploying the second stent graft in the aneurysm, wherein a portion of the first lumen surrounds a portion of the second stent graft.

9. The method of claim 8, wherein the portion of the inflatable fill structure that is configured to extend beyond an end of the first stent graft is further configured to extend over the second stent graft.

10. The method of claim 6, further comprising:
inserting a third delivery catheter into the aneurysm, wherein the third delivery catheter comprises a third stent graft with a first end and a second end; and
deploying the third stent graft in the aneurysm, wherein a portion of the second lumen surrounds a portion of the third stent graft.

11. The method of claim 10, wherein the portion of the inflatable fill structure that is configured to extend beyond an end of the first stent graft is further configured to extend over the second stent graft and the third stent graft.

12. A method comprising:
inserting a delivery catheter into an aneurysm, wherein the delivery catheter comprises
an inflatable fill structure, comprising an inside surface; and
a stent graft, and wherein the inflatable fill structure is fixed to a portion of an outside surface of the stent graft;
deploying the inflatable fill structure into the aneurysm;
filling the inflatable fill structure with a fill medium to a first pressure such that the fill structure confined between a first and a second end of the stent graft in an uninflated state expands beyond an end of the stent graft; and
monitoring movement of the inside surface of the inflatable fill structure.

13. The method of claim 12, wherein the inside surface of the inflatable fill structure comprises a radiopaque material.

14. The method of claim 13, wherein the radiopaque material comprises at least two markers located on opposite sides of the inflatable fill structure.

15. The method of claim 14, wherein the at least two markers are not located over another radiopaque material.

16. The method of claim 13, wherein the radiopaque material comprises a first expandable scaffold.

17. The method of claim 16, wherein the inflatable fill structure comprises a second expandable scaffold, wherein a radial force of the first expandable scaffold is less than a radial force of the second expandable scaffold.

18. The method of claim 13, wherein said monitoring movement of the inside surface of the inflatable fill wherein comprises monitoring movement of the radiopaque material via an x-ray machine or a magnetic resonance imaging machine.

19. The method of claim 12, wherein the movement of the inside surface of the inflatable fill structure is caused by a difference in blood pressure within a lumen formed by the inside surface of the inflatable fill structure.

* * * * *